(12) United States Patent
Parhami et al.

(10) Patent No.: US 8,022,052 B2
(45) Date of Patent: Sep. 20, 2011

(54) INHIBITION OF PPAR GAMMA EXPRESSION BY SPECIFIC OSTEOGENIC OXYSTEROLS

(75) Inventors: Farhad Parhami, Los Angeles, CA (US); Woo-Kyun Kim, Los Angeles, CA (US); Michael E. Jung, Los Angeles, CA (US); Khanhlinh Nguyen, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/520,281

(22) PCT Filed: Dec. 19, 2007

(86) PCT No.: PCT/US2007/025833
§ 371 (c)(1),
(2), (4) Date: Dec. 14, 2009

(87) PCT Pub. No.: WO2008/082520
PCT Pub. Date: Jul. 10, 2008

(65) Prior Publication Data
US 2010/0105645 A1    Apr. 29, 2010

Related U.S. Application Data

(60) Provisional application No. 60/875,913, filed on Dec. 19, 2006.

(51) Int. Cl.
*A61K 31/56* (2006.01)
(52) U.S. Cl. .......................... 514/170; 514/182
(58) Field of Classification Search .................. 514/170, 514/182
See application file for complete search history.

(56) References Cited

U.S. PATENT DOCUMENTS

| | | | |
|---|---|---|---|
| 3,887,545 | A | 6/1975 | Iacobelli et al. |
| 4,183,852 | A | 1/1980 | Kaiser |
| 4,743,597 | A | 5/1988 | Javitt et al. |
| 5,929,062 | A | 7/1999 | Haines |
| 6,080,779 | A | 6/2000 | Gasper et al. |
| 6,184,215 | B1 | 2/2001 | Elias et al. |
| 6,586,189 | B2 | 7/2003 | Forman |
| 6,893,830 | B1 | 5/2005 | Janowski et al. |
| 2003/0153541 | A1 | 8/2003 | Dudley et al. |
| 2004/0176423 | A1 | 9/2004 | Paralkar |
| 2004/0235739 | A1 | 11/2004 | Mahanthappa |
| 2005/0095677 | A1 | 5/2005 | Liu et al. |
| 2006/0270645 | A1 | 11/2006 | Parhami |
| 2008/0070883 | A1 | 3/2008 | Nagpal |

FOREIGN PATENT DOCUMENTS

| | | |
|---|---|---|
| GB | 2 320 190 | 6/1998 |
| WO | WO 97/40137 | 10/1997 |
| WO | WO 00/54759 | 9/2000 |
| WO | WO 01/15676 | 3/2001 |
| WO | WO 02/080952 | 10/2002 |
| WO | WO-2004/019884 | 3/2004 |
| WO | WO 2004/019884 | 3/2004 |
| WO | WO-2005/020928 | 3/2005 |
| WO | WO 2005/028616 | 3/2005 |
| WO | WO 2005/020928 | 10/2005 |
| WO | WO 2006/012902 | 9/2006 |
| WO | WO-2006/110490 | 10/2006 |
| WO | WO 2006/110490 | 10/2006 |
| WO | WO 2007/098281 | 1/2007 |
| WO | WO 2007/028101 | 3/2007 |
| WO | WO-2007/028101 | 3/2007 |
| WO | WO-2007/098281 | 8/2007 |
| WO | WO 2008/041003 A2 | 4/2008 |
| WO | WO 2008/115469 | 9/2008 |

OTHER PUBLICATIONS

Aghaloo et al.; Oxysterols enhance osteoblast differentiation in vitro and bone healing in vivo; J. Bone & Mineral Research 2005, 20(9): S361, Abstract M203, 27th Annual Meeting of American Society for Bone and Mineral Research.

Aghaloo TL, Amantea CM, Cowan CM, Richardson JA, Wu BM, Parhami F, Tetradis S. Oxysterols enhance osteoblast differentiation in vitro and bone healing in vivo. J Orthop Res. Nov. 2007;25(11):1488-97 (also known as Aghaloo 2006 in press).

Akazawa C, Isuzuki H, Nakamura Y, Sasaki Y, Ohsaki K, Nakamura S, arakawa Y, Kohsaka S. The upregulated expression of sonic hedgehog in motor neurons after rat facial nerve axotomy. J Neuroscience 2004; 24:7923-7930.

Almeida M, Han L, Bellido T, Manolagas SC, Kousteni S. Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT. J Biol Chem. Dec. 16, 2005;280(50):41342-51.

Amantea CM et al. 2006, Oxysterols are novel activators of hedgehog and Wnt signaling, J Bone Miner Res 21:SI;S156.

Banerjee C, McCabe LR, Choi JY, Hiebert SW, Stein JL, Stein GS, Lian JB. Runt homology domain proteins in osteoblast differentiation: AML3/CBFA1 is a major component of a bone-specific complex. J Cell Biochem. Jul. 1, 1997;66(1):1-8.

Bannai K, Morisaki M, Ikekawa N. Studies on steroids. Part 37. Synthesis of the four stereoisomers of 20,22-epoxycholesterol. J Chem Soc Perkins Trans 1 1979; 2116-2120.

Basu S, Michaëlsson K, Olofsson H, Johansson S, Melhus H. Association between oxidative stress and bone mineral density. Biochem Biophys Res Commun. Oct. 19, 2001;288(1):275-9.

Beckers L et al.; Disruption of hedgehog signalling in ApoE −/−mice reduces plasma lipid levels, but increases atherosclerosis due to enhanced lipid uptake by macrophages; Journal of Pathology 2007, 212(4): 420-428.

Bennett CN, Longo KA, Wright WS, Suva LJ, Lane TF, Hankenson KD, MacDougald OA. Regulation of osteoblastogenesis and bone mass by Wnt10b. Proc Natl Acad Sci U S A. Mar. 1, 2005;102(9):3324-9.

(Continued)

*Primary Examiner* — Raymond Henley, III
(74) *Attorney, Agent, or Firm* — Venable LLP; Nancy J. Axelrod; Michael A. Gollin

(57) ABSTRACT

This invention relates to methods for using agents to inhibit peroxisome proliferator activated receptor expression.

19 Claims, 10 Drawing Sheets

OTHER PUBLICATIONS

Bennett CN, Ross SE, Longo KA, Bajnok L, Hemati N, Johnson KW, Harrison SD, MacDougald OA. Regulation of Wnt signaling during adipogenesis. J Biol Chem. Aug. 23, 2002;277(34):30998-1004.

Bergman RJ, Gazit D, Kahn AJ, Gruber H, McDougall S, Hahn TJ. Age-related changes in osteogenic stem cells in mice. J Bone Miner Res 1996; 11:568-577.

Bestmann HJ, Soliman FM. Synthesis and reaction of diazoacetyl chloride. Angew Chem 1979; 91:1012-1013.

Bijlsma MF, Peppelenbosch MP, Spek A. Hedgehog morphogen in cardiovascular disease. Circulation 114:1985-1991; 2006.

Bijlsma MF, Spek CA, Peppelenbosch MP. Hedgehog: an unusual signal transducer. BioEssays 26:387-394; 2004.

Bilezikian JP, Kurland ES. Therapy of male osteoporosis with parathyroid hormone. Calcif Tissue Int 2001; 69:248-251.

Bjorkhem I, Diczfalusy U. Oxysterols: friends, foes, or just fellow passengers? Arterioscler Thromb Vasc Biol 22:734-742; 2002.

Bjorkhem I, Meaney S, Diczfalusy U. Oxysterols in human circulation: which role do they play? Curr Opin Lipidol 13:247-253; 2002.

Bjorkhem I, Reihner E, Angelin B, Ewerth S, Akerlund J, Einarsson K. On the possible use of the serum level of 7α-hydroxycholesterol as a marker for incrased activity of the cholesterol 7β-hydroxylase in humans. J Lipid Res 1987; 28:889-894.

Boguslawski G, Hale LV, Yu XP, Miles RR, Onyia JE, Santerre RF, Chandrasekhar S. Activation of osteocalcin transcription involves interaction of protein kinase A- and protein kinase C-dependent pathways. J Biol Chem. Jan. 14, 2000;275(2):999-1006.

Boland GM, Perkins G, Hall DJ, Tuan RS. Wnt 3a promotes proliferation and suppresses osteogenic differentiation of adult human mesenchymal stem cells. J Cell Biochem. Dec. 15, 2004;93(6):1210-30.

Braunersreuther V, Mach F. Leukocyte recruitment in atherosclerosis: potential targets for therapeutic approaches? Cell Mol Life Sci 63:2079-2088; 2006.

Bunta W, Yoshiaki N, Takehiko O, Hisashi M. Steroids 2004, 69: 483-493.

Burger A, Colobert F, Hetru C, Luu B. Tetrahedron 1988, 44: 1141-1152.

Byon C, Gut M. Stereospecific synthesis of the four 20,22-epoxycholesterols and of (Z)-20(22)-Dehydrocholesterol. J Org Chem 1976; 41:3716-3722.

Byrd N, Grebel L. Hedgehog signaling in murine vasculogenesis and angiogenesis. Trends Cardiovasc Med 14:308-313; 2004.

Cadot C, Poirier D, Philip A. Tetrahedron 2006, 62: 4384-4392.

Caplan AI, Bruder SP. Mesenchymal stem cells: building blocks for molecular medicine in the 21st century. Trends Mol Med. Jun. 2001;7(6): 259-64. Review.

Caplan AI. The mesengenic process. Bone Repair and Regeneration 1994; 21:429-435.

Chan GK, Duque G. Age-related bone loss: old bone, new facts. Gerontology 2002; 48:62-71.

Chaudhuri NK, Williams IG, Nickolson R, Gut M. Stereochemistry of the addition reactions of Grignard reagents to 20-keto steroids. Syntheses of 17α,20α-dihydroxycholesterol. J Org Chem 1969; 34:3759-3766.

Chen D, Zhao M, Mundy GR. Bone morphogenetic proteins. Growth Factors. Dec. 2004;22(4):233-41. Review.

Chen JK, Iaipale J, Cooper MK, Beachy PA. Inhibition of hedgehog signaling by direct binding of cyclopamine to Smoothened. Genes & Develop 2002; 16:2743-2748.

Chen XD, Shi S, Xu T, Robey PG, Young MF. Age-related osteoporosis in biglycan-deficient mice is related to defects in bone marrow stromal cells. J Bo ne Miner Res. Feb. 2002;17(2):331-40.

Choo et al., Otolaryngology Head Neck Surgery 1999, 120: 84-91.

Chuu CP, Chen RY, Hiipakka RA, Kokontis JM, Warner KV, Xiang J, Liao S. The liver X receptor agonist T0901317 acts as androgen receptor antagonist in human prostate cancer cells. Biochem Biophys Res Commun. Jun. 1, 2007;357(2):341-6. Epub Mar. 28, 2007.

Chuu CP, Hiipakka RA, Kokontis JM, Fukuchi J, Chen RY, Liao S. Inhibition of tumor growth and progression of LNCaP prostate cancer cells in athymic mice by androgen and liver X receptor agonist. Cancer Res. Jul. 1, 2006;66(13):6482-6.

Clément-Lacroix P, Ai M, Morvan F, Roman-Roman S, Vayssière B, Belleville C, Estrera K, Warman ML, Baron R, Rawadi G. Lrp5-independent activation of Wnt signaling by lithium chloride increases bone formation and bone mass in mice. Proc Natl Acad Sci U S A. Nov 29, 2005;102(48):17406-11.

Clevers H. Wnt/beta-catenin signaling in development and disease. Cell. Nov. 3, 2006;127(3):469-80. Review.

Cohen MM. The hedgehog signaling network. Am J Med Gen 2003; 123A:5-28.

Corcoran RB and Scott MP. Oxysterols stimulate sonic hedgehog and proliferation of medulloblastoma cells. Proceedings of the National Academy of Sciences 2006, 103(22): 8408-8413.

Cummings SR, Melton LJ. Epidemiology and outcomes of osteoporotic fractures. Lancet. May 18, 2002;359(9319):1761-7. Review.

Day TF, Guo X, Garrett-Beal L, Yang Y. Wnt/beta-catenin signaling in mesenchymal progenitors controls osteoblast and chondrocyte differentiation during vertebrate skeletogenesis. Dev Cell. May 2005;8(5):739-50.

De la Rosa MA, Velarde E, Guzman A. Synthetic Commun. 1990, 20: 2059-2064.

Debiais F, Lefèvre G, Lemonnier J, Le Mée S, Lasmoles F, Mascarelli F, Marie PJ. Fibroblast growth factor-2 induces osteoblast survival through a phosphatidylinositol 3-kinase-dependent, -beta-catenin-independent signaling pathway. Exp Cell Res. Jul. 1, 2004;297(1):235-46.

Devos A, Remion J, Frisque-Hesbain AM, Colens A, Ghosez L. Syntheseis of acyl halides under very mild conditions. J Chem soc Chem Commun 1979; 1180-1181.

Drew J, Letellier M, Morand P, Szabo AG. J of Org. Chem 1987, 52: 4047-4052 (no detailed info found in PubMed).

Ducy P, Zhang R, Geoffroy V, Ridall AL, Karsenty G. Osf2/Cbfal : A transcriptional activator of osteoblast differentiation. Cell 1997; 89:747-754.

Ducy P. Cbfal : a molecular switch in osteoblast biology. Dev Dyn. Dec. 2000;219(4):461-71.

Dwyer JR, Sever N, Carlson M, Nelson SF, Beachy PA, Parhami F. Oxysterols are novel activators of the hedgehog signaling pathway in pluripotent mesenchymal cells. J Biol Chem 2007, 282: 8956-8968.

Eastell R. Treatment of postmenopausal osteoporosis. New Eng J Med 1998; 338(11):736-746.

Edwards PA, Ericsson J. Sterols and isoprenoids: signaling molecules derived from the cholesterol biosynthetic pathway. Annu Rev Biochem 68:157-185; 1999.

Edwards PA, Kast HR, Anisfeld AM. BAREing it all: the adoption of LXR and FXR and their roles in lipid metabolism. J Lipid Res 2002; 43:2-12.

Ettinger MP. Aging bone and osteoporosis: strategies for preventing fractures in the elderly. Arch Intern Med. Oct. 13, 2003;163(18):2237-46. Review.

European Search Report (EP 03749213.9) dated Jun. 15, 2009.

European Search Report in 256918 EP mailed Jul. 1, 2009 (suppl., EP 06824888.9).

Fajas L, Schoonjans K, Gelman L, Kim JB, Najib J, Martin G, Fruchart JC, Briggs M, Spiegelman BM, Auwerx J. Regulation of peroxisome proliferator-activated receptor gamma expression by adipocyte differentiation and determination factor 1/sterol regulatory element binding protein 1: implications for adipocyte differentiation and metabolism. Mol Cell Biol. Aug. 1999;19(8):5495-503.

Franceschi RT, Wang D, Krebsbach PH, Rutherford RB. Gene therapy for bone formation: in vitro and in vivo osteogenic activity of an adenovirus expressing BMP7. J Cell Biochem. Jun. 6, 2000;78(3):476-86.

Franceschi RT, Xiao G. Regulation of the osteoblast-specific transcription factor, Runx2: responsiveness to multiple signal transduction pathways. J Cell Biochem. Feb. 15, 2003;88(3):446-54. Review.

Fujita T, Azuma Y, Fukuyama R, Hattori Y, Yoshida C, Koida M, Ogita K, Komori T. Runx2 induces osteoblast and chondrocyte differentiation and enhances their migration by coupling with PI3K-Akt signaling. J Cell Biol. Jul. 5, 2004;166(1):85-95. Epub Jun. 28, 2004.

Fukuchi J, Kokontis JM, Hiipakka RA, Chuu CP, Liao S. Antiproliferative effect of liver X receptor agonists on LNCaP human prostate cancer cells. Cancer Res. Nov. 1, 2004;64(21):7686-9.

Galus R et al.; Fluvastatin does not elevate periosteal osteogenesis induced by Moloney sarcoma virus (MSV) in mice. Pharmacol. Rep. 2006, 58(1): 60-66.

Garrett IR, Chen D, Gutierrez G, Zhao M, Escobedo A, Rossini G, Harris SE, Gallwitz W, Kim KB, Hu S, Crews CM, Mundy GR. Selective inhibitors of the osteoblast proteasome stimulate bone formation in vivo and in vitro. J Clin Invest. Jun. 2003;111(11):1771-82.

Gaur T, Lengner CJ, Hovhannisyan H, Bhat RA, Bodine PV, Komm BS, Javed A, van Wijnen AJ, Stein JL, Stein GS, Lian JB. Canonical WNT signaling promotes osteogenesis by directly stimulating Runx2 gene expression. J Biol Chem. Sep. 30, 2005;280(39):33132-40. Epub Jul. 25, 2005.

Gen AVD, Wiedhaup K, Swoboda JJ, Dunathan HC, Johnson WS. J Am Chem Soc 1973, 95: 2656-2663.

Ghosh-Choudhury N, Abboud SL, Nishimura R, Celeste A, Mahimainathan L, Choudhury GG. Requirement of BMP-2-induced phosphatidylinositol 3-kinase and Akt serine/threonine kinase in osteoblast differentiation and Smad-dependent BMP-2 gene transcription. J Biol Chem. Sep. 6, 2002;277(36):33361-8. Epub Jun. 25, 2002. Erratum in: J Biol Chem. May 2, 2003;278(18):16452.

Ghosh-Choudhury N, Mandal CC, Choudhury GG. Statin-induced Ras activation integrates the phosphatidylinositol 3-kinase signal to Akt and MAPK for bone morphogenetic protein-2 expression in osteoblast differentiation. J Biol Chem. Feb. 16, 2007;282(7):4983-93.

Gimble JM, Robinson Covered Entity, Wu X, Kelly KA, Rodriguez BR, Kliewer SA, Lehmann JM, Morris DC. Peroxisome proliferator-activated receptor-γactivation by thiazolidinediones induces adipogenesis in bone marrow stromal cells. Mol Pharmacol 1996; 50:1087-1094.

Goltzman D. Discoveries, drugs and skeletal disorders. Nat Rev Drug Discov. Oct. 2002;1(10):784-96.

Gordon MD, Nusse R. Wnt signaling: multiple pathways, multiple receptors, and multiple transcription factors. J Biol Chem. Aug. 11, 2006;281(32):22429-33. Epub Jun. 22, 2006. Review.

Gori F, Thomas T, Hicok KC, Spelsberg TC, Riggs BL. Differentiation of human marrow stromal precursor cells: bone morphogenetic protein-2 increases OSF2/CBFA1, enhances osteoblast commitment, and inhibits late adipocyte maturation. J Bone Miner Res. Sep. 1999;14(9):1522-35.

Hanada K, Dennis JE, Caplan AI. Stimulatory effects of basic fibroblast growth factor and bone morphogenetic protein-2 osteogenic differentiation of rat bone marrow-derived mesenchymal stem cells. J. Bone and Mineral Research 1997, 12(10): 1606-1614.

Hanley K, NG DC, He SS, Lau P, Min K, Elias PM, Bikle DD, Mangelsdorf DJ, Williams ML, Feingold KR. Oxysterols induce differentiation in human keratinocytes and increase AP-1-dependent involucrin transcription. J Invest Dermatol 2000; 114:545-553.

Hayden JM, Brachova L, Higgins K, Obermiller L, Sevanian A, Khandrika S, Reaven PD. Induction of moncyte differentiation and foam cell formation in vitro by 7-ketocholesterol. J Lipid Res 2002; 43:26-35.

Hicok KC, Thomas T, Gori F, Rickard DJ, Spelsberg TC, Riggs BL. Development and characterization of conditionally immortalized osteoblast precursor cell lines from human bone marrow stroma. J Bone Miner Res 1998; 13(2):205-2217.

Hill TP, Später D, Taketo MM, Birchmeier W, Hartmann C. Canonical Wnt/beta-catenin signaling prevents osteoblasts from differentiating into chondrocytes. Dev Cell. May 2005;8(5):727-38.

Honda M, Komori T. Biologically active glycosides from Asteroidia. XI. Structures of thornasterols A and B. Tetrahedron Lett 1986; 27:3396-3372.

Honda T, Katoh M, Yamane S. J Chem Soc., Perkin Trans. 1996, 1: 2291-2296 (no detailed info found in PubMed).

Hosack DA, Dennis G JR, Sherman BT, Lane HC, Lempicki RA. Identifying biological themes within lists of genes with EASE. Genome Biol. 2003;4(10):R70. Epub Sep. 11, 2003.

Hu H, Hilton MJ, Tu X, Yu K, Ornitz DM, Long F. Sequential roles of hedgehog and Wnt signaling in osteoblast development. Development 132:49-60; 2004.

Ichioka N, Inaba M, Kushida T, Esumi T, Takahara K, Inaba K, Ogawa R, Iida H, Ikehara S. Prevention of senile osteoporosis in SAMP6 mice by intrabone marrow injection of allogeneic bone marrow cells. Stem Cells. 2002;20(6):542-51.

ISR for PCT/US03/027105 mailed May 5, 2004.
ISR for PCT/US04/028162 mailed Feb. 22, 2005.
ISR for PCT/US06/012902 mailed Jul. 7, 2008.
ISR for PCT/US06/34374 mailed Jun. 16, 2008.
ISR for PCT/US07/016309 mailed Sep. 16, 2008.
ISR for PCT/US07/05073 mailed Oct. 29, 2007.
ISR for PCT/US07/25833 mailed Sep. 11, 2008.
ISR for PCT/US08/013319 mailed Apr. 8, 2009.

Iwata H, Sakano S, Itoh T, Bauer TW. Dem ineralized bone matrix and native bone morphogenetic protein in orthopaedic surgery. Clin Orthop Relat Res. Feb. 2002;(395):99-109. Review.

Izumo N. et al.; Lipophilic statins can be osteogenic by promoting osteoblastic calcification in a Cbfal- and BMP-2-independent manner. Methods and Findings in Experimental and Clinical Pharmacology 2001, 23(7): 389-394.

Johnson ML, Harnish K, Nusse R, Van Hul W. LRP5 and Wnt signaling: a union made for bone. J Bone Miner Res. Nov. 2004;19(11):1749-57.

Jung ME, Johnson TW. First total synthesis of Zestobergesterol A and active structural analogues of the Zestobergesterol. Organic Lett 1999; 1:1671-1674.

Juvet LK, Andresen SM, Schuster GU, Dalen KT, Tobin KA, Hollung K, Haugen F, Jacinto S, Ulven SM, Bamberg K, Gustafsson JA, Nebb HI. On the role of liver X receptors in lipid accumulation in adipocytes. Mol Endocrinol. Feb. 2003;17(2):172-82.

Kadiyala et al., Culture expanded canine mesenchymal stem cells possess osteochondrogenic potential in vivo and in vitro, Cell Transplantation 1997, 6(2): 125-134.

Kametani T, Tsubuki M, Higurashi K, Honda T. J Org Chem 1986, 51: 2932-2939.

Kennell JA, MacDougald OA. Wnt signaling inhibits adipogenesis through beta-catenin-dependent and -independent mechanisms. J Biol Chem. Jun. 24, 2005;280(25):24004-10.

Kha HT, Basseri B, Shouhed D, Richardson J, Tetradis S, Hahn TJ, Parhami F. Oxysterols regulate differentiation of mesenchymal stem cells: pro-bone and anti-fat. J Bone Miner Res 19:830-840; 2004.

Kim JB, Wright HM, Wright M, Spiegelman BM. ADD1/SREBP1 activates PPARgamma through the production of endogenous ligand. Proc Natl Acad Sci U S A. Apr. 14, 1998;95(8):4333-7.

Kim WK et al.; 20(S)-hydroxycholesterol inhibits PPARgamma expression and adipogenic differentiation of bone marrow stromal cells through a hedgehog-dependent mechanism; Journal of Bone Mineral Research 2007, 22(11):1711-1719.

Komori T. Regulation of skeletal development by the Runx family of transcription factors. J Cell Biochem. Jun. 1, 2005;95(3):445-53.

Kurland ES, Cosman F, McMahon DJ, Rosen CJ, Lindsay R, Bilezikian J. Parathyroid hormone as a therapy for idiopathic osteoporosis in men: effects on bone mineral density and bone markers. J Clin End ocrinol Metab 2000; 85:3069-3076.

Lefevre A, Morera A-M, Saez JM. Adrena I cholesterol-binding protein: properties and partial purification. FEBS Letters 1978, 89(2): 287-292.

Lehmann IM, Kliewer SA, Moore LB, Smith-Oliver TA, Oliver BB, Su J, Sundseth SS, Winegar DA, Blanchard DE, Spencer TA, Willson TM. Activation of the nuclear receptor LXR by oxysterols defines a new hormone response pathway. J Biol Chem 1997; 272:3137-3140.

Li RH, Wozney JM. Delivering on the promise of bone morphogenetic proteins. Trends Biotechnol. Jul. 2001;19(7):255-65. Review.

Libby P. Inflammation in atherosclerosis. Nature 420:868-874; 2002.

Lieberman JR, Daluiski A, Einhorn TA. The role of growth factors in the repair of bone. J Bone & Joint Surg 2002; 84A:1032-1044.

Long F, Zhang XM, Karp S, Yang Y, McMahon AP. Genetic manipulation of hedgehog signaling in the endochondral skeleton reveals a direct role in the regulation of chondrocyte proliferation. Development 2001; 128:5099-5108.

Lum L, Beachy PA. The hedgehog response network: sensors, switches, and routers. Science 304:1755-1759; 2004.

Maeda T, Matsunuma A, Kawane T, Horiuchi N. Simvastatin promotes osteoblast differentiation and mineralization in MC3T3-E1 cells. Bio chem Biophys Res Commun. Jan. 26, 2001;280(3):874-7.

Maggio D, Barabani M, Pi erandrei M, Polidori MC, Catani M, Mecocci P, Senin U, Pacifici R, Cherubini A. Marked decrease in plasma antioxidants in aged osteoporotic women: results of a cross-sectional study. J Clin Endocrinol Metab. Apr. 2003;88(4):1523-7.
Majors AK, Boehm CA, Nitto H, Midura RJ, Muschler GF. Characterization of human bone marrow stromal cells with respect to osteoblastic differentiation. J Bone & Joint Surgery 1997; 15:546-557.
Makino T, Shibata K, Rohrer DC, Osawa Y. Steroid conformations in solid and solution: stereoselectivity of Grignard addition to 20-keto steroids. J. Org. Chem. 1978, 43(2): 276-280.
Manolagas SC. Cellular and molecular mechanisms of osteoporosis. Aging 1998; 10(3):182-190.
Manolagas SC. Birth and death of bone cells: basic regulatory mechanisms and implications for the pathogenesis and treatment of osteoporosis. Endocr Rev. Apr. 2000;21(2):115-37.
Mazzocchi PH, Wilson FK, Klinger L, Miniamikawa S. J Org Chem 1983, 48: 2981-2989 (no detailed info found in PubMed).
Mbalaviele G, Sheikh S, Stains JP, Salazar VS, Cheng SL, Chen D, Civitelli R. Beta-catenin and BMP-2 synergize to promote osteoblast differentiation and new bone formation. J Cell Biochem. Feb. 1, 2005;94(2):403-18.
Meaney S, Hassan M, Sakinis A, Lutjohann D, von Bergmann K, Wennmalm A, Diczfalusy U, Bjorkhem I. Evidence that the major oxysterols in human circulation originate from distinct pools of cholesterol: a stable isotope study. J Lipid Res 2001; 42:70-78.
Melton LI. How many women have osteoporosis now? J Bone Miner Res 1995; 10:175-177.
Meunier P, Aaron J, Edouard C, Vignon G. Osteoporosis and the replacement of cell populations of the marrow by adipose tissue: a quantitative study of 84 iliac bone biopsies. Clinical Orthopedics and Related Res 1971; 80:147-154.
Mezey et al., Oral Diseases 2009, Abstract.
Mitsunobu O. The use of diethyl azodicarboxylate and triphenylphosphine in syntheses and transformation of natural products. Synthesis 1981; 1-28.
Miyamoto K, Suzuki H, Yamamoto S, Saitoh Y, Ochiai E, Moritani S, Yokogawa K, Waki Y, Kasugai S, Sawanishi H, Yamagami H. Prostaglandin E2-mediated anabolic effect of a no vel inhibitor of phosphodiesterase 4, XT-611, in the in vitro bone marrow culture.J Bone Miner Res. Aug. 2003;18(8):1471-7.
Mody N, Parham i F, Sarafian TA, Demer LL. Oxidative stress modulates osteoblastic differentiation of vascular and bone cells. Free Radic Biol Med. Aug. 15, 2001;31(4):509-19.
Moerman EJ, Teng K, Lipschitz DA, Lecka-Czernik B. Aging activates adipo genic and suppresses osteogenic programs in mesenchymal marrow stroma/stem cells: the role of PPAR-gamma2 transcription factor and TGF-beta/BMP signaling pathways. Aging Cell. Dec. 2004;3(6):379-89.
Morisaki M, Sato S, Ikekawa N. Studies on steroids. XLV. Synthesis of the four stereoisomers of 20,22-dihydroxycholesterol. Chem Pharm Bull 1977; 25:2576-2583.
Mullor JL, Dahmane N, Sun T, Ruiz i Altaba A. Wnt signals are targets and mediators of Gli function. Curr Biol. May 15, 2001;11(10):769-73.
Mullor JL, Sanchez P, Altaba AR. Pathways and consequences: hedgehog signaling in human disease. Trends Cell Bio 2002; 12:562-569.
Mundy et al.; Science 1999, 286: 1946-1949.
Mundy GR. Directions of drug discovery in osteoporosis. Annu Rev Med 2002; 53;337-354.
Nagano H, Poyser JP, Cheng KP, Bang L, Ourisson G, Beck JP. Chemistry and biochemistry of Chinese drugs, Part II—Hydroxylated sterols, cytotoxic towards cancerous cells: synthesis and testing. J. Chem. Res. (S) 1977, 9: 2519-2572.
Nakamura et al., Stimulation of bone formation by intraosseous application of recombinant basic fibroblast growth factor in normal and ovariectomized rabbits, J. Orthopaedic Research 1997, 15(2): 307-313.
Office Action for U.S. Appl. No. 10/524,945 dated Mar. 23, 2009.
Office Action for U.S. Appl. No. 10/524,945 dated Jun. 11, 2008.
Office Action for U.S. Appl. No. 10/569,994 dated Jan. 2, 2009.
Office Action for U.S. Appl. No. 10/569,994 dated May 30, 2008.
Office Action for U.S. Appl. No. 10/569,994 dated Aug. 31, 2009.
Olkkonen VM, Lehto M. Oxysterols and oxysterol binding proteins: role in lipid metabolism and atherosclerosis. Ann Med 36:562-572; 2004.
Otto F, Thronell AP, Crompton T, Denzel A, Gilmour KC, Rosewell IR, Stamp GWH, Beddington RSP, Mundlos S, Olsen BR, Selby PB, Owen MJ. Cbfa1, a candidate gene for cleidocranial dysplasia syndrome, is essential for osteoblast differentiation and bone development. Cell 1997; 89:765-771.
Panakova D, Sprong H, Marois E, Thiele C, Eaton S. Lipoprotein particles are required for hedgehog and wingless signaling. Nature 435:58-65; 2005.
Parhami F, Mody N, Gharavi N, Ballard AJ, Tintut Y, Demer LL. Role of the cholesterol biosynthetic pathway in osteoblastic differentiation of marrow stromal cells. J Bone Miner Res. Nov. 2002;17(11):1997-2003.
Parish et al.; Side-chain oxysterol regulation of 3-hydroxy-3-methylglutaryl coenzyme a reductase activity. Lipids 1995, 247-251.
Peet DJ, Janowski BA, Mangelsdorf DJ. The LXRs: a new class of oxysterol receptors. Curr Opin Genetics & Develop 1998; 8:571-575.
Pittenger MF, Mackay AM Beck SC, Jaiswal RK, Douglas R, Mosca JD, Moorman MA, Simonetti DW, Craig S, Marshak DR. Multilineage potential of adult human mesenchymal stem cells. Science 1999; 284:143-147.
Poza J, Rega M, Paz V, Alonso B, Rodríguez J, Salvador N, Fernández A, Jiménez C. Synthesis and evaluation of new 6-hydroximinosteroid analogs as cytotoxic agents. Bioorg Med Chem. Jul. 15, 2007;15(14):4722-40.
Prockop DJ. Marrow stromal cells as stem cells for nonhematopoietic tissues. Science 1997; 276:71-74.
Quarto R, Thomas D, Liang CT. Bone progenitor cell deficits and the age-associated decline in bone repair capacity. Calcif Tissue Int. Feb. 1995;56(2):123-9.
Raisz LG The osteoporosis revolution. Ann Int Med 1997; 126:458-462.
Rao AS. Addition reactions with formation of carbon-oxygen bones: (1) General methods of epoxidation. Comprehensive Organic Synthesis, Pergamon Press, Eds. Trost BM, Fleming I. 1991; 7 (chapter 3.1); 376-380.
Rawadi G, Vayssiere B, Dunn F, Baron R, Roman-Roman S. BMP-2 controls alkaline phosphatase expression and osteoblast mineralization by a Wnt autocrine loop. J Bone Miner Res. Oct. 2003;18(10):1842-53.
Reeve J, Mitchell A, Tellez M, Hulme P, Green JR, Wardley-Smith B, Mitchell R. Treatm ent with parathyroid peptides and estrogen replacement for severe postmenopausal vertebral osteoporosis: prediction of long-term responses in spine and femur. J Bone Miner Res 2001; 19:102-114.
Reinholz GG, Getz B, Pederson L, Sanders ES, Subramaniam M, Ingle JN, Spelsberg TC. Bisphosphonates directly regulate cell proliferation, differentiation, and gene expression in human osteoblasts. Cancer Res. Nov. 1, 2000;60(21):6001-7.
Richardson JA et al. 2005, Characterization of osteogenic oxysterols and their molecular mechanism(s) of action, J Bone Miner Res 20:S1;S414.
Richardson JA, Amantea CM, Kianmand B, Tetradis S, Lieberman JR, Hahn TJ, Parhami F. Oxysterol-induced osteoblastic differentiation of pluripotent mesenchymal cells is mediated through a PKC- and PKA-dependent pathway. J Cell Biochem. Apr. 1, 2007;100(5):1131-45 (same as 2006 in press).
Rickard DJ, Sullivan TA, Shenker BJ, Leboy PS, Kazhdan I. Induction of rapid osteoblast differentiation in rat bone marrow stromal cell cultures by dexamethasone and BMP-2. Dev Biol. Jan. 1994;161(1):218-28.
Riggs BL, Melton LJ 3rd. The prevention and treatment of osteoporosis. N Engl J Med. Aug. 27, 1992;327(9):620-7. Review.
Riobó NA, Lu K, Ai X, Haines GM, Emerson CP Jr. Phosphoinositide 3-kinase and Akt are essential for Sonic Hedgehog signaling. Proc Natl Acad Sci U S A. Mar. 21, 2006;103(12):4505-10.
Rodan GA, Martin TJ. Therapeutic approaches to bone diseases. Science 2000; 289:1508-1514.

Rodda SJ, McMahon AP. Distinct roles for Hedgehog and canonical Wnt signaling in specification, differentiation and maintenance of osteoblast progenitors. Development. Aug. 2006;133(16):3231-44.

Ruan B, Wilson WK, Shroepfer GJ. An improved synthesis of (20R,22R)-cholest-5-ene-3β,20,22-triol, and intermediate in steroid hormone formation and an activator of nuclear orphan receptor LXRα. Steroids 1999; 64:385-395.

Rubin CD. Treatment considerations in the management of age-related osteoporosis. The American J Medical Sciences 1999; 318 (3):158-170.

Russell DW. Oxysterol biosynthetic enzymes. Biochimica et B iophysica Acta 2000; 1529:126-135.

Sammons J, Ahmed N, El-Sheemy M, Hassan HT. The role of BMP-6, IL-6, and BMP-4 in mesenchymal stem cell-dependent bone development: effects on osteoblastic differentiation induced by parathyroid hormone and vitamin D3. Stem Cells and Development 2004, 13: 273-280.

Sanchez P, Hernandez AM, Stecca B, Kahler AJ, DeGueme AM, Barrett A, Beyna M, Datta MW, Datta S, Ruiz i Altaba A. Inhibition of prostate cancer proliferation by interference with Sonic Hedgehog-GLI1 signaling. Proc Natl Acad Sci U S A. Aug. 24, 2004;101(34):12561-6.

Sang et al.; Ectopic overexpression of adipogenic transcription factors induces transdifferentiation of MC3T3-E1 osteoblasts. Biochemical and Biophysical Research Communications 2005, 327(3): 811-819.

Schaafsma et al. 2001. Delay of natural bone loss by higher intake of specific minerals and vitamins. Crit Rev Food Sci Nutr 41:225-249.

Schambony A, Wedlich D. Wnt-5A/Ror2 regulate expression of XPAPC through an alternative noncanonical signaling pathway. Dev Cell. May 2007;12(5):779-92.

Schroepfer GJ Jr. Oxysterols: modulators of cholesterol metabolism and other processes. Physiol Rev. Jan. 2000;80(1):361-554. Review.

Seo JB, Moon HM, Kim WS, Lee YS, Jeong HW, Yoo EJ, Ham J, Kang H, Park MG, Steffensen KR, Stulnig TM, Gustafsson JA, Park SD, Kim JB. Activated liver X receptors stimulate adipocyte differentiation through induction of peroxisome proliferator-activated receptor gamma expression. Mol Cell Biol. Apr. 2004;24(8):3430-44.

Shea CM, Edgar CM, Einhorn TA, Gerstenfeld LC. BMP treatment of C3H10T1/2 mesenchymal stem cells induces both chondrogenesis and osteogenesis. J Cell Biochem. Dec. 15, 2003;90(6):1112-27.

Shimaoka H, Dohi Y, Ohgushi H, Ikeuchi M, Okamoto M, Kudo A, Kirita T, Yonemasu K. Recombinant growth/differentiation factor-5 (GDF-5) stimulates osteogenic differentiation of marrow mesenchymal stem cells in porous hydroxyapatite ceramic. J Biomed Mater Res A. Jan. 1, 2004;68(1):168-76.

Shouhed D, Kha HT, Richardson JA, Amantea CM, Hahn TJ, Parhami F. Osteogenic oxysterols inhibit the adverse effects of oxidative stress on osteogenic differentiation of marrow stromal cells. J Cell Biochem 95:1276-1283; 2005.

Silva-Vargas V, Lo Celso C, Giangreco A, Ofstad T, Prowse DM, Braun KM, Watt FM. Beta-catenin and Hedgehog signal strength can specify number and location of hair follicles in adult epidermis without recruitment of bulge stem cells. Dev Cell. Jul. 2005;9(1):121-31.

Sohal RS, Mockett RJ, Orr WC. Mechanisms of aging: an appraisal of the oxidative stress hypothesis. Free Radic Bio l Med. Sep. 1, 2002;33(5):575-86. Review.

Song et al., Chinese Journal of Reparative and Reconstructive Surgery 2002, 16: 384-387.

Spinella-Jaegle S, Rawadi G, Kawai S, Gallea S, Faucheu C, Mollat P, Courtois B, Bergaud B, Ramez V, Blanchet AM, Adelmant G, Baron R, Roman-Roman S. Sonic hedgehog increases the commitment of pluripotent mesenchymal cells into the osteoblastic lineage and abolishes adipocytic differentiation. J Cell Sci 114:2085-2094; 2001.

Spiro RC, Thompson AY, Poser JW. Spinal fusion with recombinant human growth and differentiation factor-5 combined with a mineralized collagen matrix. Anat Rec. Aug. 1, 2001;263(4):388-95.

Stein GS, Lian JB. Molecular mechanisms mediating proliferation/differentiation interrelationships during progressive development of the osteoblast phenotype. Endocrine Rev 14:424-442; 1993.

Stewart GA, Hoyne GF, Ahmad SA, Jarman E, Wallace WA, Harrison DJ, Haslett C, Lamb JR, Howie SE. Expression of the developmental Sonic hedgehog (Shh) signalling pathway is up-regulated in chronic lung fibrosis and the Shh receptor patched1 is present in circulating T lymphocytes. J Pathol 199:488-495; 2003.

St-Jacques B, Hammerschmidt M, McMahon P. Indian hedgehog signaling regulates proliferation and differentiation of chondrocytes and is essential for bone formation. Genes Dev 1999; 13:2072-2086.

Suh JM, Gao X, McKay J, McKay R, Salo Z, Graff JM. Hedgehog signaling plays a conserved role in inhibiting fat formation. Cell Metab. Jan. 2006;3(1):25-34.

Swarthout JT, D'Alonzo RC, Selvamurugan N, Partridge NC. Parathyroid hormone-dependent signaling pathways regulating genes in bone cells. Gene. Jan. 9, 2002;282(1-2):1-17. Review.

Taipale J, Beachy PA. The Hedgehog and Wnt signalling pathways in cancer. Nature. May 17, 2001;411(6835):349-54. Review.

Taylor FR, Kandutsch AA, Gayen AK, Nelson JA, Nelson SS, Phirwa S, Spencer TA. 24,25-Epoxysterol metabolism in cultured mammalian cells and repression of 3-hydroxy-3-methylglutaryl-CoA reductase. J Biol Chem. Nov. 15, 1986;261(32):15039-44.

Thies RS, Bauduy M, Ashton BA, Kurtzberg L, Wozney JM, Rosen V. Recombinant human bone morphogenetic protein-2 induces osteoblastic differentiation in W-20-17 stromal cells. Endocrinology 1992, 130(3): 1318-1324.

Väänänen HK. Mesenchymal stem cells. Ann Med. 2005;37(7):469-79. Review.

Valentin-Opran A, Wozney J, Csim ma C, Lilly L, Riedel GE. Clinical evaluation of recombinant human bone morphogenetic protein-2. Clin Orthop & Related Res 2002; 305:110-120.

Velgova H, Cerny V, Sorm F, Slama K. Collect. Czech. Chem. Commun. 1969, 34: 3354-3375.

Viccica et al.; Role of the cholesterol biosynthetic pathway in osteoblastic differentiation. J. Endocrinol. Invest. 2007, 30(6S): 8-12.

Vine DF, Mamo JCL, Beilin LJ, Mori TA, Croft KD. Dietary oxysterols are incorporated in plasma triglyceride-rich lipoproteins, incrase their susceptibility to oxidation and increase aortic cholesterol concentrations in rabbits. J Lipid Res 1998; 1995-2004.

Wang GJ, Cui Q, Balian G. The Nicolas Andry award. The pathogenesis and prevention of steroid-induced osteonecrosis. Clin Orthop Relat Res. Jan. 2000;(370):295-310.

Watson KE, Bostrom K, Ravindranath R, Lam T, Norton B, Demer LL. TGF-beta and 25-hydroxycholesterol stimulate osteoblast-like vascular cells to calcify. J Clin Invest 93:2106-2113; 1994.

Westendorf JJ, Kahler RA, Schroeder TM. nt signaling in osteoblasts and bone diseases. ene. Oct. 27, 2004;341:19-39. Review.

Wiersig JR, Waespe-Sarcevic N, Djerassi C. Stereospecific synthesis of the side chain of the steroidal plant sex hormone oogoniol. J. Org. Chem. 1979, 44(19): 3374-3382.

Woo BH, Fink BF, Page R, Schrier JA, Jo YW, Jiang G, DeLuca M, Vasconez HC, DeLuca PP. Enhancement of bone growth by sustained delivery of recombinant human bone morphogenetic protein-2 in a polymeric matrix. Pharm Res 2001; 18:1747-1753.

Written Opinion for PCT/US04/028162 mailed Feb. 22, 2005.
Written Opinion for PCT/US06/012902 mailed Jul. 7, 2008.
Written Opinion for PCT/US06/34374 mailed Jun. 16, 2008.
Written Opinion for PCT/US07/016309 mailed Sep. 16, 2008.
Written Opinion for PCT/US07/05073 mailed Oct. 29, 2007.
Written Opinion for PCT/US08/013319 mailed Apr. 8, 2009.

Yamaguchi A, Komori T, Suda T. Regulation of osteoblast differentiation mediated by bone morphogenetic proteins, hedgehogs, and Cbfal. Endocrine Rev 2000; 21:393-411.

Yang D, Guo J, Divieti P, Bringhurst FR. Parathyroid hormone activates PKC-delta and regulates osteoblastic differentiation via a PLC-independent pathway. Bone. Apr. 2006;38(4):485-96. Epub Dec. 1, 2005.

Yang X, Karsenty G. Transcription factors in bone: developmental and pathological aspects. Trends Mol Med. Jul. 2002;8(7):340-5. Review.

Yeh et al., Journal of Cell Biochemistry 2002, 87: 292-304.

Yoon ST, Boden SD. Osteoinductive molecules in orthopaedics: basic scie nce and preclinical studies. Clin Orthop & Related Res 2002; 495:33-43.

Yoshida CA, Furuichi T, Fujita T, Fukuyama R, Kanatani N, Kobayashi S, Satake M, Takada K, Komori T. Core-binding factor beta interacts with Runx2 and is required for skeletal development. Nat Genet. Dec. 2002;32(4):633-8.

Yoshida K, Oida H, Kobayashi T, Maruyama T, Tanaka M, Katayama T, Yamaguchi K, Segi E, Tsuboyama T, Matsushita M, Ito K, Ito Y, Sugimoto Y, Ushikubi F, Ohuchida S, Kondo K, Nakamura T, Narumiya S. Stimulation of bone formation and prevention of bone loss by prostaglandin E EP4 receptor activation. Proc Natl Acad Sci U S A. Apr. 2, 2002;99(7):4580-5. Epub Mar. 26, 2002 (auth or typo: Yoshia).

Zanchetta P, Lagar de N, Guezennec J. Systematic effects on bone healing of a new hyaluronic acid-like bacterial exopolysaccharide. Calcif Tissue Int 2003; 73:232-236.

Zelcer N, Tontonz P. Liver X receptors as integrators of metabolic and inflammatory signaling. J Clin Invest 116:607-614; 2006.

Zhang et al., Cyclooxygenase-2 regulates mesenchymal cell differentiation into the osteoblast lineage and is critically involved in bone repair, J. Clinical Investigation 2002, 109(11): 1405-1415.

Zhao M, Qiao M, Harris SE, Chen D, Oyajobi BO, Mundy GR. The zinc finger transcription factor Gli2 mediates bone morphogenetic protein 2 expression in osteoblasts in response to hedgehog signaling. Mol Cell Biol 26:6197-6208; 2006.

Zhao M, Qiao M, Oyajobi BO, Mundy GR, Chen D. E3 ubiquitin ligase Smurf1 mediates core-binding factor alpha1/Runx2 degradation and plays a specific role in osteoblast differentiation. J Biol Chem. Jul. 25, 2003;278(30):27939-44.

Ziros PG, Gil AP, Georgakopoulos T, Habeos I, Kletsas D, Basdra EK, Papavassiliou AG. The bone-specific transcriptional regulator Cbfa1 is a target of mechanical signals in osteoblastic cells. J Biol Chem. Jun. 28, 2002;277(26):23934-41.

Albrektsson T., Johansson C. Osteoinduction, osteoconduction and osseointegration. 2001. Eur Spine J. 10:S96-S101.

Dimmeler et al. HMG-CoA reductase inhibitors (statins) increase endothelial progenitor cells via the PI 3-kinase/Akt pathway. 2001. Journal of Clin Invest. 108:(3): 391-397.

Rao et al. Lovastatin-mediated G1 arrest is through inhibition of the proteosome, independent of hydroxymethyl glutarl-CoA reductase. 1997. Proc. Natl. Acad. Sci. 96: 7797-7802.

Steitz et al. Smooth Muscle Cell Phenotypic Transition Associated With Calcification: Upregulation of Cbfa1 and Downregulation of Smooth Muscle Lineage Markers. 2001. Circ. Res. 89:1147-1154.

Tintut et al. Multilineage Potential of Cells From the Artery Wall. 2003. Circulation.108: 2505-2510.

Wada et al. Calcification of Vascular Smooth Muscle Cell Cultures : Inhibition by Osteopontin. 1999. Circ. Res. 8:166-178.

Wada et al. Lack of Positive Correlation Between Statin Ue and Bone Mineral Density in Japanese Subjects With Type 2 Diabetes. 2000. Arch Intern Med. 160:2865.

Wang et al. Lipid Clearing Agents in Steroid-Induces Osteoporosis. 1995. J Formos Med Assoc. 94(10): 589-592.

Kim W et al. Osteogenic oxysterol, 20(S)- Hydroxycholesterol, inhibits PPAR gamma expression and adipogenic differentioation of bone marrow stromal cells through s hedgehog-, wnt-, and MAPK-Dependent Mechanism. J Bone Miner Res. 2006. 21(1): S394.

Nagano et al., "Chemistry and Biochemistry of Chinese Drugs, Part II. Hydroxylated Sterols, Cytotoxic toward Cancerous Cells: Synthesis and Testing," J. Chem Research, Apr. 1977, pp. 2522-2571 (with English-language synopsis).

INHIBITION OF PPAR GAMMA EXPRESSION BY SPECIFIC OSTEOGENIC OXYSTEROLS

CROSS REFERENCE TO RELATED APPLICATIONS

This application is a U.S. National Stage Application of International Application No. PCT/US2007/025833, filed Dec. 19, 2007, and claims the benefit of the filing date of U.S. provisional application 60/875,913, filed Dec. 19, 2006, the entire contents of each of which are incorporated by reference herein.

The invention was made with Government support of Grant No. AR050426 awarded by the National Institutes of Health. The government has certain rights in this invention.

BACKGROUND

Oxysterols form a large family of oxygenated derivatives of cholesterol that are present in the circulation, and in human and animal tissues. Oxysterols that have been identified in human plasma to date include 7α-hydroxycholesterol, 24S-hydroxycholesterol, and 4α- and 4β-hydroxycholesterol, which are present at concentrations ranging from 5-500 ng/ml. These oxysterols have a variety of half-lives in circulation ranging from 0.5-60 hours, and their levels can be altered by aging, drug interventions, and disease processes. Oxysterols may be formed either by autooxidation, as a secondary byproduct of lipid peroxidation, or by the action of specific monooxygenases, most of which are members of the cytochrome P450 family of enzymes. Examples of these enzymes are cholesterol 7α-hydroxylase (CYP7A1) that forms 7α-hydroxycholesterol, cholesterol 25-hydroxylase that forms 25-hydroxycholesterol, cholesterol 24S-hydroxylase (CYP46) that forms 24S-hydroxycholesterol, and others. In addition, oxysterols may be derived from the diet. Cytochrome P450 enzymes are also involved in the further oxidation of oxysterols and their metabolism into active or inactive metabolites that leads to their eventual removal from the system. Certain oxysterols have potent effects on cholesterol metabolism. In addition, the presence of oxysterols in atherosclerotic lesions has prompted studies of their potential role in the pathogenesis of this disorder. A role for specific oxysterols has been implicated in various physiologic processes including cellular differentiation, inflammation, apoptosis, and steroid production.

Recently, several reports have noted the possible role of oxysterols in cellular differentiation. Specific oxysterols induce the differentiation of human keratinocytes in vitro, while monocyte differentiation can be induced by the oxysterol 7-ketocholesterol. Our previous reports have shown that specific oxysterols induce the differentiation of pluripotent mesenchymal cells into osteoblastic cells, while inhibiting their differentiation into adipocytes. Differentiation of keratinocytes by oxysterols is mediated by the nuclear hormone receptor, liver X receptor β (LXRβ). LXRα and LXRβ, initially identified as orphan nuclear receptors, act as receptors for oxysterols. However many of the effects of oxysterols are mediated by LXR-independent mechanisms. These include their effects on mesenchymal cells, since activation of LXR by specific LXR ligands inhibited, rather than stimulated, the osteogenic differentiation of mesenchymal cells. Furthermore, marrow stromal cells (MSCs) derived from LXR null mice were able to respond to osteogenic oxysterols as well as their wild type counterparts. Additional oxysterol binding proteins have been reported that can regulate the activity of signaling molecules such as mitogen-activated protein kinase (MAPK).

Hedgehog molecules have been shown to play key roles in a variety of processes including tissue patterning, mitogenesis, morphogenesis, cellular differentiation and embryonic developments. In addition to its role in embryonic development, hedgehog signaling plays a crucial role in postnatal development and maintenance of tissue/organ integrity and function. Studies using genetically engineered mice have demonstrated that hedgehog signaling is important during skeletogenesis as well as in the development of osteoblasts in vitro and in vivo. In addition to playing a pro-osteogenic role, hedgehog signaling also inhibits adipogenesis when applied to pluripotent mesenchymal cells, C3H-10T 1/2.

Hedgehog signaling involves a very complex network of signaling molecules that includes plasma membrane proteins, kinases, phosphatases, and factors that facilitate the shuffling and distribution of hedgehog molecules. Production of hedgehog molecules from a subset of producing/signaling cells involves its synthesis, autoprocessing and lipid modification. Lipid modification of hedgehog, which appears to be essential for its functionality, involves the addition of a cholesterol molecule to the C-terminal domain of the autocleaved hedgehog molecule and palmitoylation at its N-terminal domain. Additional accessory factors help shuttle hedgehog molecules to the plasma membrane of the signaling cells, release them into the extracellular environment, and transport them to the responding cells.

In the absence of hedgehog molecules, Patched (Ptch), present on the plasma membrane of the responding cells, keeps hedgehog signaling in a silent mode by inhibiting the activity of another plasma membrane associated signal transducer molecule, Smoothened (Smo). In the presence of hedgehog, the inhibition of Smo by Ptch is alleviated and Smo transduces the signal for the regulation of transcription of hedgehog-regulated genes. This transcriptional regulation in part involves the Ci/Gli transcription factors that enter the nucleus from the cytoplasm after a very intricate interaction between the members of a complex of accessory molecules that regulate Gli and its conversion from a 75 kd transcriptional repressor to a 155 kd transcriptional activator. The details of this highly complex signaling network have been extensively reviewed. (Cohen (2003) *Am J Med Gen* 123A, 5-28; Mullor et al. (2002) *Trends Cell Bio* 12, 562-569).

SUMMARY

In a method for inhibiting expression of a peroxisome proliferator activated receptor (PPAR) in a cell, at least one oxysterol compound is contacted with the cell in an amount effective to inhibit expression of the PPAR, and inhibition of expression of the PPAR is measured. The PPAR can be PPAR gamma. The oxysterol compound can be, for example, 20(S)-hydroxycholesterol, 22(R)-hydroxycholesterol, 22(S)-hydroxycholesterol, 25-hydroxycholesterol, 25(S)-hydroxycholesterol, 5-cholesten-3-beta-20-alpha-diol-3-acetate, 24-hydroxycholesterol, 24(S)-hydroxycholesterol, 24(S),25-epoxycholesterol, 26-hydroxycholesterol, 4-beta-hydroxycholesterol, pregnanolone, Oxy 11

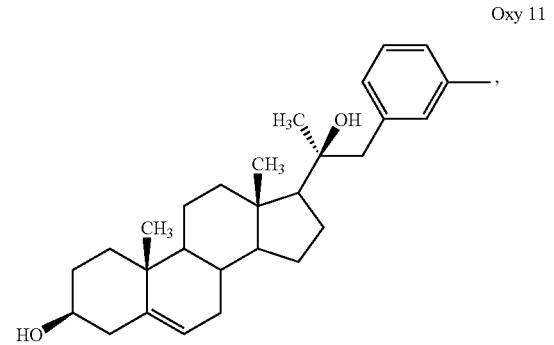

Oxy12

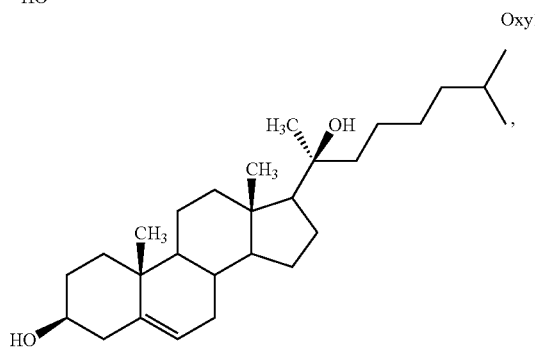

Oxy13

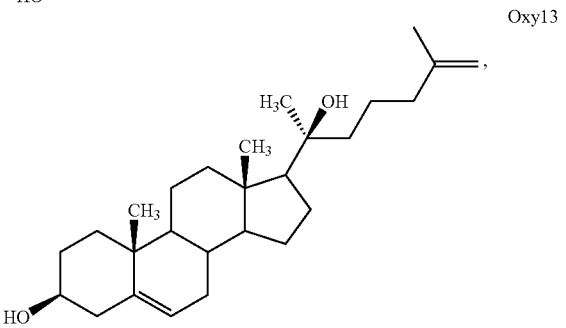

Oxy14

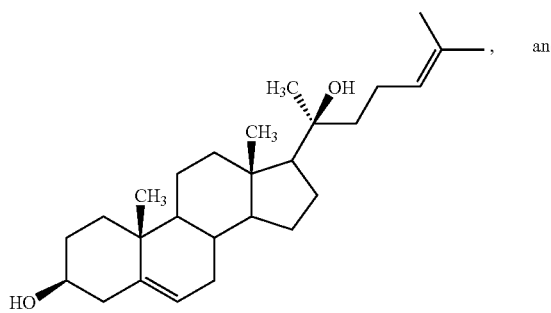

and

Oxy16

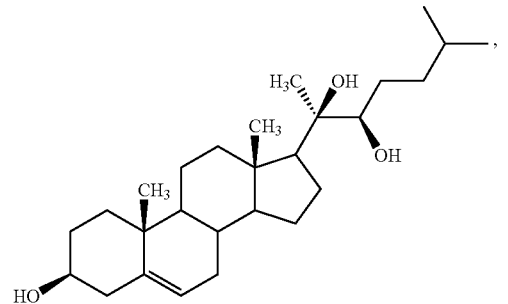

analogs thereof, derivatives thereof, and combinations thereof.

The expression of PPAR in the cell can be inhibited relative to a baseline value. For example, this baseline value can be the level of PPAR expression associated with cells in a culture stimulated to express PPAR, e.g., cells stimulated to express PPAR by Tro. As another example, this baseline value can be the level of PPAR expression in a sick patient associated with a pathology prior to treatment with an oxysterol compound to reduce expression to a lower, e.g., healthier level. As another example, this baseline value can be the level of PPAR expression associated with another reference condition of a cell.

A method of treating or preventing a condition associated with increased adipogenesis in a subject includes administering to the subject an amount of an oxysterol compound effective to treat or prevent the condition, wherein the oxysterol compound inhibits PPAR expression. For example, the oxysterol compound can be administered systemically or locally to a target tissue of interest. The condition can be, for example, obesity, osteoporosis, diabetes, muscular atrophy, or aging.

A method of treating or preventing a condition associated with excessive accumulation of intracellular and/or extracellular fats and/or lipids in a subject includes administering to the subject an amount of an oxysterol compound effective to treat or prevent the condition, wherein the oxysterol compound inhibits PPAR expression. For example, the oxysterol compound can be administered systemically or locally to a target tissue of interest. The condition can be, for example, xanthoma formation.

A method includes selecting a subject having a PPAR expression related condition, and administering to the subject an amount of an oxysterol compound effective to reduce the expression of PPAR.

In an embodiment, a kit includes a dosage form of a pharmaceutical composition comprising an oxysterol compound effective to inhibit expression of PPAR in a container. In another embodiment, a kit includes 20(S)-hydroxycholesterol, Oxy 11

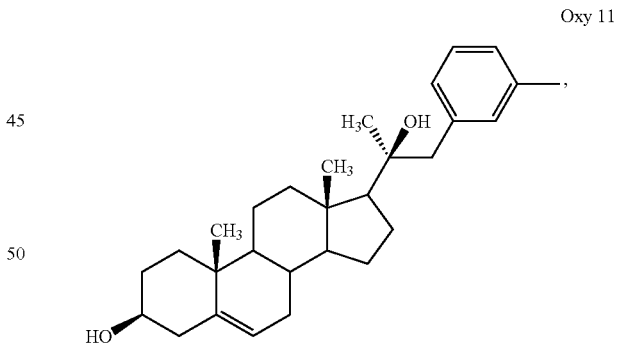

Oxy 12

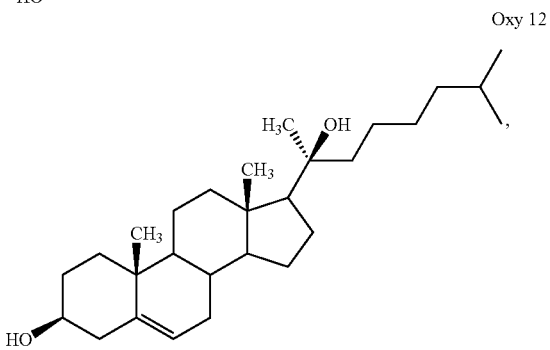

-continued

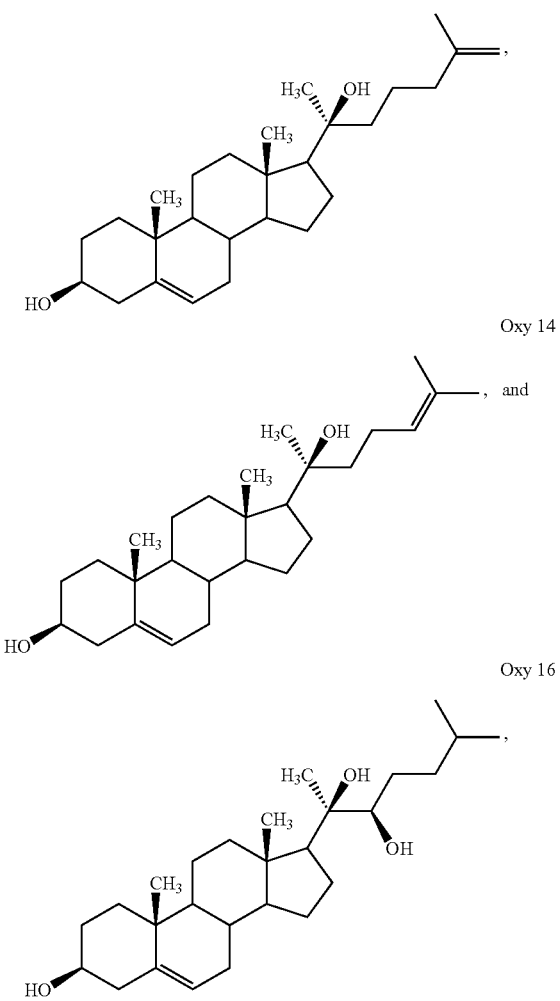

22(R)-hydroxycholesterol, 22(S)-hydroxycholesterol, 25-hydroxycholesterol, 25(S)-hydroxycholesterol, 5-cholesten-3-beta-20-alpha-diol-3-acetate, 24-hydroxycholesterol, 24(S)-hydroxycholesterol, 24(S),25-epoxycholesterol, 26-hydroxycholesterol, 4-beta-hydroxycholesterol, or pregnanolone or combinations of any of these. The kit can include a label indicating use in treating or preventing obesity, osteoporosis, diabetes, muscular atrophy, aging, or xanthoma formation in an animal or a human.

A method for identifying an oxysterol compound that inhibits expression of PPAR includes screening a candidate oxysterol compound for the ability to inhibit expression of PPAR in an in vitro assay, and selecting a candidate oxysterol compound that measurably inhibits PPAR expression.

BRIEF DESCRIPTION OF THE FIGURES

FIG. 2A: after 24 hours. FIG. 2B: after 48 hours. FIG. 2C: after 96 hours.

FIG. 3A: after 24 hours. FIG. 3B: after 48 hours. FIG. 3C: after 96 hours.

FIG. 4A: after 24 hours. FIG. 4B: after 48 hours. FIG. 4C: after 96 hours.

FIG. 5A: M2 cells transfected with PPRE-TK-LUC or pTK-LUC and pTK-Renilla-Luciferase plasmid. FIG. 5B: M2 cells transfected with PPRE-TK-LUC or pTK-LUC and CMX PPARγ expression plasmid and pTK-Renilla-Luciferase plasmid. FIG. 5C: M2 cells transfected with PPRE-TK-LUC or pTK-LUC and CMX PPARγ expression plasmid and pTK-Renilla-Luciferase plasmid.

DETAILED DESCRIPTION

Figure 1A:
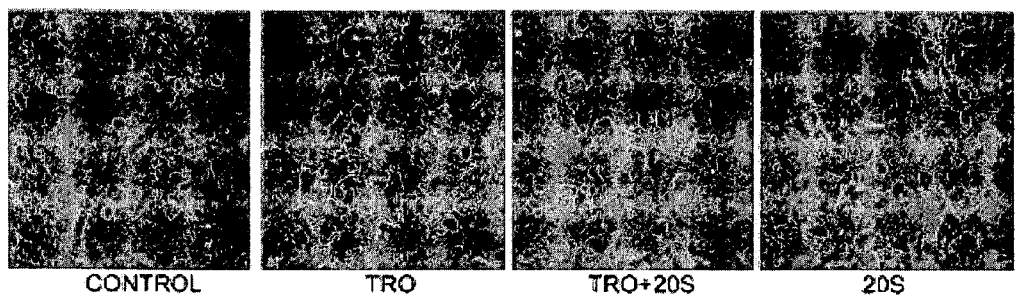
FIG. 1A presents images of M2 cells after various treatments.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the spirit and scope of the invention. All references cited herein are incorporated by reference as if each had been individually incorporated.

Age-related bone loss is associated with a progressive decrease in bone formation and an increase in adipogenesis in the bone marrow, increasing the risk of bone fractures. Multipotent bone marrow stromal cells (MSCs) are common progenitors of osteoblasts and adipocytes, and a potential reciprocal relationship between osteogenic and adipogenic differentiation of MSC has been suggested. Furthermore, an increase in adipose tissue volume and a decrease in trabecular bone volume in bone marrow has been observed with aging and in patients with osteoporosis. However, the molecular mechanisms underlying the reciprocal relationship between osteogenic and adipogenic differentiation during aging and pathological states are not well understood.

Peroxisome proliferator-activated receptor γ (PPARγ) is a member of the nuclear hormone receptor superfamily and a key regulator of adipogenic differentiation. In early adipogenic differentiation, CCAAT/enhancer-binding protein a (C/EBPβ) and C/EBPδ induce the expression of PPARγ and C/EBPα. PPARγ and C/EBPα regulate each other's expression through a positive feedback mechanism and induce other adipogenic genes that establish terminal adipogenic differentiation. PPARγ consists of two protein isoforms produced by alternative promoter use and splicing. PPARγ1 is expressed at low levels in many tissues, whereas PPARγ2 is expressed at high levels in adipose tissue. The introduction of PPARγ2 into fibroblastic cells using retroviral infection stimulates adipocyte differentiation, whereas PPARγ null embryonic stem (ES) cells fail to differentiate into adipocytes.

PPARγ inhibition can induce a shift in marrow stromal cell (MSC) differentiation from the adipogenic to the osteogenic pathway. Oxysterols can be used to shift MSC differentiation pathways. Oxysterols, a large family of 27-carbon oxygenated products of cholesterol, are present in the circulation and in human and animal tissues, and can be formed from cholesterol by either enzymatic or nonenzymatic oxidation. Oxysterols have been identified as bioactive compounds involved in various biological and pathological processes, such as cholesterol efflux, lipoprotein metabolism, calcium uptake, cell differentiation, atherosclerosis, and apoptosis. We previously reported that specific oxysterols including 20(S)-hydroxycholesterol (20S) induce osteoblastic differentiation markers, such as alkaline phosphatase activity, osteocalcin expression, and matrix mineralization in murine M2-10B4 (M2) MSCs. See, Kha H T et al, 2004 Oxysterols regulate differentiation of mesenchymal stem cells: Pro-bone and anti-fat, J Bone Miner Res 19:830-840; Richardson J A et al. 2007 Oxysterol-induced osteoblastic differentiation of pluripotent mesenchymal cells is mediated through a PKC- and PKA-dependent pathway, J Cell Biochem 100:1131-1145. Furthermore, the osteogenic oxysterols inhibit adipocyte formation and the expression of adipogenic differentiation marker genes, such as lipoprotein lipase (LPL) and adipocyte-specific fatty acid binding protein 2 (ap2). See, Kha H T et al, 2004 Oxysterols regulate differentiation of mesenchymal stem cells: Pro-bone and anti-fat, J Bone Miner Res 19:830-840. Recently, we reported that oxysterols are novel activators of the hedgehog signaling pathway. See, Dwyer J R et al. 2007 Oxysterols are novel activators of the hedgehog signaling pathway in pluripotent mesenchymal cells, J Biol Chem 282:8959-8968. Inhibitory effects of oxysterols on adipogenic differentiation of MSCs may be mediated by hedgehog signaling.

Because 20S is a naturally occurring osteogenic oxysterol that we have identified, in this study we further investigated the molecular mechanisms by which it inhibits adipogenic differentiation of MSCs. We found that similar to sonic hedgehog (Shh), 20S inhibited PPARγ mRNA expression induced by the thiazolidinedione, troglitazone (Tro), which stimulates adipogenesis by activating PPARγ. The inhibitory effects of 20S and Shh on PPARγ expression were completely blocked by the hedgehog signaling inhibitor, cyclopamine. Furthermore, 20S and Shh significantly inhibited PPARγ promoter activity induced by C/EBPα overexpression. However, 20S did not inhibit the transcriptional activity of PPARγ. This suggests that the inhibition of adipogenesis by 20S may be mediated predominantly through a hedgehog pathway-dependent mechanism(s).

Increased adipogenesis is associated with a variety of conditions including obesity, osteoporosis, and xanthoma formation. The transcription factor peroxisome proliferator activated receptor gamma (PPARγ) is understood to control the expression of target genes that allow for the formation of adipocytes. Therefore PPARγ antagonists have the potential to have clinical potential for the treatment of conditions associated with increased adipogenesis. For example, PPARγ antagonists have potential as combined anti-obesity and anti-diabetic drugs. Few molecules have been heretofore been shown to inhibit the expression of PPARγ. Compounds reported as having PPARγ antagonistic activity include the following: SR202, Oxazole, Tesaglitazar (by AstraZeneca), compounds 501516 and 590735 (by GlaxoSmithKline), T0070907 (Cayman Chemical), bisphenol A diglycidylether (BADGE). To our knowledge, none of these compounds belongs to the oxysterol class of molecules.

This application presents certain oxysterols that can inhibit the expression of PPARγ. For example, oxysterols that activate the hedgehog signaling pathway and that have osteogenic and anti-adipogenic properties can inhibit the expression of PPARγ. Osteogenic oxysterols can inhibit the mRNA expression of PPARγ. Such inhibition can be useful for controlling the dysregulated differentiation of cells into adipocytes. Oxysterol molecules effective in inhibiting PPARγ expression, analogs of these molecules, and/or active regions of these molecules, alone or as a part of a large molecule, e.g. a carrier molecule, can be systemically or locally administered to a subject to inhibit PPARγ expression in a target tissue of interest, for example, to decrease differentiation of cells into adipocytes.

Thus, adipogenesis is associated with increased expression of PPARγ and its target genes, adipocyte protein 2 (aP2) and lipoprotein lipase (LPL). The osteogenic oxysterol 20(S)-hydroxycholesterol (20S) inhibits the mRNA expression of PPARγ in marrow stromal cells (MSC). The inhibition is at the level of mRNA expression: 20S does not inhibit the transcriptional activity of exogenous PPARγ when expressed in cells using an artificial expression vector. Therefore, inhibition appears to be at a transcriptional level. Because of the association of expression of PPARγ with adipogenesis, oxysterols exhibiting anti-adipogenic and osteogenic characteristics, in addition to 20(S)-hydroxycholesterol (20S), can similarly inhibit the expression and/or activity of PPARγ in marrow stromal cells and other cell types. Furthermore, natural and synthetic analogs and molecules incorporating active portions of such anti-adipogenic and osteogenic oxysterols are expected to similarly inhibit the expression and/or activity of PPARγ in marrow stromal cells and other cell types. Oxysterols exhibiting anti-adipogenic and osteogenic characteristics, their natural and synthetic analogs, and molecules incorporating active portions of anti-adipogenic and osteogenic oxysterols can also modulate the expression and/or activity of other members of the PPAR family of proteins, including but not limited to PPARα and PPARδ (also known as PPARγ).

Because of the association of expression of PPARγ with adipogenesis, the discovery that certain oxysterol compounds exhibit anti-adipogenic and osteogenic characteristics leads to the possibility of using oxysterol compounds in addition to 20(S)-hydroxycholesterol (20S) that can similarly inhibit the expression and/or activity of PPARγ in marrow stromal cells (MSCs) and other cell types. Furthermore, natural and synthetic analogs and molecules incorporating active portions of such anti-adipogenic and osteogenic oxysterols can similarly inhibit the expression and/or activity of PPARγ in marrow stromal cells and other cell types. Oxysterols exhibiting anti-adipogenic and osteogenic characteristics, their natural and synthetic analogs, and molecules incorporating active portions of anti-adipogenic and osteogenic oxysterols can further modulate the expression and/or activity of other members of the PPAR family of proteins, including but not limited to PPARα and PPARδ (also known as PPARβ). Such oxysterol compounds can be identified by measuring their effect in vitro or in other assays of PPAR expression or activity, as taught in this application.

For example, anti-adipogenic oxysterols, oxysterol analogs, or active portions of oxysterols can be administered to cells, such as cells in vitro or in a human or animal subject to be treated, in an amount effective to inhibit a PPAR mediated response in the cell. For example, anti-adipogenic oxysterols can be administered to control the dysregulated differentiation of a cell into an adipocyte. For example, anti-adipogenic oxysterols can be administered to a human or animal subject to be treated to treat or prevent diseases and disorders associated with PPAR over-expression, including dysregulated and excessive accumulation of intracellular and/or extracellular fats and/or lipids and/or excessive adipogenesis. For example, anti-adipogenic oxysterols can be administered to treat or prevent diseases and disorders such as obesity, osteoporosis, diabetes, muscular atrophy, aging, and/or xanthoma formation in an animal or a human.

Thus, in a method according to the invention, PPAR expression inhibiting oxysterol compounds can be administered to treat a physiological and/or pathological condition in which PPAR is a key regulator and target for intervention, for the treatment of a human or animal disease.

A subject can be selected for treatment by administration of PPAR expression inhibiting oxysterol compounds (oxysterols, oxysterol analogs, or active portions of oxysterols), for example, where on the basis of the subject having a condition, disease, or disorder related to PPAR expression, (otherwise referred to as a PPAR expression related condition) on the basis of the subject having a measured abnormal level of PPAR expression, for example, systemically, in a region of tissue, or in cells, or on the basis of other diagnostic tests. During a course of treatment by administration of anti-adipogenic oxysterol compounds (e.g., oxysterols, oxysterol analogs, or active portions of oxysterols), the treatment can be modified, for example, a dosage can be increased or decreased or terminated if the subject's measured level of PPAR protein expression moves into a normal range, as determined systemically, in a region of tissue, or in cells, or on the basis of other diagnostic tests, such as inhibition of adipogenesis or serum markers indicative of adipogenesis including, but not limited to, adiponectin, leptin, and triglycerides. Thus, a PPAR expression related condition can be identified in a subject by measuring an abnormal level of PPAR expression and/or fat cell formation in the adipose tissue, as well as non-adipose tissues including, but not limited to, bone, bone marrow, skeletal muscle, and organs, such as the liver, heart, and kidney, and the oxysterol compounds of the invention can be administered to the subject to bring the level into a normal range. PPAR expression can be measured directly, for example, in an in vitro study or in a cell culture obtained by biopsy of a tissue of interest in an animal or a human subject. PPAR expression can be measured indirectly, for example, in a non-invasive procedure, such as through an X-ray of an animal or a human subject and/or analysis of symptoms and/or indications by a medical practitioner. For example, an X-ray may indicate excessive fat in a tissue, which may indicate overexpression of PPAR. The PPAR expression related conditions may be, for example, obesity, osteoporosis, diabetes, muscular atrophy, aging, and other conditions associated with increased adipogenesis, as well as xanthoma formation and other conditions associated with dysregulated and excessive accumulation of intracellular and/or extracellular fats and/or lipids.

A kit can include an oxysterol, such as an anti-adipogenic oxysterol, effective to inhibit expression of a PPAR protein. The oxysterol can be included in a pharmaceutical composition. The kit can include a label indicating use in treating and/or preventing a condition, disease, or disorder, such as obesity, osteoporosis, diabetes, muscular atrophy, aging, or xanthoma formation in a subject, such as an animal or a human.

In a method of the present invention, a candidate oxysterol, oxysterol analog, or active portion of an oxysterol is screened for the ability to inhibit expression of a PPAR protein in an in vitro assay. A candidate oxysterol, oxysterol analog, or active portion of an oxysterol can be selected that inhibits PPAR expression. The candidate oxysterol, oxysterol analog, or active portion of an oxysterol screened and/or selected can be a compound that has not previously been isolated, purified, or synthesized, or can be a compound that has not previously been recognized as having hedgehog activating, anti-adipogenic, and/or osteogenic characteristics. For example, the candidate oxysterol, oxysterol analog, or active portion of an oxysterol screened and/or selected can be other than 5-cholesten-3-beta-20-alpha-diol-3-acetate, 4-β-hydroxycholesterol, 7-ketocholesterol, 7-ketohydroxycholesterol, 7α-hydroxycholesterol, 20(S)-hydroxycholesterol, 22(R)-hydroxycholesterol, 22(S)-hydroxycholesterol, 24-hydroxycholesterol, 24(S)-hydroxycholesterol, 24(S),25-epoxycholesterol, 25-hydroxycholesterol, 25(S)-hydroxycholesterol, 26-hydroxycholesterol, pregnanolone,

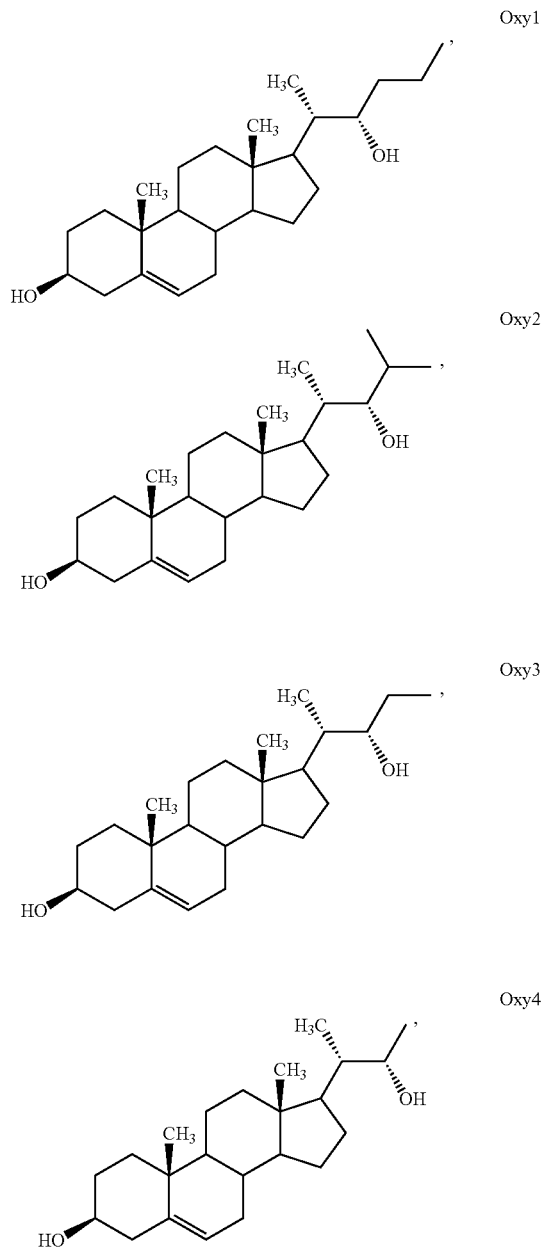

-continued
Oxy6
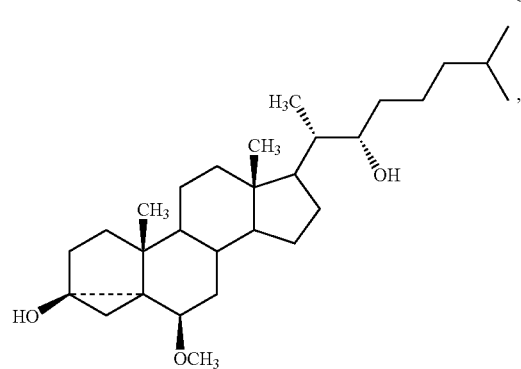
Oxy7
Oxy8
Oxy9
Oxy10
-continued
Oxy11
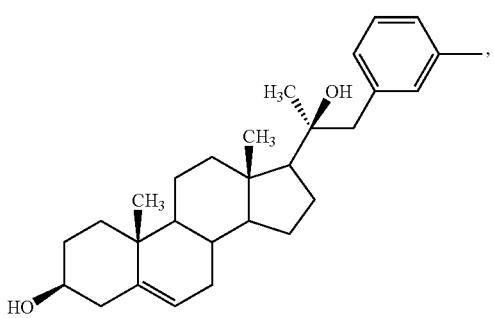
Oxy12
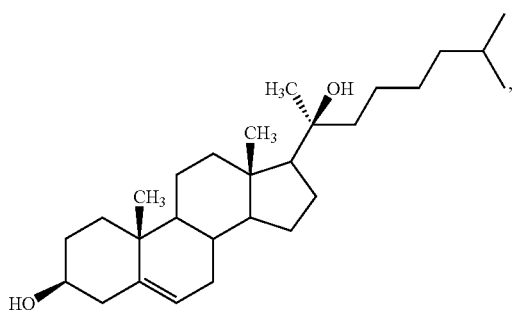
Oxy13
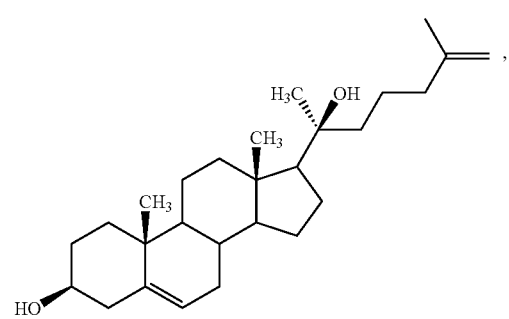
Oxy14
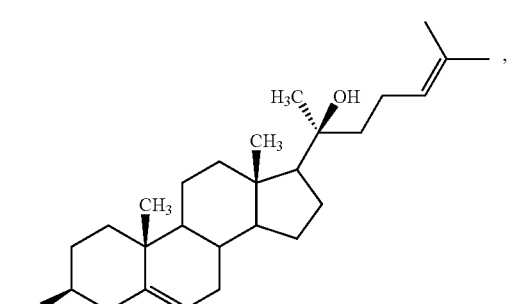
Oxy15, or
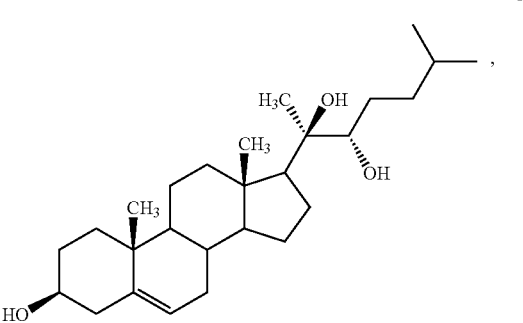

-continued

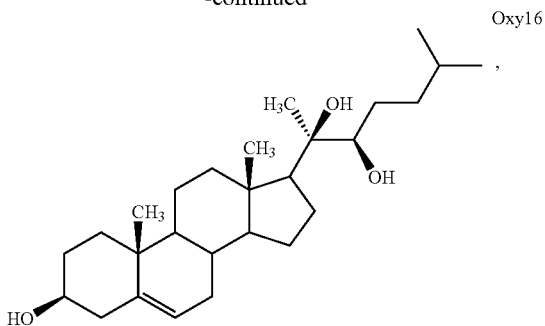

Oxy16

The oxysterol compound can be present in various forms and, if appropriate, as a pharmaceutically acceptable acid, base, or salt form.

The method of screening can include contacting a PPAR agonist and the candidate oxysterol, oxysterol analog, or active portion of an oxysterol with a cell and measuring the level of PPAR protein expression. The level of PPAR protein expression by the cell contacted with the PPAR agonist and the candidate can then be compared to the level of PPAR protein expression in a cell of the same type contacted with PPAR agonist, but not the candidate oxysterol, oxysterol analog, or active portion of an oxysterol. The ratio of the level of PPAR protein expression by the cell contacted with PPAR agonist, but not the candidate, to the level of PPAR protein expression by the cell contacted with the PPAR agonist and the candidate oxysterol, oxysterol analog, or active portion of an oxysterol can be determined. The ratio can be used as a metric of PPAR expression inhibition. A candidate oxysterol, oxysterol analog, or active portion of an oxysterol can be selected for exhibiting PPAR expression inhibition if the ratio of the level of PPAR protein expression by the cell contacted with PPAR agonist, but not the candidate, to the level of PPAR protein expression by the cell contacted with the PPAR agonist and the candidate oxysterol, oxysterol analog, or active portion of an oxysterol is greater than a predetermined ratio. For example, the predetermined ratio can be chosen to be 3, so that the level of PPAR protein expression by the cell contacted with PPAR agonist, but not the candidate, must be three-fold greater than the level of PPAR protein expression by the cell contacted with the PPAR agonist and the candidate oxysterol, oxysterol analog, or active portion of an oxysterol for the candidate to be selected. Alternatively, the predetermined ratio can be chosen to be 10, 100, or another value that one of skill in the art deems appropriate. Stated otherwise, the oxysterol compound may reduce PPAR expression to, e.g., about 1%, 5%, 10%, 30%, or a higher or lower level compared to the baseline level of expression. The cells used in the method can be marrow stromal cells (MSCs). The level of PPAR protein expression measured can be the level of PPARγ protein. The PPAR agonist used can be troglitazone.

The oxysterols used can be natural or synthetic. The oxysterols can exhibit any of a variety of activities, including the stimulation of osteomorphogenesis or osteoproliferation, and/or the inhibition of adipocyte morphogenesis or adipocyte proliferation, and thus can be used to treat conditions mediated by, or exhibiting aberrant expression of, those physiological phenomena. Certain oxysterols act by stimulating the hedgehog (Hh) signaling pathway. Thus oxysterols, including naturally occurring molecules as well as synthetic ones, can enhance this pathway, either in vitro or in vivo (in a subject) and can be used to treat conditions mediated by elements of the Hh pathway.

Advantages of oxysterols of the invention and methods for using them, e.g. for the treatment of suitable subjects, include that the compounds are inexpensive to manufacture, can be easily administered (e.g. locally or systemically), and exhibit great efficacy and potency. Bone morphogenic proteins (BMPs) can be used to enhance bone healing, but very large amounts of those proteins are required. Because oxysterols of the invention act synergistically with certain BMPs, lower doses of the proteins are required when they are co-administered with an oxysterol of the invention. This is another advantage of oxysterols of the invention. In some embodiments, administration of the compounds of the invention allows one to circumvent surgery, which can lead to scarring, e.g. in cosmetically sensitive areas.

One aspect of the invention is an oxysterol (e.g., an isolated oxysterol) represented by Formula 1.

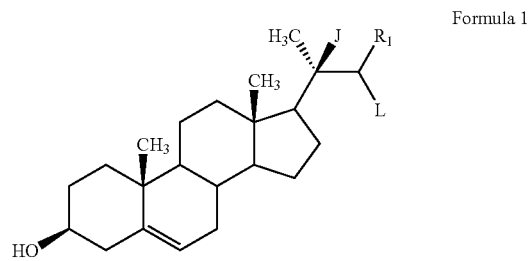

Formula 1

In Formula 1, J can be hydrogen (H) or hydroxyl (OH), L can be hydrogen (H) or hydroxyl (OH), and $R_1$ can be a linear or branched alkane of from 1 to 6 carbons, a linear or branched alkene of from 2 to 6 carbons, or phenyl optionally substituted with methyl. For example, at least one of J and L can be hydroxyl (OH) and/or at least one of J and L can be hydrogen (H). For example, $R_1$ can be other than 3-methylbutyl. For example, when J is OH, $R_1$ can be other than 3-methyl-2-butenyl, and when L is OH, $R_1$ can be other than n-propyl.

In one embodiment of the invention, J is hydroxyl (OH) and L is hydrogen (H). $R_1$ can be an alkane of from 5 to 6 carbons, for example, an alkane of from 5 to 6 carbons other than 3-methylbutyl. For example, $R_1$ can be 4-methylpentyl (Oxy 12). $R_1$ can be an alkene of from 5 to 6 carbons, for example, an alkene of from 5 to 6 carbons other than 3-methyl-2-butenyl. For example $R_1$ can be 3-methyl-3-butenyl (Oxy 13). $R_1$ can be phenyl optionally substituted with methyl. For example, $R_1$ can be 3-methylphenyl (Oxy 11).

In another embodiment, J is hydrogen (H) and L is hydroxyl (OH). $R_1$ can be an alkane of from 1 to 6 carbons. For example, $R_1$ can be methyl (Oxy 4), ethyl (Oxy 3), n-butyl (Oxy 9), or 4-methylpentyl (Oxy 7).

In another embodiment, J is hydroxyl (OH) and K is hydroxyl (OH). $R_1$ can be an alkane of from 1 to 6 carbons. For example, $R_1$ can be 3-methylbutyl (Oxy 15 and Oxy 16).

In another embodiment, a compound has Formula I and J is H or OH and L is H or OH. At least one of J and L is H and at least one of J and L is OH. R1 is selected from the group consisting of alkane of from 1 to 6 carbons, alkene of from 2 to 6 carbons, and phenyl optionally substituted with methyl. R1 is not 3-methylbutyl. When J is OH, R1 is not 3-methyl-2-butenyl. When L is OH, R1 is not n-propyl.

One embodiment is a pharmaceutical composition that comprises a compound having Formula I and a pharmaceutically acceptable carrier. J is H or OH, and L is H or OH. At least one of J and L is OH. R1 is selected from the group consisting of alkane of from 1 to 6 carbons, alkene of from 2 to 6 carbons, and phenyl optionally substituted with methyl. When one of J and L is H, R1 is not 3-methylbutyl. In another embodiment, the pharmaceutical composition further includes at least one additional oxysterol.

In one embodiment, the pharmaceutical composition includes at least two of Oxy 3, Oxy 4, Oxy 7, Oxy 9, Oxy 11, Oxy 12, Oxy 13, Oxy 14, and Oxy 15. The pharmaceutical composition may further comprise at least one of 20(S)-hydroxycholesterol, 22(S)-hydroxycholesterol, or 22(R)-hydroxycholesterol, or any other oxysterol. In one embodiment, the pharmaceutical composition includes Oxy 16.

Another aspect of the invention is a complex (in vitro or in vivo) comprising an oxysterol of the invention and any of variety of intracellular oxysterol binding molecules (e.g., proteins, receptors, etc.), examples of which will be evident to the skilled worker.

As used herein, the singular forms "a," "an" and "the" include plural referents unless the context clearly dictates otherwise. For example, "an" oxysterol" includes multiple oxysterols, e.g. 2, 3, 4, 5 or more oxysterols, which can be the same or different.

Another aspect of the invention is a combination or pharmaceutical composition comprising an oxysterol of the invention (optionally in combination of other agents as discussed above) and at least one additional agent, selected, e.g., from the group consisting of parathyroid hormone, sodium fluoride, insulin-like growth factor I (ILGF-I), insulin-like growth factor II (ILGF-II), transforming growth factor beta (TGF-β), a cytochrome P450 inhibitor, a phospholipase activator, arachadonic acid, a COX enzyme activator, an osteogenic prostanoid, an ERK activator, BMP 2, 4, 7 and 14.

Another aspect of the invention is a kit for performing any of the methods discussed herein, comprising one or more oxysterols of the invention, individually or in combination with one another, or in combination with naturally occurring oxysterols and/or with BMPs or other agents noted herein, optionally packaged in one or more containers. When the kit is for treating a subject, the oxysterol(s) may be in the form of a pharmaceutically acceptable composition.

Another aspect of the invention is a method for modulating a hedgehog (Hh) pathway mediated response in a cell or tissue, comprising contacting the cell or tissue with an effective amount of an oxysterol or a pharmaceutical composition of the invention. The cell or tissue may be in vitro or in a subject (in vivo). In the latter case, the subject can be one who would benefit, e.g., from the stimulation of osteomorphogenesis, osteoproliferation or hair growth; or the inhibition of adipocyte morphogenesis or adipocyte proliferation.

A "subject," as used herein, includes any animal that exhibits a symptom of a condition that can be treated with an oxysterol of the invention. Suitable subjects (patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by an oxysterol of the invention (e.g. stimulation of osteomorphogenesis or osteoproliferation, and/or the inhibition of adipocyte morphogenesis or adipocyte proliferation). Subjects exhibiting non-pathogenic conditions, such as alopecia, are also included. The ability of an oxysterol to "modulate" a response, as used herein, includes the ability to increase or to decrease the level of the response compared to the response elicited in the absence of the oxysterol. The aberrant activities may be regulated by any of a variety of mechanisms, including activation of a hedgehog activity, etc. The aberrant activities can result in a pathological condition.

An "effective amount," as used herein, includes an amount that can bring about a detectable effect. A "therapeutically effective amount," as used herein, includes an amount that can bring about a detectable therapeutic effect (e.g. the amelioration of a symptom).

Another aspect of the invention is a method for treating a subject suffering from a condition known to be mediated by oxysterols or by the hedgehog pathway, comprising administering to the subject an effective amount of an oxysterol or a pharmaceutical composition of the invention. Some such conditions are discussed elsewhere herein.

Another aspect of the invention is a method for inducing osteoblastic differentiation of a mammalian mesenchymal stem cell, comprising contacting the cell with an effective amount of an oxysterol or a pharmaceutical composition of the invention. This method can further comprise treating the mammalian mesenchymal cell with at least one secondary agent, selected from the group consisting of parathyroid hormone, sodium fluoride, insulin-like growth factor I (ILGF-I), insulin-like growth factor II (ILGF-II), transforming growth factor beta (TGF-β), a cytochrome P450 inhibitor, a phospholipase activator, arachadonic acid, a COX enzyme activator, an osteogenic prostanoid and an ERK activator.

Other aspects of the invention using an oxysterol or a pharmaceutical composition of the invention include methods for (1) stimulating a mammalian cell (e.g. a mesenchymal stem cell, an osteoprogenitor cell or a cell in a calvarial organ culture) to express a level of a biological marker of osteoblastic differentiation (e.g. an increase in at least one of alkaline phosphatase activity, calcium incorporation, mineralization or expression of osteocalcin mRNA) which is greater than the level of the biological marker in an untreated cell; (2) treating a subject (patient) to increase the differentiation of marrow stromal cells into osteoblasts; (3) treating a subject to induce bone formation (to increase bone mass); or (4) treating a patient exhibiting clinical symptoms of osteoporosis. Methods for treating a subject may comprise administering an oxysterol or a pharmaceutical composition of the invention at a therapeutically effective dose, in an effective dosage form, and at a selected interval to effectively carry out the elicit the desired response (e.g. to increase bone mass, to increase the number of osteoblasts present in bone tissue, to ameliorate the symptoms of the osteoporosis, respectively).

Another aspect of the invention is a method for treating a subject to induce bone formation comprising: harvesting mammalian mesenchymal stem cells; treating the mammalian mesenchymal cells with an oxysterol or a pharmaceutical composition of the invention, wherein the oxysterol induces the mesenchymal stem cells to express at least one cellular marker of osteoblastic differentiation; and administering the differentiated cells to the subject.

Another aspect of the invention is an implant for use in an animal (e.g. human) body, comprising a substrate having a surface, wherein at least the surface of the implant includes an oxysterol or a pharmaceutical composition of the invention, in an amount sufficient to induce bone formation in the surrounding bone tissue. The substrate may be formed into the shape of, e.g., a pin, screw, plate, or prosthetic joint.

Another aspect of the invention is a method for inhibiting adipocyte differentiation of a mammalian mesenchymal stem cell, comprising contacting the mesenchymal stem cell with an effective amount of an oxysterol or a pharmaceutical composition of the invention. The cell may be in vitro or in a subject (in vivo).

Another aspect of the invention is a method for identifying a modulator of a hedgehog pathway-mediated activity, comprising screening candidate oxysterols for the ability to modulate an activity in one of the hedgehog-related in vitro assays discussed herein (e.g., induction of expression of the Gli-1 gene, for example by stimulation of a Gli1 promoter; activation of a reporter construct driven by a multimerized Gli-1 responsive element; induction of expression of Patched; inhibition of a putative oxysterol-induced effect by cyclopamine; etc).

Another aspect of the invention is in a method for modulating a hedgehog (Hh) pathway mediated response in a cell or tissue (in vitro or in a subject), the improvement comprising contacting the cell or tissue with an oxysterol of the invention. Another aspect of the invention is in a method for treating a subject for one of the indications as described herein (e.g., to increase the differentiation of marrow stromal cells into osteoblasts, or to induce bone formation, the improvement comprising contacting the cell or tissue with an oxysterol of the invention).

One aspect of the invention is an oxysterol (e.g. an isolated oxysterol) of the invention as represented by Formula I, above. Examples of oxysterols, designated as Oxy 1 through Oxy 4 and Oxy 6 through Oxy 16 are presented in FIG. 9. For example, the compounds designated as Oxy 7, Oxy 9, Oxy11, Oxy12, Oxy13, Oxy 14, and Oxy 15 can stimulate at least a measurable amount of a hedgehog-mediated pathway and/or osteomorphogenesis or osteoproliferation (or a marker thereof), and/or can inhibit at least a measurable amount of adipocyte morphogenesis or adipocyte proliferation (or a marker thereof). Oxy 3 and Oxy 4 can act as enhancers of activity in combination with other oxysterols. For example, the combination of Oxy 3 and 20(S)-hydroxycholesterol, as well as the combination of Oxy4 and 20(S)-hydroxycholestol were found to enhance the incorporation of $^{45}$Ca in an assay used to measure mineralization in M2 cells over the incorporation when only 20(S)-hydroxycholestol was applied. Oxy 7 was found to be minimally enhancing of activity.

Other oxysterols have not been demonstrated to modulate one of the activities mentioned above. However, these molecules, which share structural features with the oxysterols discussed above, would be expected to act as competitive inhibitors of those compounds and, in some cases, to act as antagonists of one of the mentioned activities (e.g., of osteomorphogenesis or osteoproliferation, etc.).

In some aspects of the invention (e.g., methods in which oxysterols are used to stimulate members of the Hh pathway, naturally occurring oxysterols (e.g., 22(S)-hydroxycholesterol (sometimes referred to herein as "22S"); 22(R)-hydroxycholesterol (sometimes referred to herein as "22R"); 20(S)-hydroxycholesterol (also known as 20-alpha hydroxycholesterol, and sometimes referred to herein as "20S"); 5-cholesten-3beta, 20alpha-diol 3-acetate; 24-hydroxycholesterol; 24(S),25-epoxycholesterol; pregnanolone, 26-hydroxycholesterol; 4beta-hydroxycholesterol; can also be used.

By "isolated" is meant removed from its original environment (e.g., the natural environment if it is naturally occurring), and/or separated from at least one other component with which it is naturally associated. For example, a naturally-occurring oxysterol present in its natural living host is not isolated, but the same oxysterol, separated from some or all of the coexisting materials in the natural system, is isolated. Such an oxysterol can be part of a composition (e.g. a pharmaceutical composition), and still be isolated in that such composition is not part of its natural environment. Also, an intermediate product in the synthesis of another oxysterol, wherein the intermediate product is not purified or separated from other components in the reaction pathway, is not isolated.

It was observed that the hydroxyl groups in 20(S)-hydroxycholesterol and 22(S)-hydroxycholesterol are about 12-14 Å apart. Therefore, the putative receptor that mediates the effects of osteoinductive oxysterols may have a requirement for a diol in which the two hydroxyl groups are approximately 12-14 Å apart. In this light, we have synthesized and envision reaction schemes for the synthesis of synthetic oxysterols and derivatives thereof in which the functional group at the steroid 17 position is modified. With respect to modification of the functional group at the steroid 17 position, variants include, for example, the following: placement of a hydroxyl group at the steroid 20 position, the steroid 22 position, or both; inclusion of only single carbon-carbon bonds (alkane), double bonds (alkene), triple bonds (alkyne), or aromatic groups (e.g., phenyl, methylphenyl) in the functional group; and variation of stereochemistry. It is desirable to produce synthetic oxysterols that are derivatives of 20S-hydroxycholesterol and that are active even in the absence of 22S-hydroxycholesterol or 22R-hydroxycholesterol. For example, such synthetic oxysterols can be active in that they induce a measurable amount of a hedgehog-mediated pathway and/or osteomorphogenesis or osteoproliferation (or a marker thereof), and/or inhibit at least a measurable amount of adipocyte morphogenesis or adipocyte proliferation (or a marker thereof).

Combinations of oxysterols of the invention, with one another and/or with other oxysterols, including naturally occurring oxysterols, can also be used in methods of the invention. Among the naturally occurring oxysterols that can be used are: 22(S)-hydroxycholesterol; 22(R)-hydroxycholesterol; 20(S)-hydroxycholesterol (also known as 20-alpha hydroxycholesterol); 5-cholesten-3beta, 20alpha-diol 3-acetate; 24-hydroxycholesterol; 24(S),25-epoxycholesterol; 26-hydroxycholesterol; and/or 4beta-hydroxycholesterol.

Example VIII, below, provides illustrative synthetic procedures, as well as bibliographic citations.

The oxysterols discussed herein can be used to modulate a variety of responses or activities in a cell or tissue, in vitro or in vivo (in a subject). By "modulate" is meant is to increase or decrease the degree of the response.

The Examples herein illustrate some of the many activities that are exhibited by oxysterols of the invention. The present inventors and colleagues previously demonstrated that naturally occurring oxysterols (e.g. 22(S)-hydroxycholesterol (sometimes referred to herein as "22S"); 22(R)-hydroxycholesterol (sometimes referred to herein as "22R"); 20(S)-hydroxycholesterol (also known as 20-alpha hydroxycholesterol, and sometimes referred to herein as "20S"); 5-cholesten-3beta, 20alpha-diol 3-acetate; 24-hydroxycholesterol; 24(S),25-epoxycholesterol; pregnanolone, 26-hydroxycholesterol; and 4beta-hydroxycholesterol; individually or in combination, exhibit osteogenic and anti-adipogenic properties. See, e.g., the commonly owned and published PCT international applications WO2004/019884, WO2005/020928, WO2005/020928; and WO2006/12902, all of which are incorporated herein by reference in their entirety. See also Dwyer et al. (Jan. 2, 2007), *J. Biol. Chem.*, Epub ahead of print; Parhami et al. (2002) *J. Bone Miner. Res.* 17, 1997-2003; Kha et al. (2004) *J Bone Miner Res.* 19, 830-840; Shouhed et al. (2005) J *Cell Biochem* 95, 1276-1283; Richardson et al. (2006) (*J Cell Biochem*, in press); and Aghaloo et al. (2006) *J Orthop Res*, in press). In the present application, the inventors report that the novel oxysterols of the invention exhibit similar activities, as well as further activities. Such activities were demonstrated by a variety of markers of such activities.

In still further embodiments, the subject method can be employed for the generation of bone (osteogenesis) at a site in the animal where such skeletal tissue is deficient. Indian hedgehog is particularly associated with the hypertrophic chondrocytes that are ultimately replaced by osteoblasts. For instance, administration of a hedgehog agent of the present invention can be employed as part of a method for treating bone loss in a subject, e.g. to prevent and/or reverse osteoporosis and other osteopenic disorders, as well as to regulate bone growth and maturation. Periodontal implants are also contemplated. For example, preparations comprising oxysterol compounds can be employed, for example, to induce endochondral ossification, at least so far as to facilitate the formation of cartilaginous tissue precursors to form the "model" for ossification. Therapeutic compositions of hedgehog agonists can be supplemented, if required, with other osteoinductive factors, such as bone growth factors (e.g. TGF-β factors, such as the bone morphogenetic factors BMP-2, BMP-4, BMP-7 or BMP 14 as well as activin), and may also include, or be administered in combination with, an inhibitor of bone resorption such as estrogen, bisphosphonate, sodium fluoride, calcitonin, or tamoxifen, or related compounds. However, it will be appreciated that hedgehog proteins are likely to be upstream of BMPs, so that treatment with a hedgehog polypeptide and/or a hedgehog agonist will have the advantage of initiating endogenous expression of BMPs along with other factors.

The oxysterols discussed herein can be formulated into various compositions, e.g., pharmaceutical compositions, for use in therapeutic treatment methods. The pharmaceutical compositions can be assembled as a kit. Generally, a pharmaceutical composition of the invention comprises an effective amount of an oxysterol or combination of the invention. An "effective amount," as used herein, is an amount that is sufficient to effect at least a detectable therapeutic response in the individual over a reasonable time frame. For example, it can ameliorate, at least to a detectable degree, the symptoms of a hedgehog-mediated condition, etc. The composition can comprise a carrier, such as a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

A pharmaceutical composition or kit of the invention can contain other pharmaceuticals, as noted elsewhere herein, in addition to the oxysterols of the invention. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

Formulations suitable for oral administration can consist of liquid solutions, such as an effective amount of the agent dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract.

Formulations suitable for parenteral administration (e.g. intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The oxysterols of the invention, alone or in combination with other therapeutic agents, can be made into aerosol formulations to be administered via inhalation. These aerosol formulations can be placed into pressurized acceptable propellants, such as dichlorodifluoromethane, propane, nitrogen and the like.

The oxysterols of the invention, alone or in combinations with other therapeutic agents, can be made into suitable formulations for transdermal application and absorption (Wallace et al., 1993, supra). Transdermal electroporation or iontophoresis also can be used to promote and/or control the systemic delivery of the agents and/or pharmaceutical compositions of the present invention through the skin (e.g., see Theiss et al. (1991), Meth. Find. Exp. Clin. Pharmacol. 13, 353-359).

Formulations which are suitable for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, or the like.

One skilled in the art will appreciate that a suitable or appropriate formulation can be selected, adapted or developed based upon the particular application at hand.

Dosages for an oxysterols of the invention can be in unit dosage form, such as a tablet or capsule. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient. One skilled in the art also can readily determine and use an appropriate indicator of the "effective concentration" of the compounds of the present invention by a direct or indirect analysis of appropriate patient samples (e.g., blood and/or tissues).

The dose of an oxysterol of the invention, or composition thereof, administered to an animal, particularly a human, in the context of the present invention should be sufficient to effect at least a therapeutic response in the individual over a reasonable time frame. The exact amount of the dose will vary from subject to subject, depending on the species, age, weight and general condition of the subject, the severity or mechanism of any disorder being treated, the particular agent or vehicle used, its mode of administration and the like. The dose used to achieve a desired concentration in vivo will be determined by the potency of the particular oxysterol employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular agent, or composition thereof, employed. It is generally desirable, whenever possible, to keep adverse side effects to a minimum.

For example, a dose can be administered in the range of from about 5 ng (nanograms) to about 1000 mg (milligrams), or from about 100 ng to about 600 mg, or from about 1 mg to about 500 mg, or from about 20 mg to about 400 mg. For example, the dose can be selected to achieve a dose to body weight ratio of from about 0.0001 mg/kg to about 1500 mg/kg, or from about 1 mg/kg to about 1000 mg/kg, or from about 5 mg/kg to about 150 mg/kg, or from about 20 mg/kg to about 100 mg/kg. For example, a dosage unit can be in the range of from about 1 ng to about 5000 mg, or from about 5 ng to about 1000 mg, or from about or from about 100 ng to about 600 mg, or from about 1 mg to about 500 mg, or from about 20 mg to about 400 mg, or from about 40 mg to about 200 mg of a compound of according to the present invention. A dose can be administered once per day, twice per day, four times per day, or more than four times per day as required to elicit a desired therapeutic effect. For example, a dose administration regimen can be selected to achieve a blood serum concentration of a compound of the present invention in the range of from about 0.01 to about 1000 nM, or from about 0.1 to about 750 nM, or from about 1 to about 500 nM, or from about 20 to about 500 nM, or from about 100 to about 500 nM, or from about 200 to about 400 nM. For example, a dose administration regime can be selected to achieve an average blood serum concentration with a half maximum dose of a compound of the present invention in the range of from about 1 µg/L (microgram per liter) to about 2000 µg/L, or from about 2 µg/L to about 1000 µg/L, or from about 5 µg/L to about 500 µg/L, or from about 10 µg/L to about 400 µg/L, or from about 20 µg/L to about 200 µg/L, or from about 40 µg/L to about 100 µg/L.

A therapeutically effective dose of an oxysterol compound or other agent useful in this invention is one which has a positive clinical effect on a patient as measured by the ability of the agent to improve adipogenesis or PPAR expression related conditions. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

By way of example, the invention may include elevating endogenous, circulating oxysterol levels over the patient's basal level. In a normal adult levels are about 10-400 ng/ml depending on age and type of oxysterol, as measured by mass spectrometry. Those skilled in the art of pharmacology would be able to select a dose and monitor the same to determine if an increase in circulating levels over basal levels has occurred.

When given in combined therapy, the other agent can be given at the same time as the oxysterol, or the dosing can be staggered as desired. The two (or more) drugs also can be combined in a composition. Doses of each can be less when used in combination than when either is used alone.

The invention may include treatment with an additional agent which acts independently or synergistically with at least a first oxysterol compound to reduce adipogenesis, etc. Additional agents may be agents which, e.g., stimulate the mechanistic pathway by which oxysterols reduce adipogenesis and enhance osteoblastic differentiation. Among such suitable agents are bone morphogenic proteins (e.g., BMP 2, 4, 7, and/or 14), which have been shown by the inventors to act synergistically with oxysterols.

Therefore, the invention may include the use of a combination of at least one oxysterol of the invention and at least one BMP to induce osteoblastic differentiation or bone formation. This combination of agents to maintain bone homeostasis, enhance bone formation and/or enhance bone repair may be desirable at least in that the dosage of each agent may be reduced as a result of the synergistic effects. In one example, BMP2 may be used for localized use in fracture healing studies. The dosages used vary depending on mode of delivery. For example, beads coated with 10-100 micrograms of BMP2 have been used in mouse bone fracture studies. In studies with monkeys, BMP7 has been used in dosages ranging from 500-2000 micrograms. In studies with dogs, BMP2 has been used between 200-2000 micrograms. In studies where BMP2 was delivered in a sponge implanted in the fracture site, the dosage used was 1.5 mg/ml. In a spinal fusion trial where fusion was achieved, a large dose of 10 mg of BMP2 was used. In a human study of tibial non-union fractures in humans, BMP7 was used at several mg dosages.

Additional classes of agents which may be useful in this invention alone or in combination with oxysterols include, but are not limited to cytochrome P450 inhibitors, such as SKF525A. Other classes of agents useful in the invention include phospholipase activators, or arachadonic acid. Other classes of agents useful in the invention include COX enzyme activators, or prostaglandins or osteogenic prostanoids. Other classes of agents useful in the invention include ERK activators.

The invention may include combination treatments with oxysterols and other therapeutics. For example, oxysterols in combination with bisphosphonates, hormone therapy treatments, such as estrogen receptor modulators, calcitonin, and vitamin D1 calcium supplementation, PTH (such as Forteo or teriparatide, Eli Lilly), sodium fluoride and growth factors that have a positive effect on bone, such as insulin-like growth factors I and II and transforming growth factor beta. Those skilled in the art would be able to determine the accepted dosages for each of the therapies using standard therapeutic dosage parameters.

In this aspect of the invention, marrow stromal cells (MSCs) may be treated with an agent(s) to reduce adipogenesis and optionally to stimulate osteoblastic differentiation, as measured by any one of the increase in alkaline phosphatase activity, calcium incorporation, mineralization or osteocalcin mRNA expression, or other indicators of osteoblastic differentiation. In one embodiment of the invention MSC cells are harvested from a patient, treated with at least one oxysterol of the invention, and osteoblastic cells are administered to the patient.

The invention may include administering osteoblastically differentiated MSC systemically to the patient.

The invention may include placing osteoblastically differentiated MSC at selected locations in the body of a patient. In one embodiment of the invention, cells may be injected at a location at which bone homeostasis, formation and/or repair is desired.

In one application of the invention, the agents and methods may be applied to, but are not limited to the treatment or to slow the progression of bone related disorders, such as osteoporosis.

In applications of the invention, the agents and methods may be applied to, but are not limited to application of cells or agents to a surgical or fracture site, in periodontitis, periodontal regeneration, alveolar ridge augmentation for tooth implant reconstruction, treatment of non-union fractures, sites of knee/hip/joint repair or replacement surgery.

In one embodiment, the invention may include implants for use in the human body, comprising a substrate having a surface, wherein at least the surface of the implant includes at least one oxysterol of the invention in an amount sufficient to induce bone formation in the surrounding bone tissue, or the implant may include mammalian cells capable of osteoblastic differentiation, or osteoblastic mammalian cells, or a combination thereof for inducing bone formation or enhancing bone repair. For example, implants may include, but are not limited to pins, screws, plates or prosthetic joints which may be placed in the proximity of or in contact with a bone that are used to immobilize a fracture, enhance bone formation, or stabilize a prosthetic implant by stimulating formation or repair of a site of bone removal, fracture or other bone injury. The invention may also include the application of at least one agent or differentiated cells in the proximity of or in contact with a bone at a site of bone removal, fracture or other bone injury where bone formation or bone repair is desired.

Another embodiment of the invention is a kit useful for any of the methods disclosed herein, either in vitro or in vivo. Such a kit can comprise one or more of the oxysterols or pharmaceutical compositions discussed herein. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form. A skilled worker will recognize components of kits suitable for carrying out any of the methods of the invention.

In the foregoing and in the following examples, all temperatures are set forth in uncorrected degrees Celsius; and, unless otherwise indicated, all parts and percentages are by weight.

The agents discussed herein can be formulated into various compositions, e.g., pharmaceutical compositions, for use in therapeutic treatment methods. The pharmaceutical compositions can be assembled as a kit. Generally, a pharmaceutical composition of the invention comprises an effective amount of an oxysterol, oxysterol analog, or active portion of oxysterol or combination of the invention. An "effective amount," as used herein, is an amount that is sufficient to effect at least a detectable therapeutic response in the individual over a reasonable time frame. For example, it can ameliorate, at least to a detectable degree, the symptoms of a hedgehog-mediated condition, etc. An effective amount can prevent, reduce, treat, or eliminate the particular condition.

The composition can comprise a carrier, such as a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

A pharmaceutical composition or kit of the invention can contain other pharmaceuticals, in addition to the oxysterol compounds of the invention. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

Formulations suitable for oral administration can consist of liquid solutions, such as an effective amount of the agent dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract.

Formulations suitable for parenteral administration (e.g. intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The oxysterols, oxysterol analogs, or active portions of oxysterols of the invention, alone or in combination with other therapeutic agents, can be made into aerosol formulations to be administered via inhalation. These aerosol formulations can be placed into pressurized acceptable propellants, such as dichlorodifluoromethane, propane, nitrogen and the like.

The oxysterols, oxysterol analogs, or active portions of oxysterols of the invention, alone or in combinations with other therapeutic agents, can be made into suitable formulations for transdermal application and absorption (Wallace et al., 1993, supra). Transdermal electroporation or iontophoresis also can be used to promote and/or control the systemic delivery of the agents and/or pharmaceutical compositions of the present invention through the skin (e.g., see Theiss et al. (1991), *Meth. Find. Exp. Clin. Pharmacol.* 13, 353-359).

Formulations which are suitable for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, or the like.

One skilled in the art will appreciate that a suitable or appropriate formulation can be selected, adapted or developed based upon the particular application at hand.

Dosages for an oxysterol, oxysterol analog, or active portions of oxysterol of the invention can be in unit dosage form, such as a tablet or capsule. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient. One skilled in the art also can readily determine and use an appropriate indicator of the "effective concentration" of the compounds of the present invention by a direct or indirect analysis of appropriate patient samples (e.g., blood and/or tissues). Assays of hedgehog inhibition can calibrate dosage for particular oxysterols, oxysterol analogs, or active portions of oxysterol.

The dose of an oxysterol, oxysterol analog, active portions of oxysterol of the invention, or composition thereof, administered to an animal, particularly a human, in the context of the present invention should be sufficient to effect at least a therapeutic response in the individual over a reasonable time frame. The dose used to achieve a desired concentration in vivo will be determined by the potency of the particular oxysterol, oxysterol analog, active portions of oxysterol employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular agent, or composition thereof, employed. It is generally desirable, whenever possible, to keep adverse side effects to a minimum.

For example, a dose can be administered in the range of from about 5 ng (nanograms) to about 1000 mg (milligrams), or from about 100 ng to about 600 mg, or from about 1 mg to about 500 mg, or from about 20 mg to about 400 mg. For example, the dose can be selected to achieve a dose to body weight ratio of from about 0.0001 mg/kg to about 1500 mg/kg, or from about 1 mg/kg to about 1000 mg/kg, or from about 5 mg/kg to about 150 mg/kg, or from about 20 mg/kg to about 100 mg/kg. For example, a dosage unit can be in the range of from about 1 ng to about 5000 mg, or from about 5 ng to about 1000 mg, or from about or from about 100 ng to about 600 mg, or from about 1 mg to about 500 mg, or from about 20 mg to about 400 mg, or from about 40 mg to about 200 mg of a compound of according to the present invention. A dose can be administered once per day, twice per day, four times per day, or more than four times per day as required to elicit a desired therapeutic effect. For example, a dose administration regimen can be selected to achieve a blood serum concentration of a compound of the present invention in the range of from about 0.01 to about 20000 nM, or from about 0.1 to about 15000 nM, or from about 1 to about 10000 nM, or from about 20 to about 10000 nM, or from about 100 to about 10000 nM, or from about 200 to about 5000 nM, or from about 1000 to about 5000 nM. For example, a dose administration regime can be selected to achieve an average blood serum concentration with a half maximum dose of a compound of the present invention in the range of from about 1 µg/L (microgram per liter) to about 2000 µg/L, or from about 2 µg/L to about 1000 µg/L, or from about 5 µg/L to about 500 µg/L, or from about 10 µg/L to about 400 µg/L, or from about 20 µg/L to about 200 µg/L, or from about 40 µg/L to about 100 µg/L.

A therapeutically effective dose of an oxysterol, oxysterol analog, active portions of oxysterol or other agent useful in this invention is one which has a positive clinical effect on a patient as measured by the ability of the agent to reduce cell proliferation. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

When given in combined therapy, the other agent can be given at the same time as the oxysterol, oxysterol analog, active portions of oxysterol, or the dosing can be staggered as desired. The two (or more) drugs also can be combined in a composition. Doses of each can be less when used in combination than when either is used alone.

The invention may include treatment with an additional agent which acts independently or synergistically with the oxysterol compound. Additional classes of agents which may be useful in this invention alone or in combination with oxysterols, oxysterol analogs, active portions of oxysterols include, but are not limited to known anti-proliferative agents. Those skilled in the art would be able to determine the accepted dosages for each of the therapies using standard therapeutic dosage parameters.

The invention may include a method of systemic delivery or localized treatment alone or in combination with administration of other agent(s) to the patient.

Another embodiment of the invention is a kit useful for any of the methods disclosed herein, either in vitro or in vivo. Such a kit can comprise one or more of the oxysterols, oxysterol analogs, active portions of oxysterols, or pharmaceutical compositions discussed herein. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form. A skilled worker will recognize components of kits suitable for carrying out any of the methods of the invention.

In the foregoing and in the following examples, all temperatures are set forth in uncorrected degrees Celsius; and, unless otherwise indicated, all parts and percentages are by weight.

What a "statistically significant amount" is depends on the a number of factors, such as the technique of the experimenter and the quality of the equipment used. For example, in certain cases, a statistically significant amount may be a change of 1%. In other cases, a statistically significant amount can be represented by a change of at least about 5%, 10%, 20%, 50%, 75%, double, or more. In relation to inhibition, the significant reduction may be to a level of less than about 90%, 75%, 50%, 25%, 10%, 5%, 1%, or less.

EXAMPLES

Example I

Materials and Methods

Guidance for the performance of the assays described below can be found, e.g., in the commonly owned and published PCT international applications WO2004/019884, WO2005/020928, WO2005/020928; and WO2006/12902. See also Dwyer et al. (Jan. 2, 2007), *J. Biol. Chem*, Epub ahead of print; Parhami et al. (2002) *J. Bone Miner. Res.* 17, 1997-2003; Kha et al. (2004) *J Bone Miner Res.* 19, 830-840; Shouhed et al. (2005) *J Cell Biochem* 95, 1276-1283; Richardson et al. (2006) (*J Cell Biochem*, in press); and Aghaloo et al. (2006) *J Orthop Res*, in press).

Example II

In vivo Anti-adipogenic Effects of Oxysterols

We previously reported that both the inducer oxysterol, 20S, and the stimulatory oxysterols 22S and 22R, inhibit the adipogenic differentiation of M2 cells. Without wishing to be bound by any specific mechanism, this appears to suggest that the mechanism by which these oxysterols inhibit adipogenic differentiation might be distinct from that which induces osteogenic differentiation, and that therefore even some of the analogues that may be inactive in our osteoinductive tests may still inhibit adipogenesis. M2 cells are treated with PPARγ agonist, troglitazone (Tro) at 10 μM which induces adipogenesis in a variety of pluripotent cells including the M2 marrow stromal cells. The synthetic analogues are tested by treating M2 cells with Tro in the absence or presence of the individual oxysterols. After 8 days of treatment, at which time fully formed adipocytes are produced in M2 cultures treated with Tro, oil red O staining is performed to detect adipocytes that stain red due to the accumulation of neutral lipids. Adipocyte numbers are quantified by counting fields under a phase contrast microscope by conventional procedures. Those oxysterols that exhibit anti-adipogenic effects in vitro are also expected to inhibit adipogenesis in vivo.

Example III

Syntheses of Oxysterols

Some sources pertaining to the synthesis of oxysterols are as follows: Drew, J. et al., *J. Org. Chem.*, 52 (1987) 4047-4052; Honda, T. et al., *J. Chem. Soc., Perkin Trans.* 1, (1996) 2291-2296; Gen, A. V. D. et al. *J. Am. Chem. Soc.*, 95 (1973) 2656-2663; Mazzocchi, P. H. et al. S. *J. Org. Chem.*, 48 (1983) 2981-2989; Byon C. et al., *J Org Chem*, 41 (1976) 3716-3722; Rao, A.S., *Comprehensive Organic Synthesis*, Pergamon Press, Eds. Trost B M, Fleming I., 7 (chapter 3.1) (1991) 376-380.

A. Method of Synthesis of Oxy11 and Oxy12

1. Route to Synthesis of Oxy11

Imidazole (ImH) can be added to a solution of pregnenolone (compound 3, see Scheme 1) in anhydrous dimethylformamide (DMF). Tert-butyldimethylsilyltrifluoromethanesulfonate can then be added to the solution. The reaction product can be purified to obtain compound 4, 1-((3S,8S,9S,10R,13S,14S,17S)-2,3,4,7,8,9,10,11,12,13,14,15,16,17-tetradecahydro-3-[(1,1-dimethylethyl)dimethylsilyloxy]-10,13-dimethyl-1H-cyclopenta[α]phenanthren-17-yl) ethanone, as shown in Scheme 2.

The Grignard reagent 3-methylbenzylmagnesium bromide can then be reacted with 4 in a mixture of diethyl ether and tetrahydrofuran (THF). The silyl ether can be removed by the addition of tetrabutylammonium fluoride to yield compound 5a (Oxy 11) as shown in Scheme 1.

2. Route to Synthesis of Oxy12

The Grignard reagent isoheptylmagnesium bromide can then be reacted with 4 in a mixture of diethyl ether and THF. The silyl ether can be removed by the addition of tetrabutylammonium fluoride to yield compound 5c (Oxy 12) as shown in Scheme 1.

Scheme 1

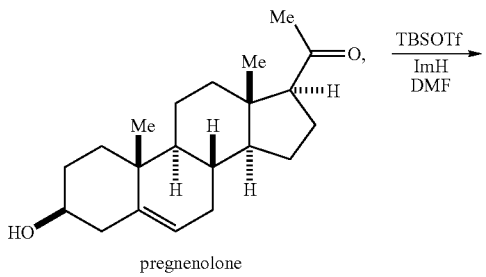

pregnenolone

3

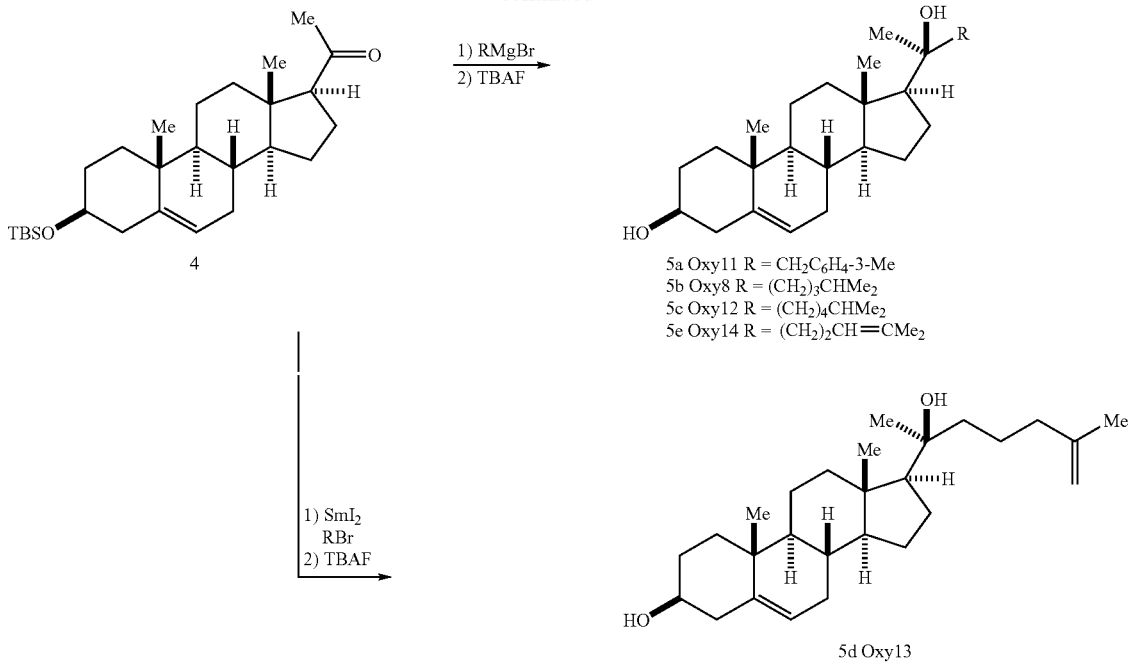

5a Oxy11 R = CH$_2$C$_6$H$_4$-3-Me
5b Oxy8 R = (CH$_2$)$_3$CHMe$_2$
5c Oxy12 R = (CH$_2$)$_4$CHMe$_2$
5e Oxy14 R = (CH$_2$)$_2$CH=CMe$_2$

5d Oxy13

B. Method of Synthesis of Oxy12 and Oxy13

1. Alternative Route to Synthesis of Oxy12

1-((3S,8S,9S,10R,13S,14S,17S)-2,3,4,7,8,9,10,11,12,13,14,15,16,17-tetradecahydro-3-[(1,1-dimethylethyl)dimethylsilyloxy]-10,13-dimethyl-1H-cyclopenta[α]phenanthren-17-yl)ethanone, 1

To a stirred solution of pregnenolone (5.0 g, 15.8 mmol) in anhydrous dimethylformamide (DMF, 180 mL) was added imidazole (2.7 g. 39.7 mmol). The reaction was allowed to stir for 20 min followed by slow addition of tent-butyldimethylsilyl chloride (3.6 g., 23.9 mmol). After stirring for 12 h at ambient temperature, the reaction mixture was poured over ice. The precipitates were collected and dissolved in diethyl ether. The organic phases were washed with brine, dried over Na$_2$SO$_4$ and evaporated in vacuo to yield compound 1 (6.7 g, 15.6 mmol, 98%) as a white powder which was used without further purification. The spectroscopic data was identical to those reported in the literature (Drew et al. (1987) *J. Org. Chem.* 52, 4047-4052).

(3S,8S,9S,10R,13S,14S,17S)-2,3,4,7,8,9,10,11,12,13,14,15,16,17-tetradecahydro-3-[(1,1-dimethylethyl)dimethylsilyloxy]-17-((S)-2-hydroxy-7-methyloctan-2-yl) -10,13-dimethyl-1H-cyclopenta[α] phenanthrene, 2

To a stirred suspension of samarium metal (758 mg, 5.0 mmol) and 3 Å molecular sieves (0.5 g) in anhydrous tetrahydrofuran (THF, 9.5 mL) was slowly added a solution of 1,2-diiodoethane (1.3 g, 4.6 mmol) in THF (9.5 mL) at ambient temperature. After the reaction stirred for 30 min, hexamethylphosphoramide (HPMA, 3.0 mL, 17.2 mmol) was added to the reaction mixture and continued stirring for an additional 20 min. Then, a solution of ketone 1 (500.0 mg, 1.16 mmol) in THF (6.0 mL) was added followed by a solution of 1-bromo-5-methylhexane (208.0 mg, 1.16 mmol) in THF (2.0 mL). The reaction was allowed to stir for an additional hour until the starting material was completely consumed. After this, the reaction mixture was slowly treated with saturated NaHCO$_3$, filtered through Celite and rinsed three times with an excess amount of diethyl ether. The filtrate was treated with water and extracted with diethyl ether. The ether extracts were washed with brine, dried over Na$_2$SO$_4$ and evaporated in vacuo to give a residue which was purified via silica gel chromatography. Elution with hexane-diethyl ether (4:1, v/v) afforded compound 2 (350.0 mg, 0.6 mmol, 57%) as a white powder (Honda et al. (1996) *J. Chem. Soc., Perkin Trans.* 1, 2291-2296).

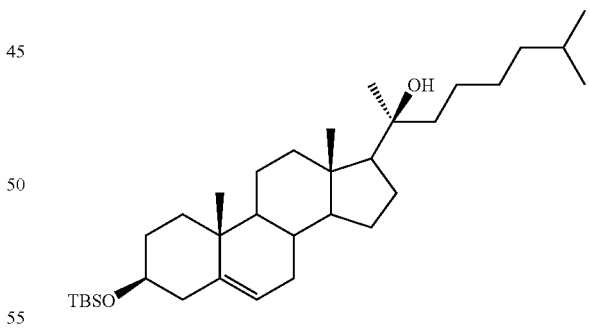

$^1$H NMR (500 MHz, CDCl$_3$) δ 0.05 (s, 6H), 0.86 (s, 3H), 0.86 (d, J=6.6 Hz, 6H), 0.89 (s, 9H), 1.00 (s, 3H), 1.02-1.17 (m, 8H), 1.26 (s, 3H), 1.29-1.81 (m, 18H), 1.95-1.99 (m, 1H), 2.07-2.10 (m, 1H), 2.14-2.18 (m, 1H), 2.24-2.26 (m, 1H), 3.46-3.50 (m, 1H), 5.31 (app t, J=5.2 Hz, 1H). $^{13}$C NMR (125 MHz, CDCl$_3$) δ −4.7, 13.5, 18.1, 19.3, 20.8, 22.2, 22.4, 22.5, 23.7, 24.4, 25.8, 26.3, 27.8, 27.9, 31.2, 31.7, 32.0, 36.5, 37.3, 38.9, 40.0, 42.5, 42.7, 43.9, 50.0, 56.8, 57.4, 72.4, 75.0, 120.9, 141.4.

(3S,8S,9S,10R,13S,14S,17S)-2,3,4,7,8,9,10,11,12, 13,14,15,16,17-tetradecahydro-17-((S)-2-hydroxy- 7-methyloctan-2-yl)-10,13-dimethyl-1H-cyclopenta [α]phenanthren-3-ol, Oxy12

To a solution of compound 2 (300.0 mg, 0.57 mmol) in anhydrous THF was added a 1.0 M solution of tetrabutylammonium fluoride in THF (2.5 mL, 2.5 mmol) and the solution was allowed to stir at ambient temperature. After 12 h, the reaction was treated with water and extracted three times with diethyl ether. The organic phases were collected, dried over $Na_2SO_4$ and concentrated in vacuo to give an oil. Flash column chromatography of this oil (silica gel, 1:3 hexane/diethyl ether) yielded the compound Oxy12 (210.0 mg, 0.50 mmol, 88%) as a white powder.

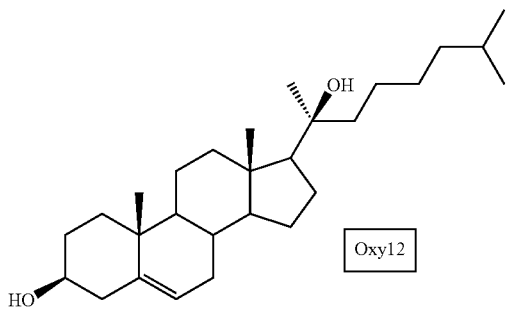

$^1$H NMR (500 MHz, CDCl$_3$) δ 0.86 (s, 3H), 0.86 (d, J=6.6 Hz, 6H), 1.01 (s, 3H), 1.02-1.25 (m, 11H), 1.26 (s, 3H), 1.42-1.76 (m, 14H), 1.82-1.85 (m, 2H), 1.95-1.99 (m, 1H), 2.07-2.11 (m, 1H), 2.23-2.30 (m, 2H), 3.49-3.55 (m, 1H), 5.35 (app t, J=5.2 Hz, 1H). $^{13}$C NMR (125 MHz, CDCl$_3$) δ 13.5, 19.3, 20.8, 22.2, 22.5, 23.7, 24.4, 26.3, 27.8, 27.9, 31.2, 31.5, 31.7, 36.4, 37.1, 38.9, 39.0, 40.0, 42.2, 42.5, 44.0, 56.8, 57.5, 71.7, 75.1, 121.5, 140.7.

2. Route to Synthesis of Oxy13

Ethyl 4-methylpent-4-enoate, 7

A solution of 2-methyl-2-propen-1-ol (12.9 g, 0.18 mol), triethyl orthoacetate (230.0 mL, 1.3 mol) and propionic acid (0.9 mL, 0.12 mol) was heated to 170° C. (external). The reaction apparatus was equipped with a Vigreaux Claisen adapter with a collection flask to remove the ethanol produced. The reaction mixture was left under reflux overnight. The excess amount of triethyl orthoacetate was gently distilled off at 130 mm Hg until the temperature in the reaction flask began to increase. After the reaction was cool, the remaining liquid was treated with 300 mL of 10% monobasic potassium phosphate and the left reaction was stirred for 90 min at ambient temperature. The reaction mixture was extracted with diethyl ether (3×100 mL). The combined organic phase was dried over $Na_2SO_4$ and concentrated in vacuo to give a yellow oil. Flash column chromatography of this oil (silica gel, 4:1 hexane/diethyl ether) afforded compound 7 as a colorless oil (17.0 g, 0.12 mmol, 67%) (Gen et al. (1973) J. Am. Chem. Soc. 95, 2656-2663).

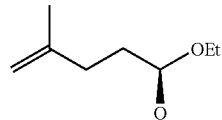

$^1$H NMR (500 MHz, CDCl$_3$) δ 1.25 (t, J=7.2 Hz, 3H), 1.74 (s, 3H), 2.33 (t, J=7.9 Hz, 2H), 2.45 (t, J=8.0 Hz, 2H), 4.13 (q, J=7.1 Hz, 2H), 4.68 (s, 1H), 4.74 (s, 1H).

4-Methylpent-4-en-1-ol, 8

To a flame-dried flask that was purged under argon for 20 min was added LiAlH$_4$ followed by 150 mL of anhydrous THF. The reaction mixture was cooled to 0° C. and a solution of compound 7 in THF (20 mL) was added slowly. The resulting solution was allowed to warm to room temperature and was stirred for 3 h until the starting material was completely consumed as indicated by TLC. The reaction was quenched by slow addition of the mixture to 300 mL of ice cold 1M NaOH. The mixture was then allowed to stir for another hour and was filtered through Celite. A large amount of diethyl ether was used for rinsing. The filtrate was treated with water and extracted twice with diethyl ether. The combined organic phase was dried over $Na_2SO_4$ and evaporated in vacuo to give a residue which was purified via distillation at 20 mm Hg (bp 65-68° C.) to afford compound 8 as a yellow oil (9.5 g, 0.095 mol, 79%) (Mazzocchi et al. (1983) J. Org. Chem. 48, 2981-2989).

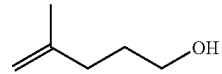

$^1$H NMR (500 MHz, CDCl$_3$) δ 1.47 (br, 1H), 1.69-1.74 (m, 5H), 2.1 (t, J=7.5 Hz, 2H), 3.66 (t, J=6.5 Hz, 2H), 4.71 (d, J=0.8 Hz, 1H), 4.73 (d, J=0.8 Hz, 1H), 4.73 (d, J=0.4 Hz, 1H); $^{13}$C NMR (125 MHz, CDCl$_3$), δ 22.22, 30.41, 33.98, 62.64, 110.08, 145.40.

5-Bromo-2-methyl-1-pentene, 9

To a solution of compound 8 (8.8 g, 0.088 mol) in pyridine (150 mL) cooled to 0° C. was added p-toluenesulfonyl chloride (35.0 g, 0.18 mol) in small portions. After the reaction mixture stirred for 20 minutes, it was allowed the reaction mixture to warm to room temperature over 3 h. The solution was acidified with 1 M HCl and extracted three times with diethyl ether. The ether extracts were washed with 1 M HCL, saturated NaHCO$_3$ and brine. The combined organic layers were dried over $Na_2SO_4$ and evaporated in vacuo to yield the crude tosylate which was used without further purification.

The tosylate (23.8 g, 0.094 mol) was dissolved in acetone (150 mL) and LiBr (17.0 g, 0.20 mol) was added slowly at ambient temperature. The reaction was left under reflux at 75° C. for 3 h. The solution was poured into ice water and extracted with diethyl ether (3×200 mL). The combined the organic layers were dried over $Na_2SO_4$ and concentrated in vacuo to afford a yellow oil. Flash column chromatography of this oil (silica gel, 9:1 hexane/diethyl ether) gave compound 9 (7.0 g, 0.043 mol, 49%) as a colorless oil.

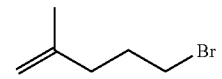

$^1$H NMR (500 MHz, CDCl$_3$) δ 1.73 (s, 3H), 1.97-2.02 (m, 2H), 2.16 (t, J=7.2 Hz, 2H), 3.41 (t, J=6.7 Hz, 2H), 4.72 (d, J=1.0 Hz, 1H), 4.76 (d, J=0.5 Hz, 1H); $^{13}$C NMR (125 MHz, CDCl$_3$) δ 22.18, 30.47, 33.17, 35.92, 110.88, 143.82.

(3S,8S,9S,10R,13S,14S,17S)-2,3,4,7,8,9,10,11,12,13,14,15,16,17-tetradecahydro-3-[(1,1-dimethylethyl)dimethylsilyloxy]-17-((S)-2-hydroxy-6-methylhept-6-en-2-yl)-10,13-dimethyl-1H-cyclopenta[α]phenanthrene, 10

The coupling reaction of the protected pregnenolone 1 (500.0 mg, 1.16 mmol) with 5-bromo-2-methyl-1-pentene 9 (199.0 mg, 1.22 mmol) in the presence of samarium diiodide was performed under similar condition as described for the preparation of 2 to afford the 20S-hydroxy steroid 10 (419.0 mg, 0.82 mmol, 71%) as a white powder.

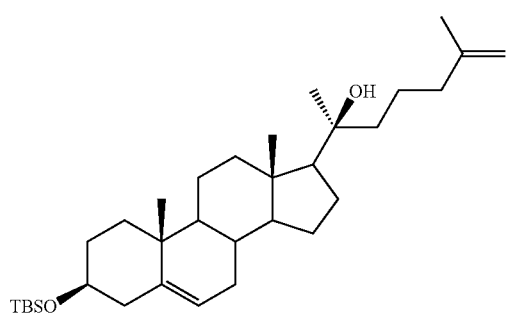

$^1$H NMR (500 MHz, CDCl$_3$) δ 0.05 (s, 6H), 0.86 (s, 3H), 0.89 (s, 9H), 1.00 (s, 3H), 1.13-1.22 (m, 5H), 1.28 (s, 3H), 1.32-1.55 (m, 11H), 1.71 (s, 3H), 1.72-1.79 (m, 5H), 1.97-2.0 (m, 6H), 3.47-3.48 (m, 1H), 4.67 (s, 1H), 4.70 (s, 1H), 5.31 (app t, J=5.3 Hz, 1H). $^{13}$C NMR (125 MHz, CDCl$_3$) δ −4.7, 13.5, 18.1, 19.3, 20.8, 22.1, 22.2, 22.3, 23.7, 25.8, 26.3, 31.2, 31.7, 32.0, 36.5, 37.3, 38.2, 40.0, 42.6, 42.7, 43.4, 50.0, 56.8, 57.7, 72.5, 75.0, 109.8, 120.9, 141.5, 145.7.

(3S,8S,9S,10R,13S,14S,17S)-2,3,4,7,8,9,10,11,12,13,14,15,16,17-tetradecahydro-17-(S)-2-hydroxy-6-methylhept-6-en-2-yl)-10,13-dimethyl-1H-cyclopenta[α]phenanthren-3-ol, Oxy13

The deprotection of the silyl ether 10 was carried out under similar conditions as those used for the preparation of the compound Oxy12 to afford compound Oxy13 (300.0 mg, 0.75 mmol, 91%) as a white powder.

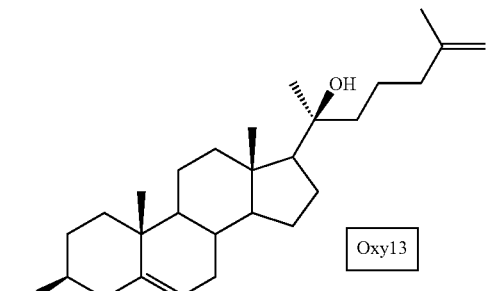

$^1$H NMR (500 MHz, CDCl$_3$) δ 0.86 (s, 3H), 1.00 (s, 3H), 1.12-1.20 (m, 5H), 1.28 (s, 3H), 1.32-1.65 (m, 14H), 1.73 (s, 3H), 1.83-2.0 (m, 5H), 2.07-2.09 (m, 1H), 2.23-2.28 (m, 2H), 2.48 (br, 1H), 3.52-3.54 (m, 1H), 4.67 (s, 1H), 4.70 (s, 1H), 5.35 (app t, J=2.0 Hz, 1H). $^{13}$C NMR (125 MHz, CDCl$_3$) δ 13.5, 19.3, 20.8, 22.1, 22.2, 22.3, 23.7, 26.3, 31.2, 31.5, 31.7, 36.4, 37.1, 38.2, 40.0, 42.2, 42.6, 43.4, 49.9, 56.8, 57.7, 71.6, 75.0, 109.8, 121.5, 140.7, 145.7.

C. Method of Synthesis of Oxy15 and Oxy16

The pregnenolone silyl ether (compound 4, see Schemes 1 and 2) can be reacted with 4-methylpentynyllithium in tetrahydrofuran (THF) and the resulting alcohol was then reduced using Lindlar's catalyst to give a mixture of cis and trans alkenes which were separated. The cis isomer was epoxidized using t-butyl hydroperoxide and vanadyl acetoacetate to give a mixture of the two epoxides (the first shown in Scheme 2 being major). Hydride reduction of the hydroxy epoxides individually gave the diols. Final removal of the silyl ether of the two diols gave the triols, Oxy15 and Oxy16.

Scheme 2

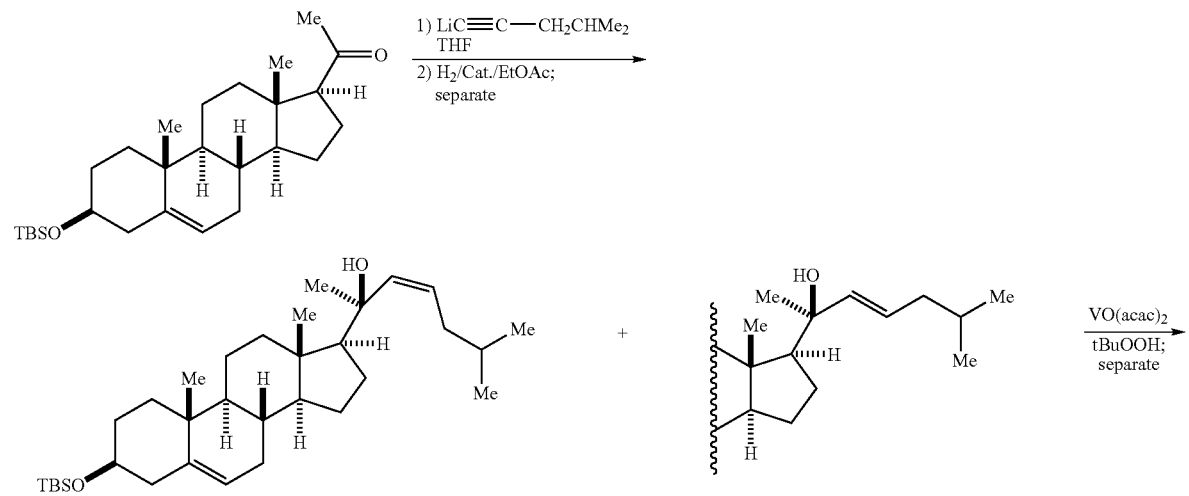

-continued

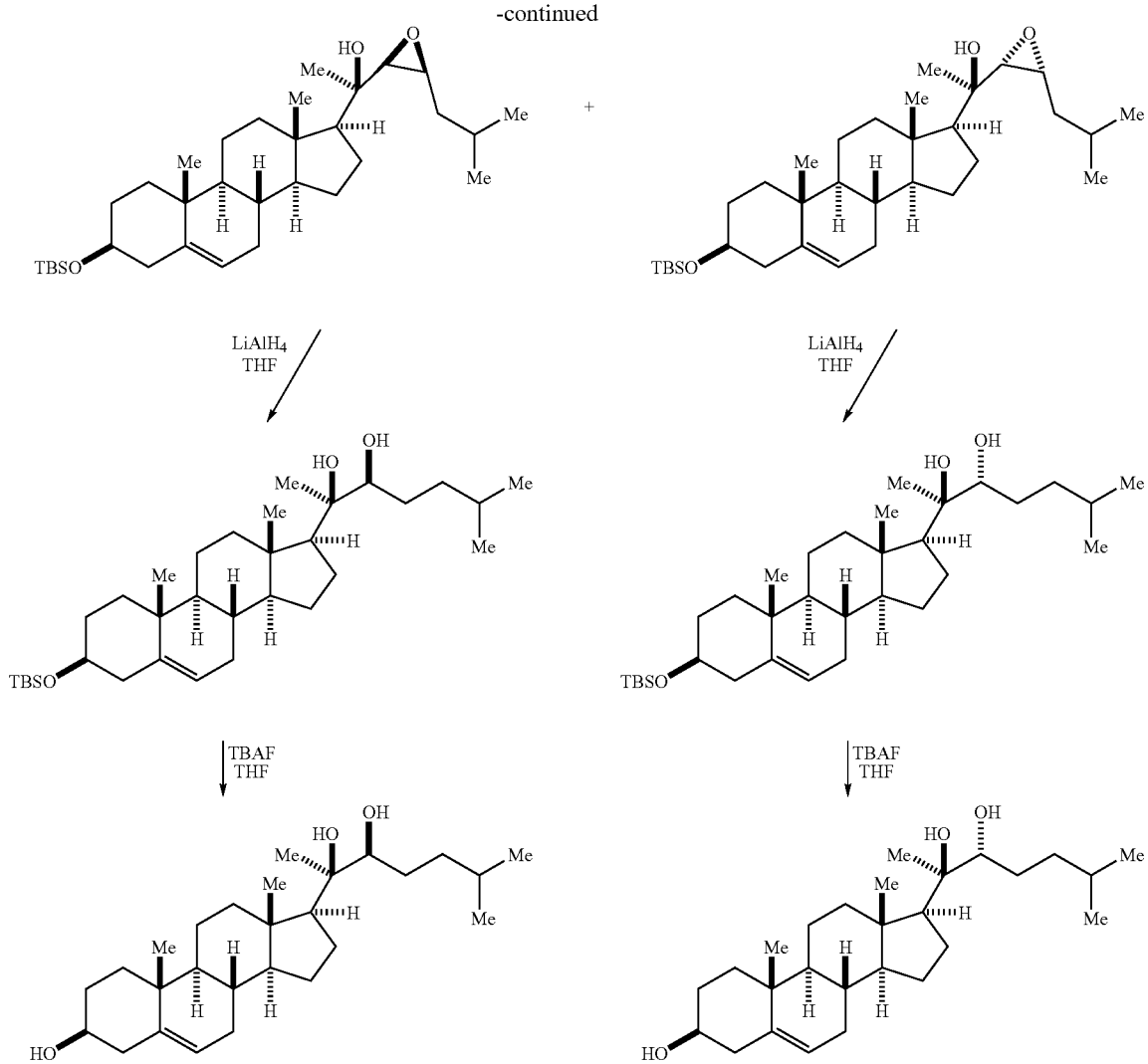

Example IV

Study Elucidating Inhibition of PPARγ Expression by Oxysterols

This example demonstrates the anti-adipogenic effects of an osteogenic oxysterol, 20(S)-hydroxycholesterol, which are mediated through a hedgehog-dependent mechanism(s) and are associated with inhibition of PPARγ expression. The M2-10B4 (M2) murine pluripotent bone MSC line was used to assess the inhibitory effects of 20(S)-hydroxycholesterol (20S) and sonic hedgehog (Shh) on peroxisome proliferator-activated receptor γ (PPARγ) and adipogenic differentiation. All results were analyzed for statistical significance using ANOVA.

Treatment of M2 cells with the osteogenic oxysterol 20S completely inhibited adipocyte formation induced by troglitazone after 10 days. PPARγ mRNA expression assessed by RT-qPCR was significantly induced by Tro after 48 h (5-fold) and 96 h (130-fold), and this induction was completely inhibited by 20S. In contrast, 20S did not inhibit PPARγ transcriptional activity in M2 cells overexpressing PPARγ and retinoid X receptor (RXR). The hedgehog signaling inhibitor, cyclopamine, reversed the inhibitory effects of 20S and Shh on troglitazone-induced adipocyte formation in 10-day cultures of M2 cells by 70% and 100%, respectively, and the inhibitory effect of 20S and Shh on troglitazone-induced PPARγ expression was fully reversed at 48 h by cyclopamine. Furthermore, 20S and Shh greatly inhibited PPARγ2 promoter activity induced by CCAAT/enhancer-binding protein a overexpression. These studies show that the inhibition of adipogenesis in murine MSCs by the osteogenic oxysterol, 20S, is mediated through a hedgehog-dependent mechanism(s).

20S was purchased from Sigma-Aldrich (St Louis, Mo., USA), recombinant mouse sonic hedgehog, amino-terminal peptide from R&D Systems (Minneapolis, Minn., USA), troglitazone from BioMol Research Laboratories (Plymouth Meeting, Pa., USA), cyclopamine and PD98059 from Calbiochem (La Jolla, Calif., USA), RPMI 1640 from Irvine Scientific (Santa Ana, Calif., USA), and FBS from Hyclone (Logan, Utah, USA).

M2 mouse MSCs were purchased from American Type Culture Collection (ATCC, Rockville, Md., USA). These cells were maintained in growth medium consisting of RPMI 1640 with 10% heat-inactivated FBS and supplemented with 1 mM sodium pyruvate, 100 U/ml penicillin, and 100 U/ml streptomycin. Cell culture was performed in 24- and 6-well plates for adipogenic differentiation and gene expression studies, respectively, and treatment with test agents was done in growth medium.

Oil red O staining for detection of adipocytes was performed as previously described. See, Parhami F et al. 1999, Atherogenic diet and minimally oxidized low density lipoprotein inhibit osteogenic and promote adipogenic differentiation of marrow stromal cells, J Bone Miner Res 14:2067-2078. The number of adipocytes was quantitated by counting Oil red O-positive cells in five separate fields per well, in three wells per experimental condition. The results are reported as the mean of triplicate determination ±SD.

Total RNA was extracted with the RNA isolation kit from Stratagene (La Jolla, Calif., USA) according to the manufacturer's instructions. RNA was DNase-treated using DNA-free kit from Ambion (Austin, Tex., USA). Three micrograms of RNA was reverse-transcribed using reverse transcriptase from Stratagene to make single-stranded cDNA. The cDNA was mixed with Qi SYBR Green Supermix (Bio-Rad) for quantitative RT-PCR assay using a Bio-Rad I-cycler IQ quantitative thermocycler. All PCR samples were prepared in triplicate wells of a 96-well plate. After 40 cycles of PCR, melt curves were examined to ensure primer specificity. Fold changes in gene expression were calculated using the $\Delta\Delta Ct$ method. See, Tichopad A et al. 2003, Standardized determination of real-time PCR efficiency from a single reaction set-up, Nucleic Acids Res 31:e122. Primers used are as follows: PPARγ2 (5'-TGAAACTCTGGGAGATTCTCCTG-3' and 5'-CCATGGTAATTTCTTGTGAAGTGC-3'), C/EBPα (5'-GGACAAGAACAGCAACGAGTACC-3' and 5'-GGCGGTCATTGTCACTGGTC-3'), ap2 (5'-GRCAC-CATCCGGTCAGAGAGTAC-3' and 5'-TCGTCTGCGGT-GATTTCATC-3'), LPL (5'-GTGGCCGAGAGCGAGAAC-3' and 5'-AAGAAGGAGTAGGTTTTATTTGTGGAA-5'), GATA2 (5'-ATCCACCCTTCCTCCAGTCT-3' and 5'-CTCTCCAAGTGCATGCAAGA-3'), GATA3 (5'-AGAAGGCATCCAGACCCGAAAC-3' and 5'-AACTTG-GAGACTCCTCACGCATGTG-3'), GILZ (5'-GCTGCA-CAATTTCTCCACCT-3' and 5'-GCTCACGAATCTGCTCCTTT-3'), and pref-1 (5'-CT-GTGTCAATGGAGTCTGCAAG-3' and 5'-CTACGATCT-CACAGAAGTTGC-3'). See, Spinella-Jaegle S et al. 2001, Sonic hedgehog increases the commitment of pluripotent mesenchymal cells into the osteoblastic lineage and abolishes adipocytic differentiation, J Cell Sci 114:2085-2094; Suh J M et al. 2006, Hedgehog signaling plays a conserved role in inhibiting fat formation, Cell Metab 3:25-34; Lay S L et al. 2002, Insulin and sterol-regulatory element-binding protein-1c (SREBP-1c) regulation of gene expression in 3T3-L1 adipocytes, J Biol Chem 277:35625-35634; Shi X et al. 2003 A glucocorticoid-induced leucine-zipper protein, GILZ, inhibits adipogenesis of mesenchymal cells, EMBO Rep 4:374-380; Phan J et al. 2004, Lipin expression preceding peroxisome proliferators-activated receptor-gamma is critical for adipogenesis in vivo and in vitro, J Biol Chem 279:29558-29564.

M2 cells at 70% confluency in a 24-well plate were transiently transfected with: a plasmid containing three tandem repeats of the PPAR response element (PPRE) upstream of the basic thymidine kinase promoter (p3xPPRE-TK-Luciferase), a control pTK-Luciferase plasmid devoid of PPRE, a CMX-PPARγ expression plasmid (all kind gifts of Dr Peter Tontonoz), a CMX-RXRα expression plasmid (kind gift of Dr Sotirios Tetradis), and a pTK-Renilla-Luciferase plasmid (Promega, Madison, Wis., USA) using Fugene 6 Transfection Reagents from Roche (Indianapolis, Ind., USA). Luciferase activity assay was performed using Dual-Luciferase Reporter 1000 Assay System (Promega, Madison, Wis., USA). Luciferase reporter activity was normalized to Renilla Luciferase activity. Transfection efficiency was monitored by co-transfecting with a plasmid expressing green fluorescent protein and found to be >30%. For GATA reporter assays, M2 cells were transfected with a GATA Luciferase reporter vector or a control reporter vector (both from Panomics, Fremont, Calif., USA), and pTK-Renilla-Luciferase plasmid.

For PPARγ promoter activity assays, M2 cells were transiently transfected with a murine PPARγ2 promoter construct luciferase plasmid (p19-PPARγ2; (kind gift of Dr Steven McKnight), along with MSV-C/EBPα overexpression plasmid (kind gift of Dr. Sophia Tsai) and pTK-Renilla-Luciferase plasmid. Luciferase activity was measured after 24 h and normalized for transfection efficiency using the Renilla Luciferase activity.

Statistical analyses were performed using the StatView 5 program. All p values were calculated using ANOVA and Fisher's projected least significant difference (PL-SD) significance test. A value of $p<0.05$ was considered significant.

Results

Figure 1B:
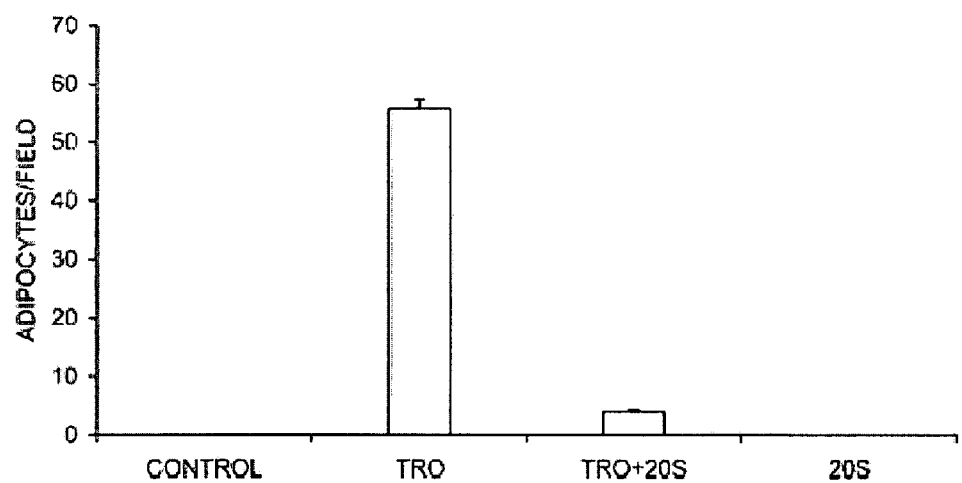
FIG. 1B presents a bar graph illustrating the number of adipocytes after various treatments.
Figure 2A:
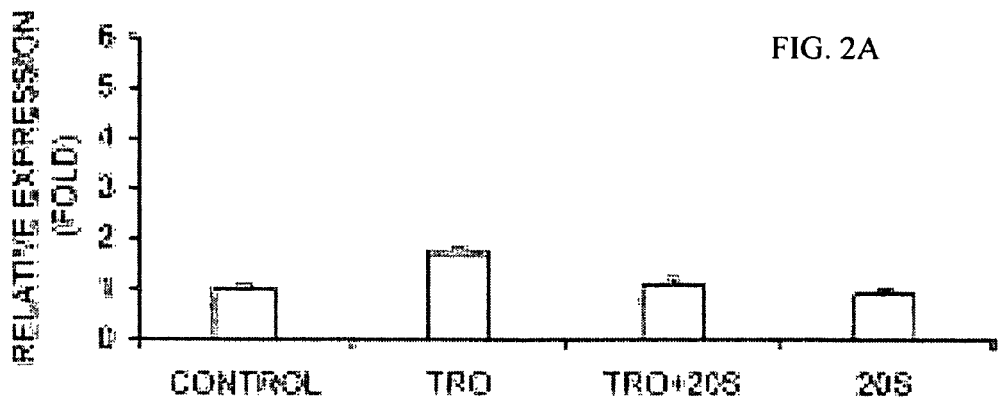
FIGS. 2A-2C present bar graphs illustrating PPARγ mRNA expression by M2 cells after various treatments.
Figure 2B:
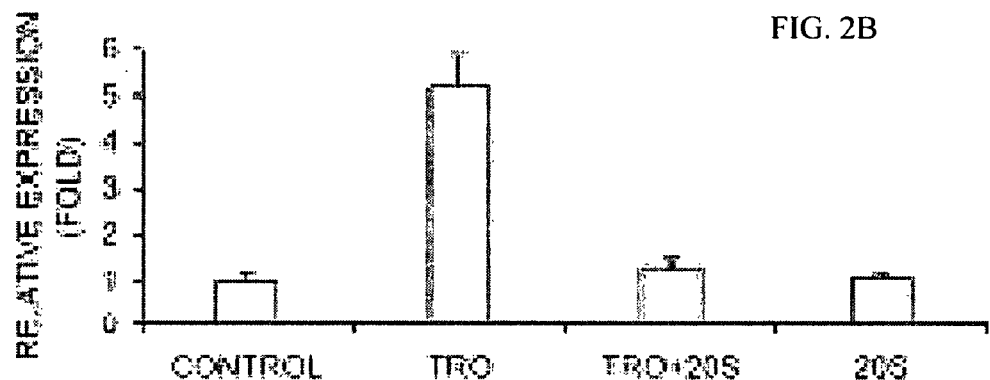
Figure 2C:
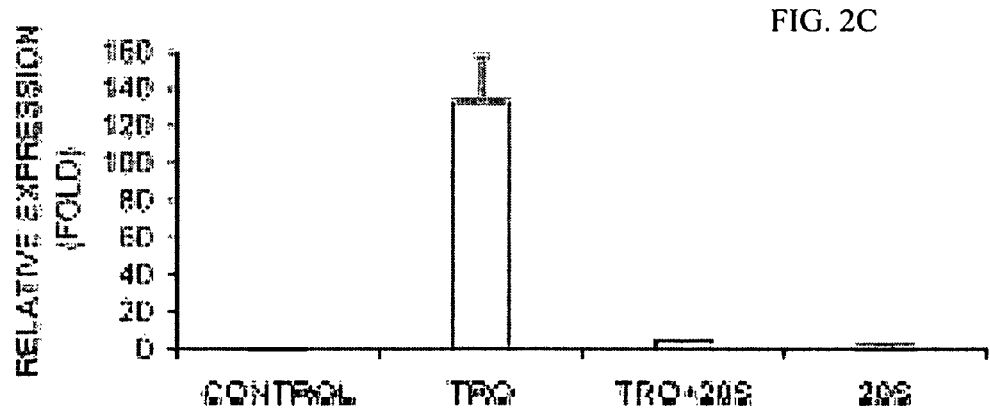

Effects of 20S on Adipogenic Differentiation and PPARγ and C/EBPα mRNA Expression Consistent with our previous report, treatment of M2 cells with Tro significantly increased adipocyte formation compared with control after 10 days, and this increase was significantly inhibited in the presence of 5 µM 20S (FIGS. 1A and 1B). See, Kha H T et al. 2004 Oxysterols regulate differentiation of mesenchymal stem cells: Pro-bone and anti-fat, J Bone Miner Res 19:830-840. FIG. 1A shows results for M2 cells treated at confluence with control vehicle, 10 µM Tro, or 5 µM 20S alone or in combination for 10 days. Adipocyte formation was examined by Oil red O staining. FIG. 1B shows the number of adipocytes for the conditions in FIG. 1A, quantitated by counting Oil red O-positive cells in five separate fields per well, and in three wells per experimental condition. The results are reported as the mean of triplicate determination ±SD ($p<0.0001$ for control vs. Tro and Tro vs. Tro+20S). To elucidate the mechanism(s) by which osteogenic oxysterols inhibit adipogenesis, we examined the effect of 20S on PPARγ expression in M2 cells. PPARγ expression was assessed by RT-qPCR after treating M2 cells with Tro in the presence or absence of 20S. Tro caused a significant increase in PPARγ mRNA expression after 24-96 h of treatment, with the level of expression increasing in a time-dependent manner (FIG. 2). Tro did not cause a detectable significant increase in PPARγ expression significantly at earlier time-points (data not shown). Tro-induced PPARγ expression was almost completely blocked by 20S at all time-points examined (FIG. 2). FIG. 2 shows the effect of 20S on PPARγ mRNA expression induced by Tro. M2 cells at confluence were treated with control vehicle, 10 µM Tro, or 5 µM 20S, alone or in combination for 24 hours (FIG. 2A), 48 hours (FIG. 2B), and 96 hours (FIG. 2C). PPARγ mRNA expression was measured by quantitative real-time PCR. Fold changes in gene expression to the control were calculated using the $\Delta\Delta Ct$ method and reported as the mean of triplicate determination ±SD ($p<0.0001$ for Tro vs. control and $p<0.001$ for Tro vs. Tro+20S at 24 hours (FIG. 2A); $p<0.0001$ for Tro vs. control and Tro vs. Tro+20S at 48 hours (FIG. 2B); $p<0.0001$ for Tro vs. control and Tro vs. Tro+20S at 96 hours (FIG. 2C).

Figure 3A:
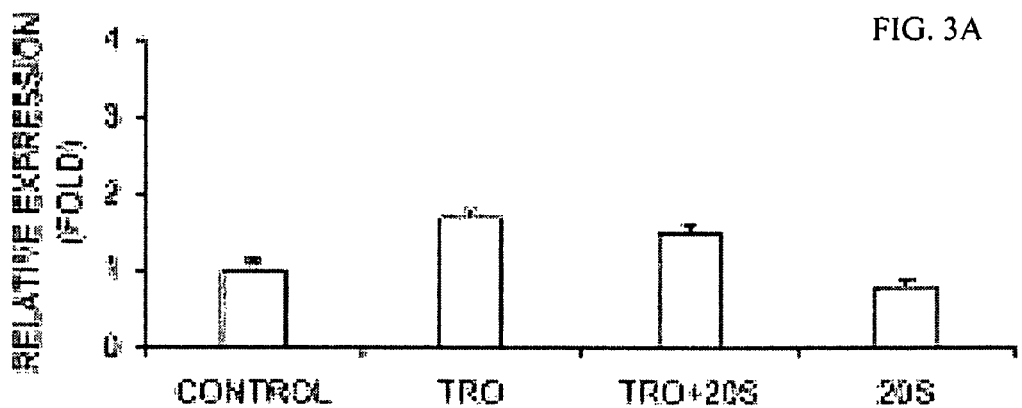
FIGS. 3A-3C present bar graphs illustrating C/EBPα mRNA expression by M2 cells after various treatments.
Figure 3B:
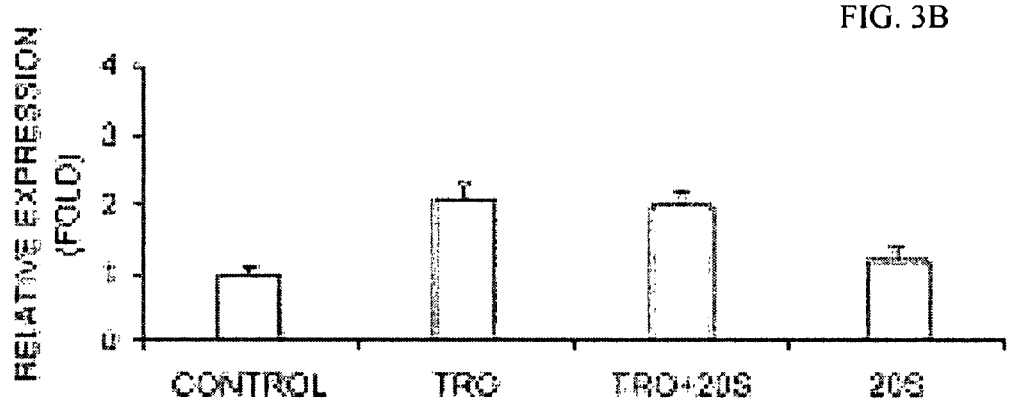
Figure 3C:
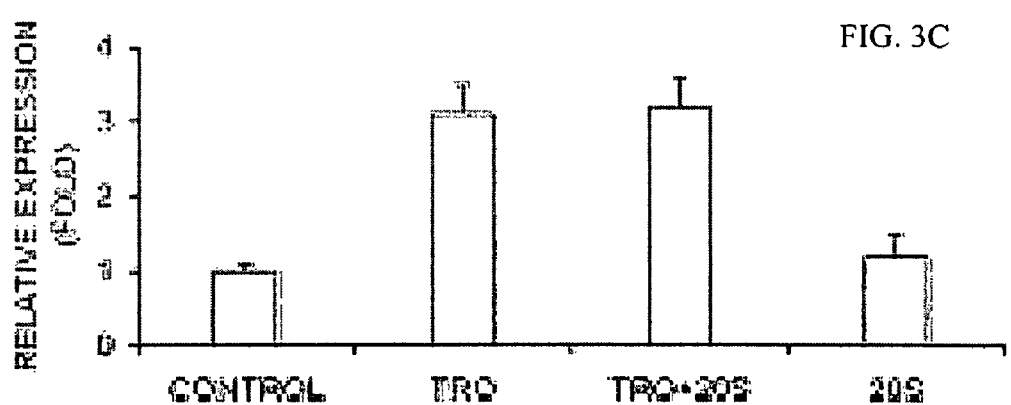

Furthermore, the expression of C/EBPα mRNA, a key adipogenic gene, was also significantly increased by Tro at 24 hours (FIG. 3A), 48 hours (FIG. 3B), and 96 hours (FIG. 3C) in a time dependent manner, but 20S did not inhibit this increase in C/EBPα expression at the time-points examined. FIG. 3 shows the effect of 20S on C/EBPα mRNA expression induced by Tro. M2 cells at confluence were treated with control vehicle, 10 µM Tro, or 5 µM 20S, alone or in combination for 24 (FIG. 3A), 48 (FIG. 3B), and 96 (FIG. 3C) hours. C/EBPα mRNA expression was measured by quantitative real-time PCR. Fold changes in gene expression relative to the control were calculated using the ΔΔCt method and reported as the mean of triplicate determination ±SD ($p<0.0001$ for Tro vs. control and $p<0.001$ for Tro+20S vs. control at 24 hours (FIG. 3A); $p<0.0001$ for Tro vs. control and $p<0.001$ for Tro+20S vs. control at 48 hours (FIG. 3B); $p<0.0001$ for Tro or Tro+20S vs. control at 96 hours (FIG. 3C).

Figure 4A:
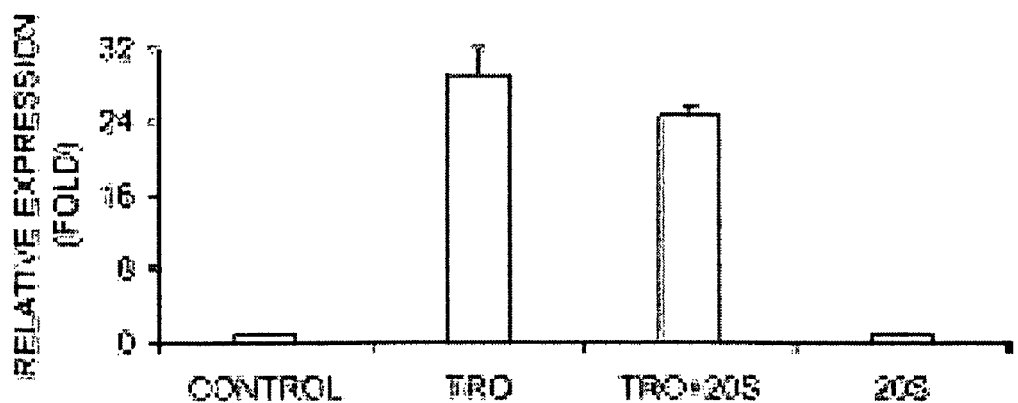
FIGS. 4A-4C present bar graphs illustrating aP2 mRNA expression by M2 cells after various treatments.
Figure 4B:
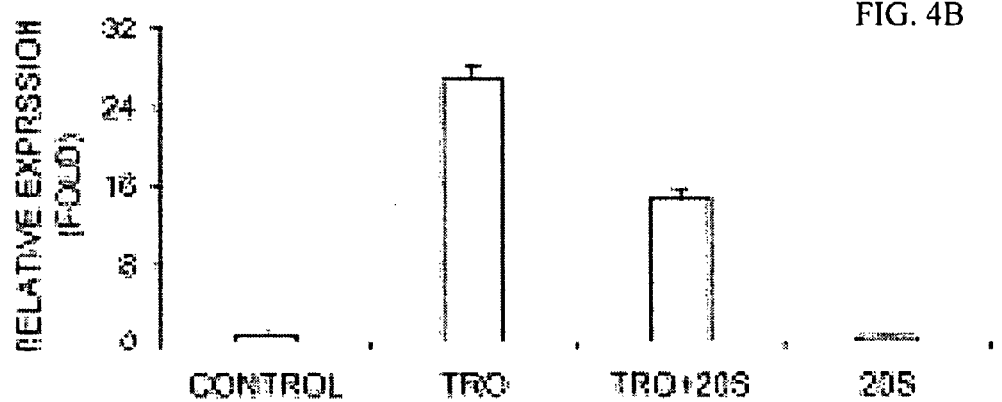
Figure 4C:
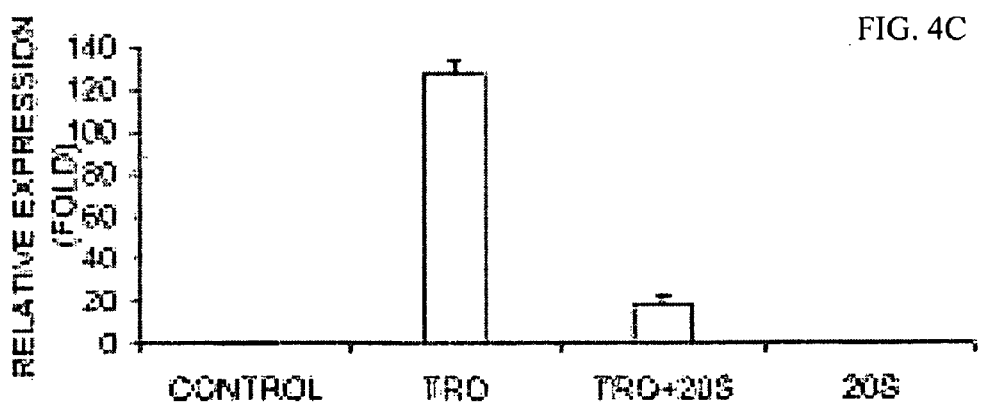

The expression of aP2, a downstream target of PPARγ, was significantly increased in Tro-treated cells, and this induction was inhibited by 20S (FIG. 4). FIG. 4 shows the effect of 20S on aP2 mRNA expression induced by Tro. M2 cells at confluence were treated with control vehicle, 10 µM Tro, or 5 µM 20S, alone or in combination for 24 hours (FIG. 4A), 48 hours (FIG. 4B), and 96 hours (FIG. 4C). aP2 mRNA expression was measured by quantitative real-time PCR. Fold changes in gene expression relative to the control were calculated using the ΔΔCt method and reported as the mean of triplicate determination ±SD ($p<0.0001$ for Tro or Tro+20S vs. control or 20S and $p<0.01$ for Tro vs. Tro+20S at 24 hours (FIG. 4A); $p<0.0001$ for Tro or Tro+20S vs. control or 20S and for Tro vs. Tro+20S at 48 hours (FIG. 4B); $p<0.0001$ for Tro vs. control, 20S, or Tro+20S and $p<0.001$ for Tro+20S vs. control or 20S at 96 hours (FIG. 4C)).

Figure 5A:
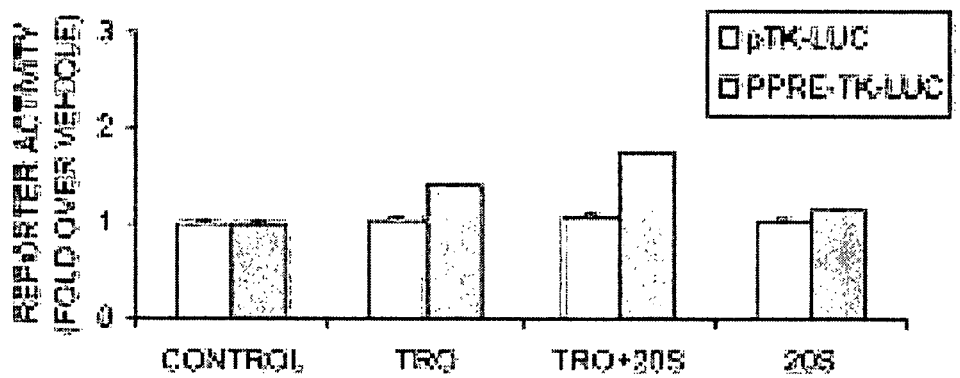
FIGS. 5A-5C present bar graphs illustrating reporter activity by M2 cells after various treatments.
Figure 5B:
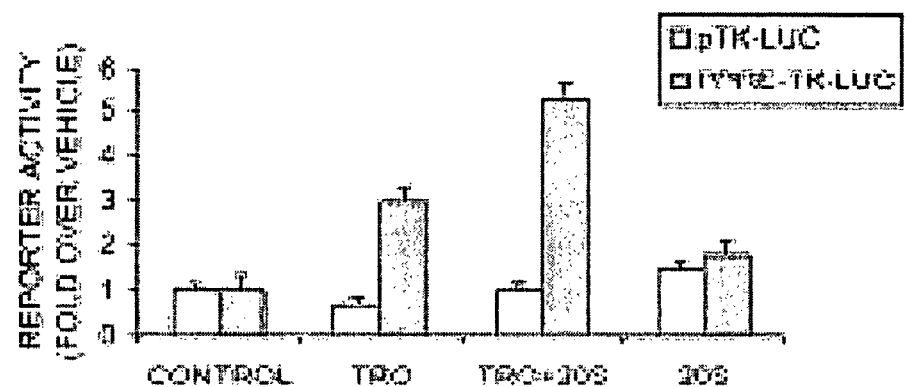
Figure 5C:
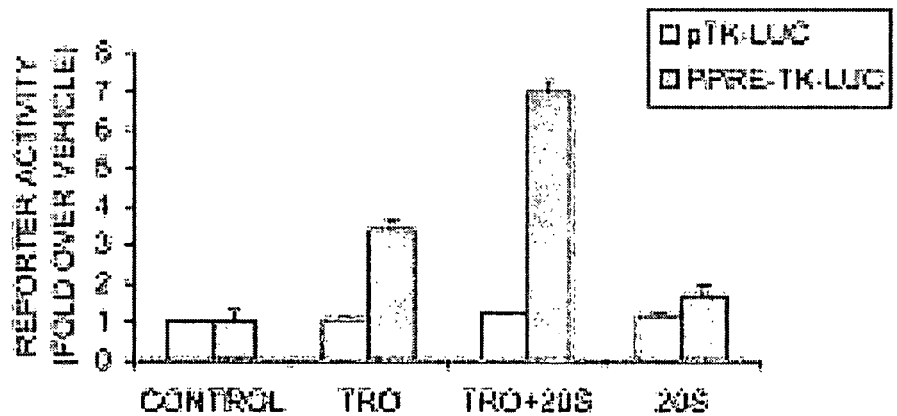

Next we examined whether, in addition to inhibiting PPARγ expression, 20S also inhibits transcriptional activity of PPARγ protein, i.e., its effect in inducing transcription of a reporter gene. M2 cells were transiently transfected with a reporter construct containing three tandem repeats of a PPRE (pTK-3×PPRE-Luciferase) or the control plasmid (pTK-Luciferase). Cells were treated with 10 µM Tro or control vehicle, and luciferase activity was measured after 24 and 48 h. Results showed that Tro induced a small but significant increase in reporter activity (40%; FIG. 5A). Interestingly, 20S did not inhibit Tro-induced PPRE reporter activity, but instead caused a small but significant increase in the Tro-induced response (FIG. 5A). Because Tro-induced PPRE reporter activity appeared to be low in M2 cells under baseline conditions, we used a PPARγ over-expression vector to transiently transfect the cells and assessed whether Tro-induced reporter activity was increased. Indeed, we found a more substantial reporter activity in PPARγ overexpressing cells in response to Tro after 24 (FIG. 5B) and 48 h (data not shown) of treatment. Consistent with the results obtained without PPARγ overexpression, 20S did not inhibit but rather enhanced Tro-induced PPRE reporter activity in cells overexpressing PPARγ. Because PPARγ and retinoid X receptor (RXR) form obligatory heterodimers, we studied whether 20S would have an effect when both PPARγ and RXRα were overexpressed. Co-transfection of M2 cells with PPARγ and RXRα overexpression plasmids showed similar results to transfection with only PPARγ overexpression plasmid, and 20S enhanced PPARγ-RXRα induced PPRE reported activity (FIG. 5C). FIG. 5 shows the effect of 20S on transcriptional activity of PPARγ. FIG. 5A shows results for M2 cells at 70% confluence in a 24-well plate transiently transfected with a PPRE reporter construct (pTK-3×PPRE-Luciferase) plasmid (PPRE-TK-LUC) or pTK-Luciferase plasmid (pTK-LUC) and pTK-Renilla-Luciferase plasmid. Luciferase activity was measured after 24 hours and normalized for transfection efficiency using the Renilla luciferase activity. Data are reported as the mean of triplicate determination ±SD ($p<0.001$ for control vs. Tro and Tro vs. Tro+20S). FIG. 5B shows results for M2 cells transiently transfected with a PPRE reporter plasmid (pTK-3×PPRE-Luciferase) (PPRE-TK-LUC) or pTK-Luciferase plasmid (pTK-LUC), along with CMX-PPARγ expression plasmid, and pTK-Renilla-Luciferase plasmid. Luciferase activity was normalized for transfection efficiency using the Renilla luciferase activity. Data are reported as the mean of triplicate determination ±SD ($p<0.0001$ for control vs. Tro and Tro vs. Tro+20S). FIG. 5C shows results for M2 cells transiently transfected as described for FIG. 5B along with CMX-RXRα expression plasmid. Luciferase activity was measured after 24 hours and normalized to the Renilla luciferase activity. Data are reported as the mean of triplicate determination ±SD ($p<0.0001$ for control vs. Tro and Tro vs. Tro+20S).

Role of Hedgehog Signaling in Anti-adipogenic Effects of 20S

Figure 6A:
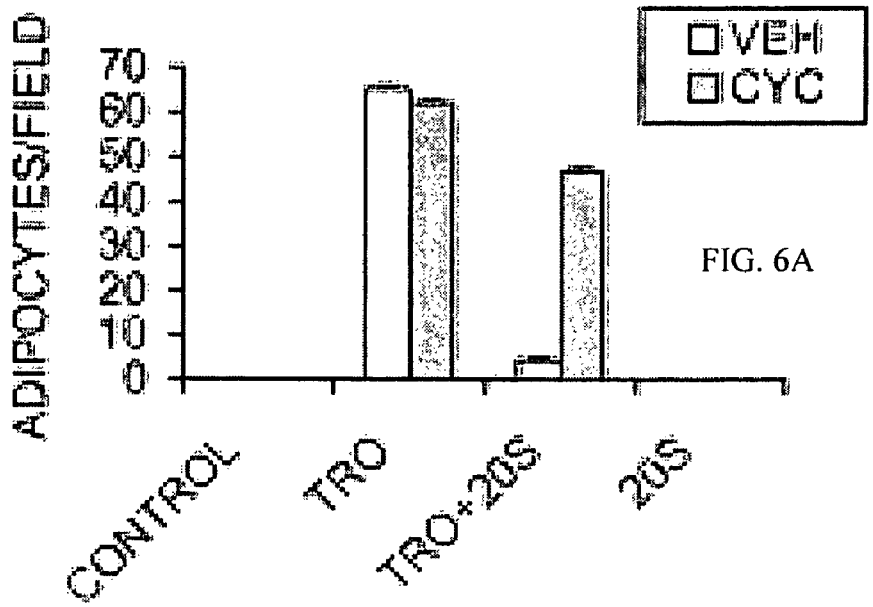
FIGS. 6A and 6B present bar graphs illustrating number of adipocytes generated from M2 cells after various treatments.
Figure 6B:
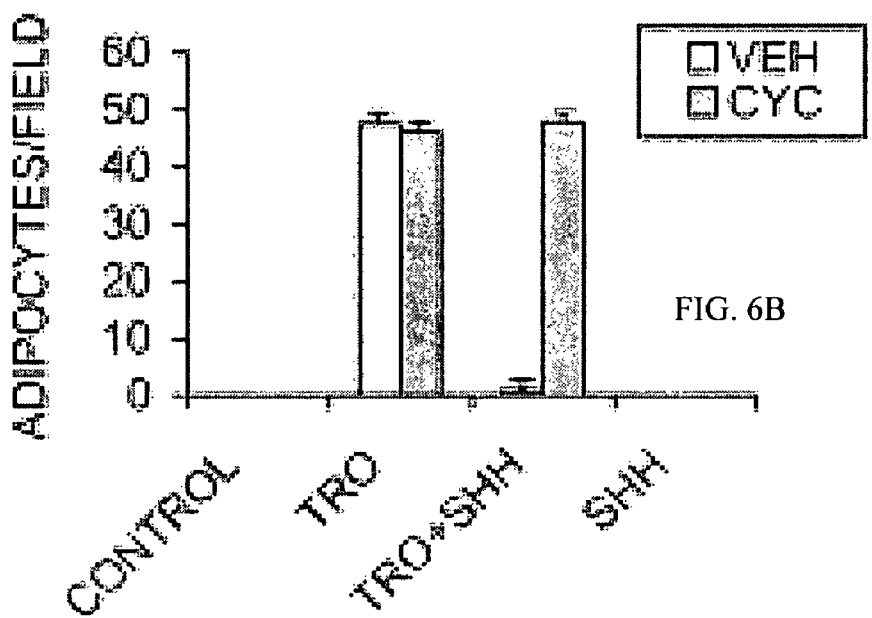

We previously found that osteogenic oxysterols stimulate osteoblastic differentiation of M2 cells by inducing hedgehog pathway activity, and activation of hedgehog pathway is pro-osteogenic and anti-adipogenic. See, Dwyer J R et al. 2007, Oxysterols are novel activators of the hedgehog signaling pathway in pluripotent mesenchymal cells, J Biol Chem 282: 8959-8968; Spinella-Jaegle S et al. 2001, Sonic hedgehog increases the commitment of pluripotent mesenchymal cells into the osteoblastic lineage and abolishes adipocytic differentiation, J Cell Sci 114:2085-2094; Suh J M et al. 2006, Hedgehog signaling plays a conserved role in inhibiting fat formation, Cell Metab 3:25-34; Richardson J A et al. 2005, Characterization of osteogenic oxysterols and their molecular mechanism(s) of action, J Bone Miner Res 20:S1; S414; Amantea C M et al. 2006, Oxysterols are novel activators of hedgehog and Wnt signaling, J Bone Miner Res 21:SI; S156. We evaluated whether the anti-adipogenic effects of 20S are mediated through the hedgehog signaling pathway by assessing the effect of hedgehog pathway inhibitor, cyclopamine, on the anti-adipogenic effects of 20S oxysterol. Consistent with previous results, Oil red O staining showed that Tro treatment greatly increased the number of adipocytes compared with control, 20S significantly inhibited adipocyte formation induced by Tro, and pretreatment with cyclopamine (4 µM) reversed the anti-adipogenic effects of 20S (FIG. 6A). Shh also significantly inhibited Tro-induced adipocyte formation, and cyclopamine pretreatment completely reversed the anti-adipogenic effects of Shh (FIG. 6B). Cyclopamine also reversed the inhibitory effects of 20S on the expression of adipogenic differentiation marker genes, LPL and aP2 (data not shown).

Figure 6C:
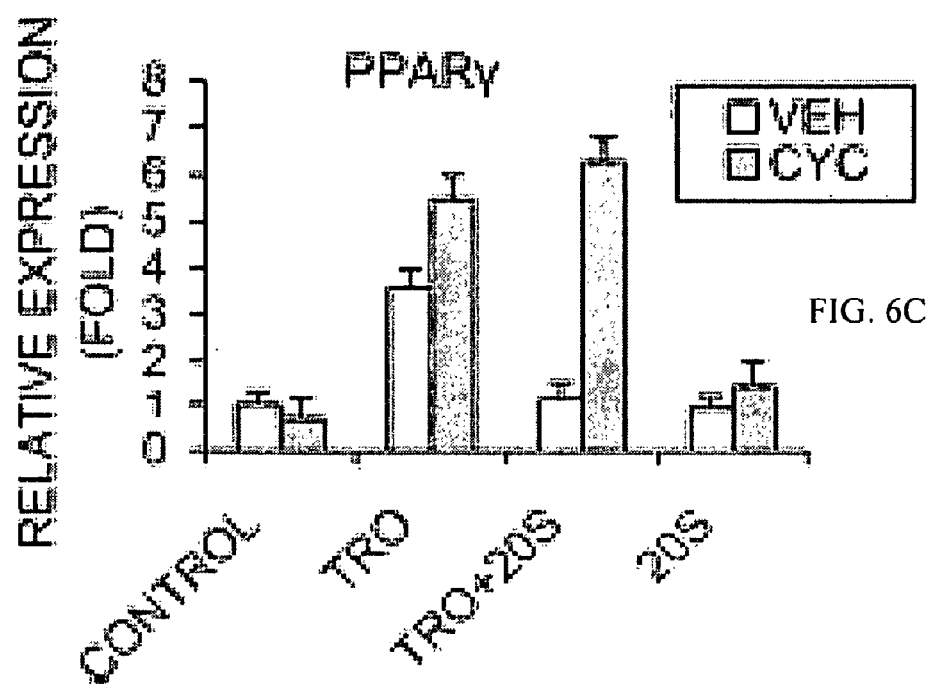
FIGS. 6C and 6D present bar graphs illustrating relative expression of PPARγ by M2 cells after various treatments.
Figure 6D:
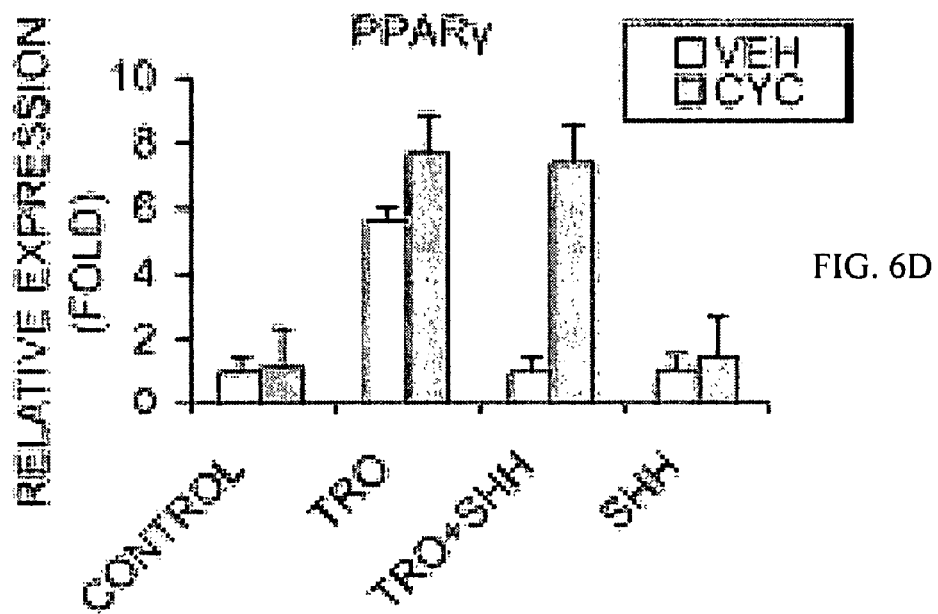

To determine if cyclopamine's effect on the antiadipogenic actions of 20S and Shh is produced at the level of PPARγ expression, we evaluated the effects of cyclopamine on PPARγ mRNA expression by RT-qPCR after 48 h of treatment with Tro. Consistent with earlier results, Tro caused a significant increase in PPARγ expression, which was blocked by 20S and Shh, and pretreatment with cyclopamine completely abolished the inhibitory effect of 20S and Shh (FIGS. 6C and 6D).

Figure 6E:
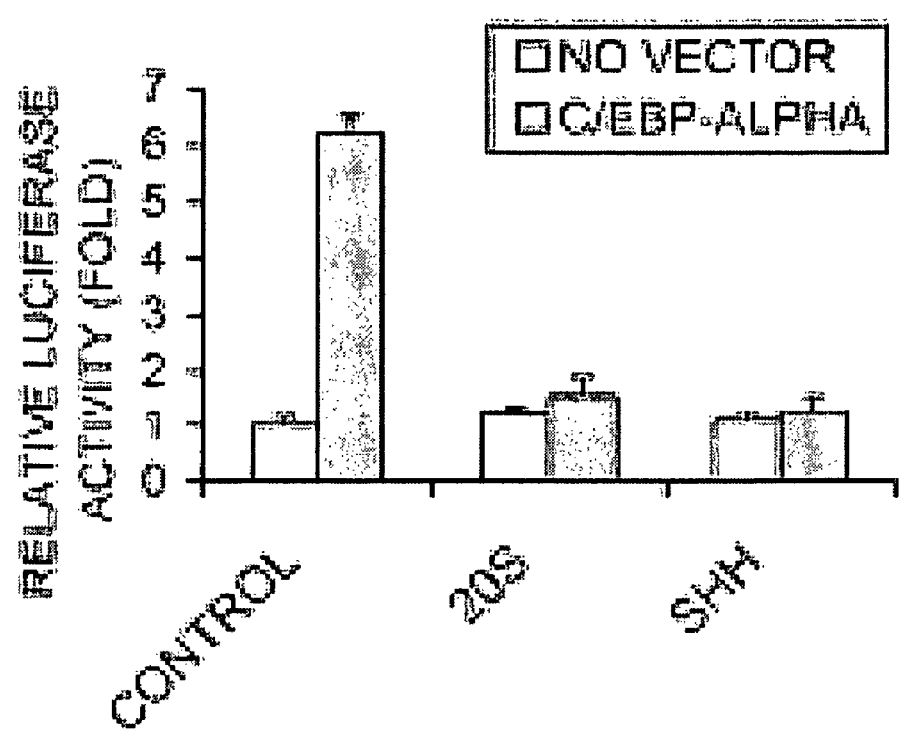
FIG. 6E presents bar graphs illustrating relative luciferase activity in M2 cells after various treatments.

To determine if 20S and Shh inhibit PPARγ expression by acting directly on its promoter, we focused on C/EBPα regulated PPARγ promoter activity. PPARγ promoter activity assays using a murine PPARγ2 promoter construct luciferase plasmid (p19-PPARγ2) containing 2×C/EBPα binding sites, transfected into M2 cells along with MSV-C/EBPα over-expression plasmid, showed that C/EBPα overexpression stimulated PPARγ2 promoter activity 6-fold, which was inhibited by both 20S and Shh (FIG. 6E).

FIG. 6 shows that the hedgehog pathway inhibitor, cyclopamine, blocks inhibitory effects of 20S and Shh on Tro-induced adipogenic differentiation and PPARγ mRNA expression, and 20S and Shh inhibit the PPARγ promoter activity induced by C/EBPα overexpression. FIGS. 6A and 6B show results for M2 cells at confluence treated with control vehicle (control), 10 µM Tro, or a combination of Tro and 5 µM 20S or 200 ng/mL Shh, with or without a 2-h pretreatment with control vehicle (VEH) or 4 µM cyclopamine (CYC). After 10 days, adipocyte formation was measured by Oil red O staining. The number of adipocytes was determined by counting Oil red O-positive cells in five separate fields per well, in three wells per experimental condition. The results are reported as the mean of triplicate determination ±SD (FIG. 6A: p<0.0001 for control, Tro+20S, or 20S vs. Tro, Tro+Cyclopamine, or Tro+20S+Cyclopamine and Tro+20S vs. Tro, Tro+Cyclopamine, or Tro+20S+Cyclopamine, and Tro+Cyclopamine vs. Tro+20S+Cyclopamine; FIG. 6B: p<0.0001 for control, Tro+20S, or 20S vs. Tro, Tro+Cyclopamine, or Tro+20S+Cyclopamine and Tro+20S vs. Tro, Tro+Cyclopamine, or Tro+20S+Cyclopamine). FIGS. 6C and 6D show results for M2 cells at confluence treated with control vehicle (control), 10 µM Tro, or 5 µM 20S, alone or in combination, with or without a 2-h pretreatment with control vehicle (VEH) or 4 µM cyclopamine (CYC). After 48 h, PPARγ mRNA expression was measured by quantitative real-time PCR. Fold changes in gene expression relative to the control were calculated using the ΔΔCt method and reported as the mean of triplicate determination ±SD (FIG. 6C; p<0.0001 for control vs. Tro+Cyclopamine and Tro+20S+Cyclopamine, Tro vs. Tro+20S, and Tro+20S vs. Tro+20S+Cyclopamine; p<0.001 for Tro vs. Tro+Cyclopamine; FIG. 6D: p<0.0001 for control or Tro+Shh vs. Tro, Tro+Cyclopamine, or Tro+Shh+Cyclopamine; p<0.001 for Tro vs. control or Tro+Shh). Figure E shows results for M2 cells transiently transfected with a murine PPARγ2 promoter construct luciferase plasmid (p19-PPARγ2), alone (No Vector) or with MSV-C/EBPα overexpression plasmid (C/EBP-Alpha) and pTK-Renilla-Luciferase plasmid. Luciferase activity was measured after 24 h and normalized for transfection efficiency using the Renilla luciferase activity. Data are reported as the mean of triplicate determination ±SD (p<0.001 for control vs. control+C/EBPα and for control+C/EBPα vs. 20S+C/EBPα or Shh+C/EBPα).

To elucidate the molecular mechanism(s) by which 20S inhibits PPARγ expression and adipogenic differentiation, the effect of modulating Hedgehog, Wnt, and MAPK signaling in turn on PPARγ expression was studied. Modulation of Hedgehog, Wnt, and MAPK signaling was found to mediate the osteogenic effects of oxysterols. In studying the effect of modulating a given signaling mechanism, four sets of M2 cells were used: a control set, a set to which only Tro was administered, a set to which both Tro and 20S were administered, and a set to which only 20S was administered. Within a given set of M2 cells, one part was further treated with a given signaling inhibitor, and another part was not treated with a signaling inhibitor.

The canonical Wnt signaling inhibitor, Dkk-1 reversed the inhibitory effect of 20S on Tro-induced PPARγ expression by 10%. The MAPK signaling inhibitor, PD98059 (PD) reversed the inhibitory effect of 20S on Tro-induced PPARγ expression by 45%.

The inhibitory effects of 20S on Tro-induced adipocyte formation in cultures of M2 cells was reversed by 70%, 40%, and 50%, by Cyclopamine (administered at 4 µM), Dkk-1 (administered at 1 µg/mL), and PD98059 (administered at 20 µM), respectively. Thus, the inhibition of adipogenesis by the osteogenic oxysterol, 20S, appears to be mediated via a hedgehog-, Wnt-, and MAPK-dependent mechanism(s).

Discussion

This study showed that the inhibition of adipogenesis by the osteogenic oxysterol 20S is associated with the inhibition of PPARγ mRNA expression in MSCs. Because in this study, adipogenic differentiation was induced with Tro, a ligand for PPARγ protein, and given the fact that PPARγ does not seem to induce its own expression, it is likely that the positive feedback loop between C/EBPα and PPARγ regulates the induction of key adipogenic genes and adipocyte formation. See, Wu Z et al. 1999 Crossregulation of C/EBPα and PPARγ controls the transcriptional pathway of adipogenesis and insulin sensitivity, Mol Cell 3:151-158. 20S specifically inhibited PPARγ expression, but not C/EBPα expression, in early adipogenic differentiation induced by Tro. Given that 20S did not inhibit C/EBPα expression, we examined whether inhibition was the level of C/EBPα controlled PPARγ promoter activity. Indeed, the PPARγ2 promoter activity assays showed that 20S and Shh inhibit C/EBPα-induced PPARγ promoter activity. In a non-limiting possible mechanism explaining oxysterol-mediated inhibition of PPAR expression, these data suggest that inhibition of PPARγ expression may be at the level of PPARγ promoter. The molecular mechanism for this inhibition remains to be elucidated; however, it may involve 20S- and Shh-induced regulation of co-activators and/or co-repressors that mediate PPARγ promoter activity. One limitation of this study is that we did not show the effects of 20S and Shh on PPARγ protein levels directly, although their inhibitory effect on PPARγ target gene expression suggests a potentially similar inhibitory effect on PPARγ protein expression.

Our results also showed that the inhibitory effects of 20S on adipogenesis were mediated by hedgehog signaling, which is also involved in mediating the osteogenic effects of 20S. See, Dwyer J R et al. 2007, Oxysterols are novel activators of the hedgehog signaling pathway in pluripotent mesenchymal cells, J Biol Chem 282:8959-8968; Richardson J A et al. 2005, Characterization of osteogenic oxysterols and their molecular mechanism(s) of action, J Bone Miner Res 20:S1,S414; Amantea C M et al. 2006, Oxysterols are novel activators of hedgehog and Wnt signaling. J Bone Miner Res 21:SI, S156. This signaling pathway plays a role in the regulation of osteogenic and adipogenic differentiation of progenitor cells. See, Spinella-Jaegle S et al. 2001, Sonic hedgehog increases the commitment of pluripotent mesenchymal cells into the osteoblastic lineage and abolishes adipocytic differentiation, J Cell Sci 114:2085-2094; Suh J M et al. 2006, Hedgehog signaling plays a conserved role in inhibiting fat formation, Cell Metab 3:25-34. Cyclopamine significantly blocked the inhibition of adipocyte formation and PPARγ mRNA expression by 20S, which suggests that activation of the hedgehog signaling pathway is the prominent antiadipogenic mechanism by which 20S regulates adipogenic, as well as osteogenic, differentiation of MSCs. Shh has been shown to inhibit adipogenesis and the expression of PPARγ in C3H10T1/2 embryonic fibroblasts. See, Spinella-Jaegle S et al. 2001, Sonic hedgehog increases the commitment of pluripotent mesenchymal cells into the osteoblastic lineage and abolishes adipocytic differentiation, J Cell Sci 114:2085-2094. In addition, Shh was reported to inhibit adipogenic differentiation and expression of adipogenic genes in 3T3-L1 pre-adipocytes. See, Suh J M et al. 2006, Hedgehog signaling plays a conserved role in inhibiting fat formation, Cell Metab 3:25-34. Furthermore, a dominant-negative form of Gli (the transcription factor that mediates hedgehog-regulated gene expression) and cyclopamine were shown to inhibit hedgehog signaling while stimulating adipogenic differentiation in 3T3-L1 cells. See, Suh J M et al. 2006 Hedgehog signaling plays a conserved role in inhibiting fat formation, Cell Metab 3:25-34. One mechanism by which 20S exerts its anti-adipogenic effects through hedgehog signaling may involve the induction of antiadipogenic transcription factors, such as Gilz, GATAs, and pref-1. Shh was shown to increase the levels of Gilz, GATA2, GATA3, or pref-1 in mouse N1H-3T3 fibroblasts, C3H10T1/2 pluripotent mesenchymal cells, and 3T3-L1 pre-adipocytes. See, Suh J M et al. 2006; Ingram W J et al. 2002, Novel genes regulated by sonic hedgehog in pluripotent mesenchymal cells, Oncogene 21:8196-8205. GATA-2 and GATA-3 inhibit PPARγ expression and adipogenic differentiation through direct binding to the PPARγ promoter, as well as by physically interacting with C/EBPα. See, Tong Q et al. 2000, Function of GATA transcription factors in preadipocyte-adipocyte transition, Science 290: 134-138; Tong Q et al. 2005, Interaction between GATA and the C/EBP family of transcription factors is critical in GATA-mediated suppression of adipocyte differentiation, Mol Cell Biol 25:706-715. Gilz and pref-1 also inhibit adipogenic differentiation and keep 3T3-L1 as preadipocytes. See, Suh J M et al. 2006; Shi X et al. 2003, A glucocorticoid-induced leucine-zipper protein, GILZ, inhibits adipogenesis of mesenchymal cells, EMBO Rep 4:374-380. We examined the effects of 20S on GATA2, GATA3, Gilz, and pref-1 expression in M2 cells using RT-qPCR and on GATA transcriptional activity using a GATA reporter transfected into M2 cells. Results showed that 20S does not increase GATA2/GATA3, Gilz, and pref-1 gene expression nor GATA transcriptional activity assessed after 24 and 48 h of treatments (data not shown). The molecular mechanism(s) by which 20S inhibits PPARγ expression in a hedgehog signaling-dependent manner remains unclear. Although 4 µM cyclopamine treatment fully reversed the inhibitory effect of 20S on PPARγ mRNA expression at 48 h, it did not completely reverse 20S effects on adipocyte formation as measured by Oil red O staining at late stages of cell differentiation, and increasing the dose of cyclopamine from 4 to 8 µM did not have any additional effect on adipocyte formation (data not shown). However, the inhibitory effects of Shh on PPARγ mRNA expression as well as adipocyte formation were completely reversed by 4 pM cyclopamine. This suggests that, in addition to hedgehog signaling, other anti-adipogenic mediators may contribute to the complete inhibition of adipogenesis by 20S in MSCs.

Figure 8:
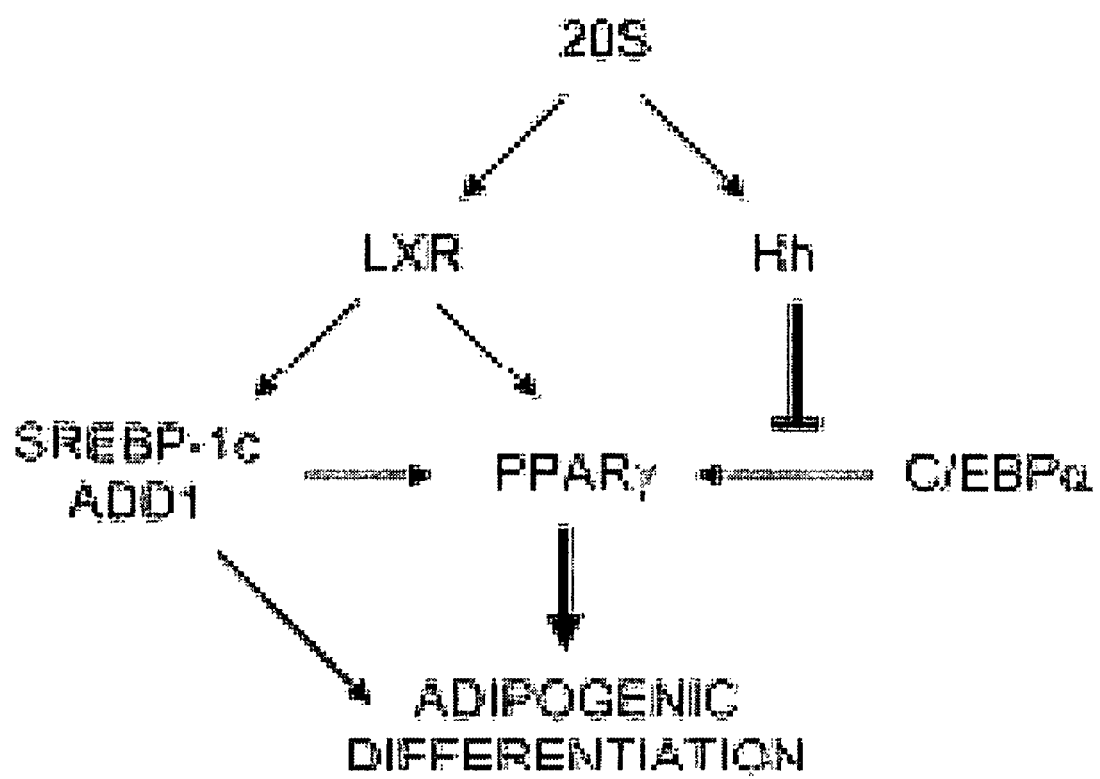
FIG. 8 presents an illustration of the regulation of adipogenic differentiation of bone MSCs by 20(S)-hydroxycholesterol (20S).

Unlike Shh, 20S activates not only the hedgehog pathway but also liver X receptor (LXR) signaling (FIG. 8). FIG. 8 illustrates the regulation of adipogenic differentiation of bone MSCs by 20S. 20S activates LXRs and Hh signaling pathways. LXR activation increases the expression of SREBP-1c/ADD1. LXRs and PPARγ positively regulate each other's expression. Moreover, SREBP-1c/ADD1 regulates adipogenesis through PPPAy gene expression and through the production of a endogenous PPARγ ligand(s). Despite activation of LXRs by 20S oxysterol, the activation of Hh signaling induced by 20S inhibits PPARγ expression and adipogenic differentiation of M2 cells.

Oxysterols are ligands for LXRs, which regulate cholesterol, lipid, and carbohydrate metabolism. LXR activation increases the expression of sterol regulatory element binding protein-1c (SREBP-1c)/adipogenic differentiation of factor 1 (ADD1), which induces the expression of fatty acid synthase, glycerol-3-phosphate acyltransferase, and stearyl CoA desaturase 2 during adipogenic differentiation. It has been shown that activation of LXRs increases lipid accumulation during adipogenic differentiation of 3T3-L1 and 3T3-F422A pre-adipocytes. LXRs and PPARγ seem to positively regulate each other's expression. The expression of LXRα is increased directly by PPARγ activation in 3T3-L1 pre-adipocytes and in a mouse model. Juvet L K et al. 2003, On the role of liver X receptors in lipid accumulation in adipocytes, Mol Endocrinol 17:172-182. Furthermore, PPARγ promoter contains the conserved binding site for LXR, and LXR activation increases PPARγ expression. See, Seo J B et al. 2004, Activated Liver X receptors stimulate adipocyte differentiation through induction of peroxisome proliferators-activated receptor γ expression, Mol Cell Biol 74:3430-3444. In addition, SREBP1/ADD1 regulates adipogenesis through PPARγ gene expression through E-box motifs in the PPARγ promoter and through the production of an endogenous PPARγ ligand(s) to increase PPARγ transcriptional activity. Fajas L et al. 1999, Regulation of peroxisome proliferators-activated receptor γ expression by adipocyte differentiation and determination 1: Implications for adipocyte differentiation and metabolism, Mol Cell Biol 19:5495-5503; Kim J B et al. 1998 ADD1/SREBP1 activates PPARγ through the production of endogenous ligand, Proc Natl Acad Sci USA 95:4333-4337.

In this study, we examined whether 20S, in addition to inhibiting PPARγ mRNA expression, also inhibits PPARγ transcriptional activity. When a vector was inserted into the cells that caused the expression of PPARγ protein, without the normal transcriptional machinery that drives PPARγ mRNA expression from the cellular genome, we found that troglitazone-induced PPARγ transcriptional induction activity was not inhibited but rather enhanced by 20S. Given the positive interactions between LXR and PPARγ in the context of adipogenesis, one potential explanation for this enhancement is that LXR activation by 20S causes further stimulation of troglitazone-induced PPARγ transcriptional activity. Despite the activation of LXRs by 20S in M2 cells (data not shown), the activation of hedgehog signaling by 20S inhibited PPARγ mRNA expression and adipogenic differentiation of these cells, suggesting that this level of hedgehog pathway activation is capable of counteracting any LXR-mediated pro-adipogenic effects of 20S. The role of LXRs in regulating adipogenesis in bone MSCs remains unclear.

Altogether, this study shows that specific oxysterols with pro-osteogenic and anti-adipogenic properties serve as regulators of a shift in differentiation of MSCs into osteoblasts and away from adipocytes. Such oxysterols may be used to regulate the lineage-specific differentiation of MSC under physiological and/or pathological conditions.

Example V

Oxysterol Inhibition of PPAR

Figure 7A:
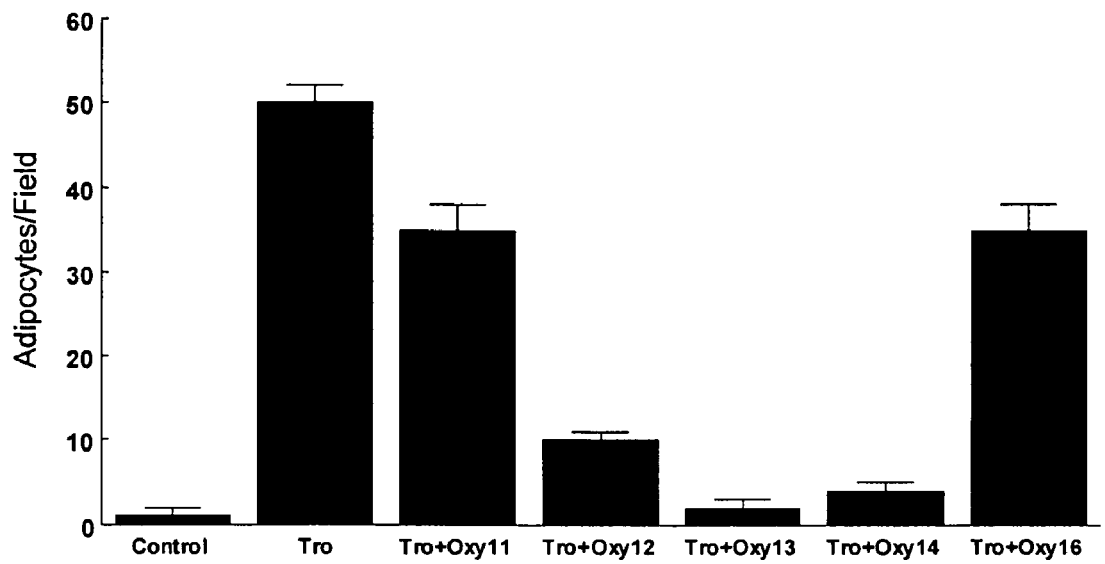
FIG. 7A presents bar graphs illustrating the number of adipocytes after various treatments.

Synthetic oxysterol compounds were studied for inhibition of adipogenesis and PPAR expression. FIG. 7A shows results obtained with M2-10B4 bone marrow stromal cells treated with control vehicle or the PPARγ activator, troglitazone (Tro, 10 µM), in the presence or absence of various oxysterols (5 µM), as indicated. After 10 days of treatment, cells were stained with Oil-red-O to detect adipocytes, and the number of positively stained cells was determined using light microscopy. Data from a representative experiment are reported as the mean of triplicate determination (average of five fields per well, 3 wells per experimental condition) ±SD. The data indicate that the oxysterol compounds identified as Oxy11, Oxy12, Oxy13, Oxy14, and Oxy16 had an inhibitory effect on Tro-induced adipocyte formation.

Figure 7B:
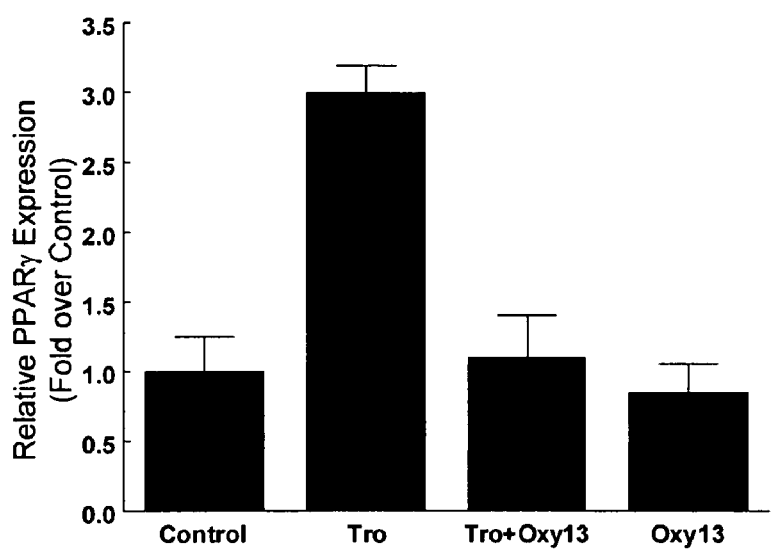
FIG. 7B presents bar graphs illustrating PPARγ expression by M2 cells after various treatments.

FIG. 7B shows results obtained with M2-10B4 bone marrow stromal cells treated with control vehicle or the PPARγ activator, troglitazone (Tro, 10 µM), in the presence or absence of Oxy13 (5 μM), as indicated. After 48 hours of treatment, RNA was extracted from cells and analyzed for PPARγ expression by Q-RT-PCR. Data from a representative experiment, normalized to GAPDH expression, are reported as the mean of triplicate determinations ±SD. The data indicate that the oxysterol compound identified as Oxy13 inhibits Tro-induced PPARγ expression.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above are hereby incorporated by reference in their entirety.

What is claimed is:

1. A method for inhibiting expression of a peroxisome proliferator activated receptor (PPAR) in a cell, comprising:
    contacting at least one oxysterol compound with the cell in an amount effective to inhibit expression of the PPAR; and
    measuring inhibition of expression of the PPAR.

2. The method of claim 1, wherein the inhibited expression is of PPAR gamma.

3. The method of claim 1, wherein the cell is a marrow stromal cell (MSC) and the at least one oxysterol compound stimulates osteogenesis of the cell.

4. The method of claim 1, wherein the cell is a marrow stromal cell (MSC), and the at least one oxysterol compound has inhibits adipogenesis of the cell.

5. The method of claim 1, wherein the at least one oxysterol compound is an activator of the hedgehog signaling pathway.

6. The method of claim 1, wherein the at least one oxysterol compound is selected from the group consisting of 20(S)-hydroxycholesterol,

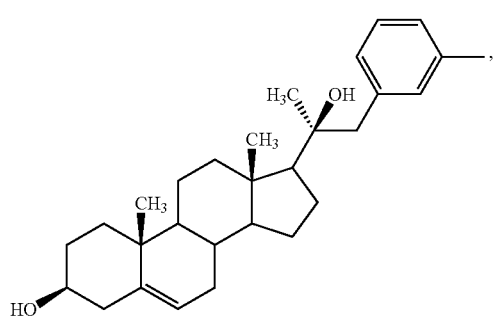

Oxy 11

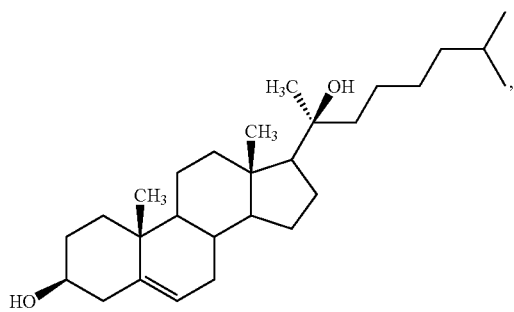

Oxy 12

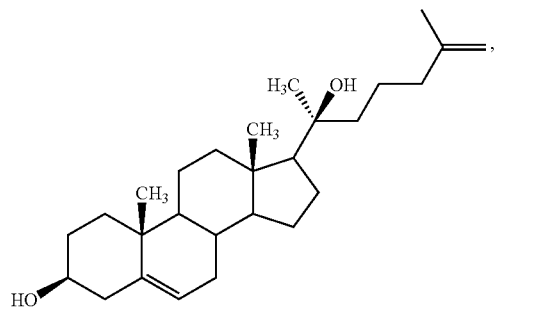

Oxy 13

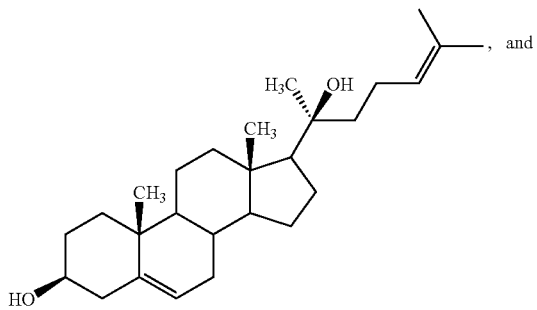

Oxy 14, and

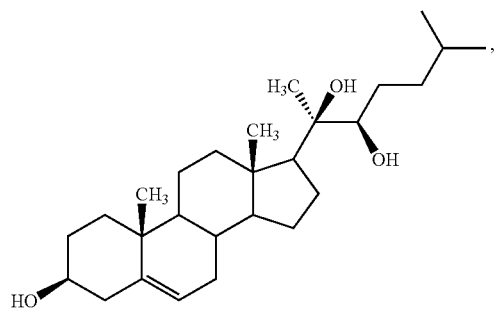

Oxy 16 and combinations thereof.

7. The method of claim 1, wherein the cell is a marrow stromal cell.

8. The method of claim 1, wherein contacting the at least one oxysterol compound with the cell inhibits expression and/or activity of a PPAR target gene; and further comprising measuring inhibition of expression of the PPAR target gene.

9. The method of claim 8, wherein the PPAR target gene is a gene selected from the group consisting of adipocyte protein 2 (aP2) and lipoprotein lipase (LPL).

10. The method of claim 1, wherein the inhibition of PPAR expression is sufficient to inhibit a PPAR mediated response in the cell.

11. The method of claim 1, wherein the cell is in vitro.

12. The method of claim 1, wherein the cell is in a subject.

13. The method of claim 1, wherein the cell is in a human.

14. A method of treating a condition associated with increased adipogenesis in a subject, comprising administering to the subject an amount of an oxysterol compound effective to treat the condition, wherein the oxysterol compound has been shown to be in an amount that is effective to inhibit PPAR expression.

15. A method of treating a condition associated with excessive accumulation of intracellular and/or extracellular fats and/or lipids in a subject, comprising administering to the subject an amount of an oxysterol compound effective to treat the condition, wherein the oxysterol compound has been shown to be in an amount that is effective to inhibit PPAR expression.

16. A method for identifying an oxysterol compound that inhibits expression of PPAR, comprising:
  screening a candidate oxysterol compound for the ability to inhibit expression of PPAR in an in vitro assay; and
  selecting a candidate oxysterol compound that measurably inhibits PPAR expression.

17. The method of claim 16, wherein the screening comprises
  measuring the ability of the candidate oxysterol to reduce the stimulation of PPAR expression by a PPAR agonist.

18. The method of claim 17,
  wherein the PPAR agonist is contacted with the cell in the presence and in the absence of the candidate oxysterol; and the amount of expression of PPAR is at least 3-fold less when measured in the presence of the candidate oxysterol than when measured in the absence of the candidate oxysterol.

19. The method of claim 17,
  wherein the cell is a marrow stromal cell,
  wherein the PPAR expression is PPAR gamma expression, and
  wherein the PPAR agonist is troglitazone.

* * * * *